(12) United States Patent
Pamula et al.

(10) Patent No.: US 8,637,317 B2
(45) Date of Patent: Jan. 28, 2014

(54) METHOD OF WASHING BEADS

(75) Inventors: Vamsee K. Pamula, Durham, NC (US);
Arjun Sudarsan, Durham, NC (US);
Ramakrishna Sista, Morrisville, NC (US)

(73) Assignee: Advanced Liquid Logic, Inc., Morrisville, NC (US)

( * ) Notice: Subject to any disclaimer, the term of this patent is extended or adjusted under 35 U.S.C. 154(b) by 282 days.

(21) Appl. No.: 12/985,409

(22) Filed: Jan. 6, 2011

(65) Prior Publication Data

US 2011/0114490 A1    May 19, 2011

Related U.S. Application Data

(63) Continuation-in-part of application No. 11/639,531, filed on Dec. 15, 2006, and application No.
(Continued)

(51) Int. Cl.
*G01N 15/06* (2006.01)

(52) U.S. Cl.
USPC ...... 436/43; 422/68.1; 422/82.01; 422/82.02; 422/502; 422/503; 422/509; 436/149; 436/150; 436/174; 436/179; 436/180

(58) Field of Classification Search
USPC .................. 422/50, 68.1, 82.01, 82.02, 100; 436/43, 149, 150, 174, 179, 180
See application file for complete search history.

(56) References Cited

U.S. PATENT DOCUMENTS

| 4,390,403 A | 6/1983 | Batchelder |
| 4,454,232 A | 6/1984 | Breglio et al. |

(Continued)

FOREIGN PATENT DOCUMENTS

| EP | WO03069380 A1 | 8/2003 |
| EP | W02004027490 A1 | 4/2004 |

(Continued)

OTHER PUBLICATIONS

PCT International Search Report and Written Opinion for PCT/US2006/047486 dated May 2, 2008.

(Continued)

*Primary Examiner* — Brian J Sines
(74) *Attorney, Agent, or Firm* — William A. Barrett

(57) ABSTRACT

The invention provides a method of redistributing magnetically responsive beads in a droplet. The method may include providing a droplet including magnetically responsive beads. The droplet may be provided within a region of a magnetic field having sufficient strength to attract the magnetically responsive beads to an edge of the droplet or towards an edge of the droplet, or otherwise regionalize or aggregate beads within the droplet. The method may also include conducting on a droplet operations surface one or more droplet operations using the droplet without removing the magnetically responsive beads from the region of the magnetic field. The droplet operations may in some cases be electrode-mediated. The droplet operations may redistribute and/or circulate the magnetically responsive beads within the droplet. In some cases, the droplet may include a sample droplet may include a target analyte. The redistributing of the magnetically responsive beads may cause target analyte to bind to the magnetically responsive beads. In some cases, the droplet may include unbound substances in a wash buffer. The redistributing of the magnetically responsive beads causes unbound substances to be freed from interstices of an aggregated set or subset of the magnetically responsive beads.

11 Claims, 42 Drawing Sheets

Related U.S. Application Data

12/985,409, which is a continuation of application No. PCT/US2009/050101, filed on Jul. 9, 2009.

(60) Provisional application No. 60/745,058, filed on Apr. 18, 2006, provisional application No. 60/745,039, filed on Apr. 18, 2006, provisional application No. 60/745,043, filed on Apr. 18, 2006, provisional application No. 60/745,059, filed on Apr. 18, 2006, provisional application No. 60/745,914, filed on Apr. 28, 2006, provisional application No. 60/745,950, filed on Apr. 28, 2006, provisional application No. 60/746,797, filed on May 9, 2006, provisional application No. 60/746,801, filed on May 9, 2006, provisional application No. 60/806,412, filed on Jun. 30, 2006, provisional application No. 60/807,104, filed on Jul. 12, 2006, provisional application No. 61/079,346, filed on Jul. 9, 2008, provisional application No. 61/080,731, filed on Jul. 15, 2008, provisional application No. 61/084,637, filed on Jul. 30, 2008, provisional application No. 61/103,302, filed on Oct. 7, 2008, provisional application No. 61/108,997, filed on Oct. 28, 2008, provisional application No. 61/122,791, filed on Dec. 16, 2008, provisional application No. 61/149,808, filed on Feb. 4, 2009.

(56) References Cited

U.S. PATENT DOCUMENTS

| | | |
|---|---|---|
| 4,863,849 A | 9/1989 | Melamede |
| 5,240,994 A | 8/1993 | Brink et al. |
| 5,472,881 A | 12/1995 | Beebe et al. |
| 5,486,337 A | 1/1996 | Ohkawa |
| 5,770,391 A | 6/1998 | Foote et al. |
| 5,770,457 A | 6/1998 | Stocker et al. |
| 5,846,396 A | 12/1998 | Zanzucchi et al. |
| 5,851,769 A | 12/1998 | Gray et al. |
| 5,980,719 A | 11/1999 | Cherukuri et al. |
| 6,106,685 A | 8/2000 | McBride et al. |
| 6,210,891 B1 | 4/2001 | Nyren et al. |
| 6,258,568 B1 | 7/2001 | Nyren |
| 6,294,063 B1 | 9/2001 | Becker et al. |
| 6,319,668 B1 | 11/2001 | Nova et al. |
| 6,379,929 B1 | 4/2002 | Burns et al. |
| 6,432,290 B1 | 8/2002 | Harrison et al. |
| 6,454,924 B2 | 9/2002 | Jedrzejewski et al. |
| 6,473,492 B2 | 10/2002 | Prins |
| 6,485,913 B1 | 11/2002 | Becker et al. |
| 6,538,823 B2 | 3/2003 | Kroupenkine et al. |
| 6,545,815 B2 | 4/2003 | Kroupenkine et al. |
| 6,565,727 B1 | 5/2003 | Shenderov |
| 6,596,238 B1 | 7/2003 | Belder et al. |
| 6,613,560 B1 | 9/2003 | Tso et al. |
| 6,629,826 B2 | 10/2003 | Yoon et al. |
| 6,665,127 B2 | 12/2003 | Bao et al. |
| 6,761,962 B2 | 7/2004 | Bentsen et al. |
| 6,773,566 B2 | 8/2004 | Shenderov |
| 6,828,100 B1 | 12/2004 | Ronaghi |
| 6,841,128 B2 | 1/2005 | Kambara et al. |
| 6,846,638 B2 | 1/2005 | Shipwash |
| 6,896,855 B1 | 5/2005 | Kohler et al. |
| 6,911,132 B2 | 6/2005 | Pamula et al. |
| 6,924,792 B1 | 8/2005 | Jessop |
| 6,942,776 B2 | 9/2005 | Medoro |
| 6,949,176 B2 | 9/2005 | Vacca et al. |
| 6,958,132 B2 | 10/2005 | Chiou et al. |
| 6,960,437 B2 | 11/2005 | Enzelberger et al. |
| 6,989,234 B2 | 1/2006 | Kolar et al. |
| 7,078,168 B2 | 7/2006 | Sylvan |
| 7,189,359 B2 | 3/2007 | Yuan et al. |
| 7,189,560 B2 | 3/2007 | Kim et al. |
| 7,251,392 B2 | 7/2007 | Kuiper et al. |
| 7,267,752 B2 | 9/2007 | King et al. |
| 7,310,080 B2 | 12/2007 | Jessop |
| 7,439,014 B2 | 10/2008 | Pamula et al. |
| 7,454,988 B2 | 11/2008 | Tan |
| 7,459,311 B2 | 12/2008 | Nyren et al. |
| 7,547,380 B2 | 6/2009 | Velev |
| 7,821,699 B1 | 10/2010 | Lo et al. |
| 2002/0043463 A1 | 4/2002 | Shenderov |
| 2002/0055167 A1 | 5/2002 | Pourahmadi et al. |
| 2002/0058332 A1 | 5/2002 | Quake et al. |
| 2002/0093651 A1 | 7/2002 | Roe |
| 2002/0102595 A1 | 8/2002 | Davis |
| 2002/0125135 A1 | 9/2002 | Derand et al. |
| 2002/0128546 A1 | 9/2002 | Silver |
| 2002/0142483 A1 | 10/2002 | Yao et al. |
| 2002/0168671 A1 | 11/2002 | Burns et al. |
| 2002/0172969 A1 | 11/2002 | Burns et al. |
| 2003/0006140 A1 | 1/2003 | Vacca et al. |
| 2003/0012483 A1 | 1/2003 | Ticknor et al. |
| 2003/0012699 A1 | 1/2003 | Moore et al. |
| 2003/0082081 A1 | 5/2003 | Fouillet et al. |
| 2003/0103021 A1 | 6/2003 | Young et al. |
| 2003/0119057 A1 | 6/2003 | Gascoyne et al. |
| 2003/0164295 A1 | 9/2003 | Sterling |
| 2003/0183525 A1 | 10/2003 | Elrod et al. |
| 2003/0198576 A1 | 10/2003 | Coyne et al. |
| 2003/0205632 A1 | 11/2003 | Kim et al. |
| 2003/0206351 A1 | 11/2003 | Kroupenkine |
| 2003/0224528 A1 | 12/2003 | Chiou et al. |
| 2003/0227100 A1 | 12/2003 | Chandross et al. |
| 2004/0007377 A1 | 1/2004 | Fouillet et al. |
| 2004/0031688 A1 | 2/2004 | Shenderov |
| 2004/0042721 A1 | 3/2004 | Kroupenkine et al. |
| 2004/0055536 A1 | 3/2004 | Kolar et al. |
| 2004/0055891 A1 | 3/2004 | Pamula et al. |
| 2004/0058450 A1 | 3/2004 | Pamula et al. |
| 2004/0091392 A1 | 5/2004 | McBride et al. |
| 2004/0136876 A1 | 7/2004 | Fouillet et al. |
| 2004/0141884 A1 | 7/2004 | Unno et al. |
| 2004/0231987 A1 | 11/2004 | Sterling et al. |
| 2005/0014255 A1 | 1/2005 | Tang et al. |
| 2005/0037507 A1 | 2/2005 | Gauer |
| 2005/0048581 A1 | 3/2005 | Chiu et al. |
| 2005/0056569 A1 | 3/2005 | Yuan et al. |
| 2005/0064423 A1 | 3/2005 | Higuchi et al. |
| 2005/0100675 A1 | 5/2005 | Mao et al. |
| 2005/0106742 A1 | 5/2005 | Wahl |
| 2005/0148042 A1 | 7/2005 | Prestwich et al. |
| 2005/0158755 A1 | 7/2005 | Lee et al. |
| 2005/0179746 A1 | 8/2005 | Roux et al. |
| 2005/0227264 A1 | 10/2005 | Nobile et al. |
| 2005/0260686 A1 | 11/2005 | Watkins et al. |
| 2005/0287572 A1 | 12/2005 | Mathies et al. |
| 2006/0021875 A1 | 2/2006 | Griffith et al. |
| 2006/0039823 A1 | 2/2006 | Yamakawa et al. |
| 2006/0054503 A1 | 3/2006 | Pamula et al. |
| 2006/0068450 A1 | 3/2006 | Combette et al. |
| 2006/0132927 A1 | 6/2006 | Yoon |
| 2006/0166261 A1 | 7/2006 | Higuchi et al. |
| 2006/0166262 A1 | 7/2006 | Higuchi et al. |
| 2006/0172336 A1 | 8/2006 | Higuchi et al. |
| 2006/0254933 A1 | 11/2006 | Adachi et al. |
| 2007/0141593 A1 | 6/2007 | Lee et al. |
| 2007/0243634 A1 | 10/2007 | Pamula et al. |
| 2007/0264723 A1 | 11/2007 | Kim et al. |
| 2007/0275415 A1 | 11/2007 | Srinivasan et al. |
| 2008/0138815 A1 | 6/2008 | Brown et al. |
| 2008/0153091 A1 | 6/2008 | Brown et al. |
| 2008/0160525 A1 | 7/2008 | Brown et al. |
| 2008/0169184 A1 | 7/2008 | Brown et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171382 A1 | 7/2008 | Brown et al. |
| 2008/0213766 A1 | 9/2008 | Brown et al. |

(56) References Cited

U.S. PATENT DOCUMENTS

| | | | |
|---|---|---|---|
| 2009/0042319 A1 | 2/2009 | De Guzman et al. | |
| 2009/0127123 A1 | 5/2009 | Raccurt et al. | |
| 2010/0096266 A1 | 4/2010 | Kim | |

FOREIGN PATENT DOCUMENTS

| | | |
|---|---|---|
| FI | WO9954730 A1 | 10/1999 |
| FR | WO2006003292 A1 | 1/2006 |
| JP | 2006276801 A | 10/2006 |
| US | WO9915876 A1 | 4/1999 |
| US | WO9917093 A1 | 4/1999 |
| US | WO2006026351 A1 | 3/2006 |
| WO | 9822625 A1 | 5/1998 |
| WO | WO03045556 A2 | 6/2003 |
| WO | WO2006026351 A1 | 3/2006 |
| WO | 2007133710 A2 | 11/2007 |
| WO | WO 2008098236 | 8/2008 |
| WO | WO2008098236 A2 | 8/2008 |

OTHER PUBLICATIONS

PCT International Search Report and Written Opinion for PCT/US2006/047481 dated May 5, 2008.

PCT International Search Report and Written Opinion for PCT/US2007/011298 dated Jun. 25, 2008.

PCT International Search Report and Written Opinion for PCT/US2007/009379 dated Aug. 18, 2008.

Ali Agah, "DNA Analysis Chip by Electrowetting Actuation," Stanford Nanofabrication Facility, p. 9, 2002.

Bhansali et al., "Resolving chemical/bio-compatibility issues in microfluidic MEMS systems," SPIE Conference on Microfluidic Devices and Systems II, vol. 3877, Santa Clara, CA, pp. 101-109 (1999).

Cho et al., "Concentration and binary separation of micro particles for droplet-based digital microfluidics," Lab Chip, vol. 7, pp. 490-498, 2007.

Lehmann et al., "Droplet-Based DNA Purification in a Magnetic Lab-on-a-Chip," Angewandte Chemie, vol. 45, pp. 3062-3067, 2006.

N. Pamme, "Magnetism and microfluidics," Lab on a Chip (LOC), vol. 6, pp. 24-38, 2006.

Juergen Pipper et al., "Clockwork PCR Including Sample Preparation," Angew. Chem. Int. Ed., vol. 47, pp. 3900-3904, 2008.

Pollack et al., "Electrowetting-Based Actuation of Droplets for Integrated Microfluidics," Lab on a Chip (LOC), vol. 2, pp. 96-101, 2002.

Olivier Raccurt et al., "On the influence of surfactants in electrowetting systems," J. Micromech. Microeng., vol. 17, pp. 2217-2223 (2007).

Jean-Maxime Roux and Yves Fouillet, "3D droplet displacement in microfluidic systems by electrostatic actuation," Sensors and Actuators A, vol. 134, Issue 2, pp. 486-493, Mar. 15, 2007.

R. Sista, "Development of a Digital Microfluidic Lab-on-a-Chip for Automated Immunoassay with Magnetically Responsive Beads", PhD Thesis, Department of Chemical Engineering, Florida State University, 2007.

T. Taniguchi et al., "Chemical reactions in microdroplets by electrostatic manipulation of droplets in liquid media," Lab on a Chip, vol. 2, No. 2, pp. 19-23 (2002).

Altti Torkkeli, "Droplet microfluidics on a planar surface," Doctoral Dissertation, Department of Electrical Engineering, Helsinki University of Technology (Oct. 3, 2003).

E. Verpoorte, "Beads and chips: new recipes for analysis," Lab on a Chip (LOC), vol. 3, pp. 60N-68N, 2003.

Y. Wang et al., "Effcient in-droplet separation of magnetic particles for digital microfluidics," Journal of Micromechanics and Microengineering, vol. 17, pp. 2148-2156 (2007).

Masao Washizu, "Electrostatic Actuation of Liquid Droplets for Micro-Reactor Applications", IEEE Industry Applications Society Annual Meeting, pp. 1867-1873, Oct. 5-9, 1997.

Wheeler et al., "Electrowetting-on-dielectric for analysis of peptides and proteins by matrix assisted laser desorption/ionization mass spectrometry," Solid-State Sensor, Actuator and Microsystems Workshop publication, pp. 402-403, Jun. 6-10, 2004.

Aaron R. Wheeler, "Putting Electrowetting to Work," Science, vol. 322, No. 5901, pp. 539-540, Oct. 24, 2008.

Yi et al., "Geometric surface modification of nozzles for complete transfer of liquid drops," Solid-State Sensor, Actuator and Microsystems Workshop, pp. 164-167, Jun. 6-10, 2004.

T.H. Zhang, K. Chakrabarty, R.B. Fair, "Behavioral modeling and performance evaluation of microelectrofluidics-based PCR systems using SystemC", IEEE Transactions on Computer-Aided Design of Integrated Circuits & Systems, vol. 23 (6): pp. 843-858, Jun. 2004.

Mohanty et al., "Two Dimensional Micro Gel Electrophoresis Device with Integrated Removeable Capillary Insert (Rci) for Macro-Micro Interface and Post Separation Sample Manipulation," American Electrophoresis Society (AES) Annual Meeting (Nov. 2, 2005).

Kajiyama et al., "Enhancement of Thermostability of Firefly Luciferase from *Luciola lateralis* by a Single Amino Acid Substitution," Biosci. Biotech. Biochem., 58 (6), pp. 1170-1171, 1994.

Nyren et al., "Enzymatic Method for Continuous Monitoring of Inorganic Pyrophosphate Synthesis," Anal. Biochem., vol. 151, Issue 2, pp. 504-509, Dec. 1985.

Taira et al., "Immobilization of Single-Stranded DNA by Self-Assembled Polymer on Gold Substrate for a DNA Chip," Biotechnology and Bioengineering, vol. 89, Issue 7, pp. 835-838, Mar. 30, 2005.

Jie Ding, "System level architectural optimization of semi-reconfigurable microfluidic system," M.S. Thesis, Duke University Dept of Electrical Engineering, 2000.

Shih-Kang Fan, "Digital Microfluidics by Cross-Reference EWOD Actuation: Principle, Device, and System," PhD Dissertation, University of California Dept. of Mechanical Engineering, 2003.

Moon, Hyejin, Ph.D., "Electrowetting-on-dielectric microfluidics: Modeling, physics, and MALDI application," University of California, Los Angeles, 2006.

Mugele et al., "Electrowetting: from basics to applications," Journal of Physics: Condensed Matter, 17, pp. R705-R774 (Jul. 2005).

Dewey A, Srinivasan V, Icoz E, "Visual modeling and design of microelectromechanical system transducers", Microelectronics Journal, vol. 32, pp. 373-381, Apr. 2001.

Dewey A, Srinivasan V, Icoz E, "Towards a visual modeling approach to designing micro electromechanical system transducers," Journal of Micromechanics and Microengineering, vol. 9, pp. 332-340, Dec. 1999.

R.B. Fair, A. Khlystov, T. Tailor, V. Ivanov, R.D. Evans, V. Srinivasan, V. Pamula, M.G. Pollack, P.B. Griffin, and J. Zhoud, "Chemical and Biological Applications of Digital Microfluidic Devices", IEEE Design and Test of Computers, vol. 24(1): pp. 10-24 Jan.-Feb. 2007.

R.B. Fair, A. Khlystov, V. Srinivasan, V. K. Pamula, K.N. Weaver, "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

R.B. Fair, V. Srinivasan, and K.N. Weaver, "Bead-Based and Solution-Based Assays Performed on a Digital Microfluidic Platform," Biomedical Engineering Society (BMES) Fall Meeting, Baltimore, MD, Oct. 1, 2005.

R.B. Fair, V. Srinivasan, H. Ren, P. Paik, V.K. Pamula, M.G. Pollack, "Electrowetting-based On-Chip Sample Processing for Integrated Microfluidics," IEEE Inter. Electron Devices Meeting (IEDM), pp. 32.5.1-32.5.4, 2003.

Phil Paik, Vamsee K. Pamula, and K. Chakrabarty, "Thermal effects on Droplet Transport in Digital Microfluidics with Applications to Chip Cooling Processing for Integrated Microfluidics," International Conference on Thermal, Mechanics, and Thermomechanical Phenomena in Electronic Systems (ITherm), pp. 649-654, 2004.

Phil Paik, Vamsee K. Pamula, and Richard B. Fair, "Rapid droplet mixers for digital microfluidic systems," Lab on a Chip, vol. 3, pp. 253-259, 2003.

Phil Paik, Vamsee K. Pamula, Michael G. Pollack and Richard B. Fair, "Electrowetting-based droplet mixers for microfluidic systems", Lab on a Chip (LOC), vol. 3, pp. 28-33, 2003.

Vamsee K. Pamula and Krishnendu Chakrabarty, "Cooling of integrated circuits using droplet-based microfluidics," Proc. ACM Great Lakes Symposium on VLSI, pp. 84-87, Apr. 2003.

(56) References Cited

OTHER PUBLICATIONS

V.K. Pamula, V. Srinivasan, H. Chakrapani, R.B. Fair, E.J. Toone, "A droplet-based lab-on-a-chip for colorimetric detection of nitroaromatic explosives," Proceedings of Micro Electro Mechanical Systems, pp. 722-725, 2005.

M. G. Pollack, P. Y. Paik, A. D. Shenderov, V. K. Pamula, F. S. Dietrich, and R. B. Fair, "Investigation of electrowetting-based microfluidics for real-time PCR applications," μTAS 2003.

Pollack et al., "Electrowetting-Based Microfluidics for High-Throughput Screening," smallTalk2001 Conference Program Abstract (Aug. 2001), p. 149, San Diego.

Hong Ren, Vijay Srinivasan, Michael G. Pollack, and Richard B. Fair, "Automated electrowetting-based droplet dispensing with good reproducibility," Proc. Micro Total Analysis Systems (mTAS), pp. 993-996, 2003.

Hong Ren, Vijay Srinivasan, and Richard B. Fair, "Design and testing of an interpolating mixing architecture for electrowetting-based droplet-on-chip chemical dilution", Transducers 2003, pp. 619-622, 2003.

Vijay Srinivasan, Vamsee K. Pamula, Richard B. Fair, "An integrated digital microfluidic lab-on-a-chip for clinical diagnostics on human physiological fluids," Lab on a Chip, vol. 4, pp. 310-315, 2004.

Vijay Srinivasan, Vamsee K. Pamula, Richard B. Fair, "Droplet-based microfluidic lab-on-a-chip for glucose detection," Analytica Chimica Acta, vol. 507, No. 1, pp. 145-150, 2004.

V. Srinivasan, V.K. Pamula, P. Paik, and R.B. Fair, "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.

Vijay Srinivasan, Vamsee K. Pamula, Michael G. Pollack, and Richard B. Fair, "Clinical diagnostics on human whole blood, plasma, serum, urine, saliva, sweat, and tears on a digital microfluidic platform," Proc. Micro Total Analysis Systems (mTAS), pp. 1287-1290, 2003.

Vijay Srinivasan, Vamsee K. Pamula, Michael G. Pollack, and Richard B. Fair, "A digital microfluidic biosensor for multianalyte detection", Proc. IEEE 16th Micro Electro Mechanical Systems Conference, pp. 327-330, 2003.

Vijay Srinivasan, Vamsee K. Pamula, K. Divakar Rao, Michael G. Pollack, Joseph A. Izatt, and Richard B. Fair, "3-D imaging of moving droplets for microfluidics using optical coherence tomography," Proc. Micro Total Analysis Systems (mTAS), pp. 1303-1306, 2003.

F. Su, S. Ozev and K. Chakrabarty, "Testing of droplet-based microelectrofluidic systems", Proc. IEEE International Test Conference, pp. 1192-1200, 2003.

Nicole Weaver, "Application of Magnetic Microspheres for Pyrosequencing on a Digital Microfluidic Platform," web publication, Aug. 29, 2005.

"Making materials fit the future: accommodating relentless technological requirements means researchers must recreate and reconfigure materials, frequently challenging established laws of physics, while keeping an eye on Moore's law", R&D Magazine, Dec. 2001.

"Chip mixes droplets faster", MIT Technology Review, Oct. 2003.

"Chip Juggles Droplets", Technology Research News, Sep. 4-11, 2002.

"Laboratory on a Chip", Popular Mechanics, Mar. 2002.

"Lab-on-a-Chip Technology May Present New ESD Challenges", Electrostatic Discharge Journal, Mar. 2002.

U.S. Appl. No. 10/522,175, filed Jan. 24, 2005, entitled "Method and device for screening molecules in cells", which was based on International Application No. PCT/FR2003/002298.

Brady, Kevin, "Electrowetting for DNA Sequencing on Chip," 2004 NNIN REU Research Accomplishments, pp. 26-27.

Lee J, Moon H, Fowler J, et al., "Electrowetting and electrowetting-on-dielectric for microscale liquid handling," Sensors and Actuators A-Physical, vol. 95 (2-3): pp. 259-268, Jan. 1, 2002.

Mugele F, Herminghaus S, "Electrostatic stabilization of fluid microstructures," Applied Physics Letters, vol. 81 (12): pp. 2303-2305, Sep. 16, 2002.

Noderer, W., "DNA pyrosequencing using microfluidic chips," NNIN REU Research Accomplishments, 2005, pp. 96-97.

H. Ren, R. B. Fair, M. G. Pollack, and E. J. Shaughnessy, "Dynamics of electro-wetting droplet transport," Sensors and Actuators B (Chemical), vol. B87, No. 1, pp. 201-206, Nov. 15, 2002.

Schwartz, J.A., J.V. Vykoukal and P.R.C. Gascoyne, "Droplet-based chemistry on a programmable micro-chip," Lab on a Chip, vol. 4, No. 1, pp. 11-17 (2002).

Yoon et al., "Preventing Biomolecular Adsorption in Electrowetting-Based Biofluidic Chips", Analytical Chem. 75, 5097-5102 (2003).

"Geometric Surface Modification of Nozzles for Complete Transfer of Liquid Drops; Ui-Chong Yi et al., Mechanical and Aerospace Engineering Dept., University of California, Los Angeles (UCLA); Solid-State Sensor, Actuator and Microsystems Workshop, Hilton Head Island, South Carolina, Jun. 6-10, 2004; pp. 164-167".

Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.

Tuckerman, D.B. and R.F.W. Pease, "High-Performance Heat Sinking for VLSI, "IEEE Electron Device Letters, 1981, pp. 126-129.

Batchelder, J.S., "Dielectrophoretic manipulator," Review of Scientific Instruments, vol. 54, 1983, pp. 300-302.

Manz, A., N. Graber, and H.M. Widmer, "Miniaturized Total Chemical Analysis Systems: a Novel Concept for Chemical Sensing," Sensors and Actuators B: Chemical, 1990, pp. 244-248.

Welters, W.J.J. and L.G.J. Fokkink, "Fast Electrically Switchable Capillary Effects," Langmuir, vol. 14, Mar. 1998, pp. 1535-1538.

McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.

A. Wego, S. Richter, L. Pagel, "Fluidic microsystems based on printed circuit board technology," Journal of Micromechanics and Microengineering, vol. 11, No. 5, pp. 528-531 (Sep. 2001).

Moon H, Cho SK, Garrell RL, et al., "Low voltage electrowetting-on-dielectric," Journal of Applied Physics, vol. 92 (7): pp. 4080-4087, Oct. 1, 2002.

Locascio, L.E., et al. "Polymer microfluidic devices," Talanta, vol. 56, Feb. 2002, pp. 267-287.

P.Y. Chiou, H. Moon, H. Toshiyoshi, C.-J. Kim, and M.C. Wu, "Light actuation of liquid by optoelectrowetting," Sensors and Actuators A: Physical, vol. 104, May 2003, pp. 222-228.

Squires, T.M. and S.R. Quake, "Microfluidics: Fluid physics at the nanoliter scale," Reviews of Modern Physics, vol. 77, Oct. 2005, pp. 977-1-26.

Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump.," Lab on a chip, vol. 5, Mar. 2005, pp. 12617-12622.

Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.

Cooney, C.G., C-Y. Chen, M.R. Emerling, A Nadim, and J.D. Sterling, Microfluidics and Nanofluidics, vol. 2 Mar. 2006, pp. 435-446.

Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.

M.Madou, J. Zoval, G. Jia, H. Kido, J. Kim, "Lab on a CD," Annual Review of Biomedical Engineering, vol. 8, pp. 601-628, 2006.

Yi, U.-C. and C.-J. Kim, "Characterization of electrowetting actuation on addressable single-side coplanar electrodes," Journal of Micromechanics and Microengineering, vol. 16, Oct. 2006, pp. 2053-2059.

(56) References Cited

OTHER PUBLICATIONS

Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.

Whitesides, G.M., "The origins and the future of microfluidics," Nature, vol. 442, 2006, pp. 368-373.

Chin, C.D., V. Linder, and S.K. Sia, "Lab-on-a-chip devices for global health: past studies and future opportunities.," Lab on a Chip, vol. 7, Jan. 2007, pp. 41-57.

Baviere, R., J. Boutet, and Y. Fouillet, "Dynamics of droplet transport induced by electrowetting actuation," Microfluidics and Nanofluidics, vol. 4, May 2007, pp. 287-294.

Paik, P.Y., V.K. Pamula, and K. Chakrabarty, "A Digital-Microfluidic Approach to Chip Cooling," IEEE Design & Test of Computers, vol. 25, Jul. 2008, pp. 372-381.

The, S. -Y., R. Lin, L.-H. Hung, and A.P. Lee, "Droplet microfluidics.," Lab on a chip, vol. 8 Feb. 2008, pp. 198-220.

I.Barbulovic-Nad, H. Yang, P.S. Park, and A.R. Wheeler, "Digital microfluidics for cell-based assays.," Lab ona chip, vol. 8, Apr. 2008, pp. 519-526.

Huebner, A., S. Sharma, M. Srisa-Art, F. Hollfelder, J.B. Edel, and A.J. DeMello, "Microdroplets: a sea of applications?," Lab on a Chip, vol. 8, Aug. 2008, pp. 1244-1254.

Gong, J. and C.-J.C. Kim, "Direct-referencing two-dimensional-array digital microfluidics using multi-layer printed circuit board," Journal of Microelectromechanical Systems, vol. 17, Jan. 2008, pp. 257-264.

Miller, E.M. and A.R. Wheeler, "A Digital Microfluidic Approach to Homogeneous Enzyme Assays," Analytical Chemistry, vol. 80, 2008, pp. 1614-1619.

R.S. Sista, A.E. Eckhardt, V. Srinivasan, M.G. Pollack, S. Palanki, and V.K. Pamula, "Heterogeneous immunoassays using magnetic beads on a digital microfluidic platform," Lab on a Chip, vol. 8, Dec. 2008, pp. 2188-2196.

R. Sista, Z. Hua, P. Thwar, A Sudarsan, V. Srinivasan, A Eckhardt, M. Pollack, and V. Pamula, "Development of a digital microfluidic platform for point of care testing.," Lab on a chip, vol. 8, Dec. 2008, pp. 2091-2104.

Luk, V.N., Pluronic additives: a solution to sticky problems in digital microfluidics.,: Langmuir: the ACS journal of surfaces ans colloids, vol. 24, Jun. 2008, pp. 6382-6389.

L. Luan, R.D. Evans, N.M. Jokerst, and R.B. Fair, "Integrated Optical Sensor in a Digital Microfluidic Platform," IEEE Sensors Journal, vol. 8, May 2008, pp. 628-635.

R. Mariella, "Sample preparation: the weak link in microfluidics-based biodetection.," Biomedical Microdevices, vol. 10, Dec. 2008, pp. 777-784.

D. Brassard, L. Malic, F. Normandin, M. Tabrizian, and T. Veres, "Water-oil core-shell droplets for electrowetting-based digital microfluidic devices.," Lab on a chip, vol. 8, Aug. 2008, pp. 1342-1349.

R. Mukhopadhyay, "Microfluidics: on the slope of enlightenment.," Analytical chemsitry vol. 81, Jun. 2009, pp. 4169-4173.

N.A. Mousa, M.J. Jebrail, H.Yang, M. Abdelgawad, P. Metalnikov, J. Chen, A.R. Wheeler, and R.F. Casper, "Droplet-scale estrogen assays in breast tissue, blood, and serum.," Science Translational Medicine, vol. 1 Oct. 2009, p. Ira2.

J.L. Poulos, W.C. Nelson, T.-J. Jeon, C.-J. "CJ" Kim, and J.J. Schmidt, "Electrowetting on dielectric-based microfluidics for integrated lipid bilayer formation and measurement," Applied Physics Letters, vol. 95, 2009, p. 013706.

S.M. Langelier, D.S. Chang, R.I. Zeitoun, and M. a Burns, "Acoustically driven programmable liquid motion using resonance cavities" Proceedings of the National Academy of Sciences of the USA, vol. 106, Aug. 2009, pp. 12617-12622.

L. Malic, T. Veres, and M. Tabrizian, "Biochip functionalization using electrowetting-on-dielectric digital microfluidics for surface plasmon resonance imaging detection of DNA hybridization.," Biosensors & Bioelectronics, vol. 24, Mar. 2009, pp. 2218-2224.

G.J. Shah, A.T. Ohta, E.P.-Y. Chiou, M.C. Wu, and C.-J.C.J. Kim, "EWOD-driven droplet microfluidic device integrated with optoelectronic tweezers as an automated platform for cellular isolation and analysis.," Lab on a Chip, vol. 9, Jun. 2009, pp. 1732-1739.

Office Action dated Mar. 26, 2010 from co-pending U.S. Appl. No. 11/639,531.

Response to Office Action dated Mar. 26, 2010 from co-pending U.S. Appl. No. 11/639,531.

Office Action dated Jun. 24, 2010 from co-pending U.S. Appl. No. 11/639,531.

Response to Office Action dated Jul. 14, 2010 from co-pending U.S. Appl. No. 11/639,531.

Advisory Action dated Jul. 28, 2010 from co-pending U.S. Appl. No. 11/639,531.

Response to Office Action dated Aug. 4, 2010 from co-pending U.S. Appl. No. 11/639,531.

Supplemental Response to Office Action dated Aug. 19, 2010 from co-pending U.S. Appl. No. 11/639,531.

Office Action dated Sep. 16, 2010 from co-pending U.S. Appl. No. 11/639,531.

Response to Office Action dated Sep. 13, 2010 from co-pending U.S. Appl. No. 11/639,531.

Office Action dated Oct. 27, 2010 from co-pending U.S. Appl. No. 11/639,531.

Response to Office Action dated Dec. 8, 2010 from co-pending U.S. Appl. No. 11/639,531.

Advisory Action dated Dec. 16, 2010 from co-pending U.S. Appl. No. 11/639,531.

Office Action dated Feb. 17, 2011 from co-pending U.S. Appl. No. 11/639,531.

Office Action dated Apr. 7, 2008 from co-pending U.S. Appl. No. 11/639,736.

Response to Office Action dated Apr. 22, 2008 from co-pending U.S. Appl. No. 11/639,736.

Office Action dated Jul. 22, 2008 from co-pending U.S. Appl. No. 11/639,736.

Response to Office Action dated Jul. 28, 2008 from co-pending U.S. Appl. No. 11/639,736.

Colgate E, Matsumoto H, "An Investigation of Electrowetting-based Microactuation," Journal of Vacuum Science & Technology A-Vacuume Surfaces and Films, V. 8 (4): pp. 3625-3633, Jul.-Aug. 1990.

Pinho, M. et al., Haemopoietic progenitors in the adult mouse omentum: permanent production of B lymphocytes and monocytes. Cell Tissue Res. 2005 Jan. 2005, vol. 319, No. 1, pp. 91-102.

US 8,637,317 B2

METHOD OF WASHING BEADS

RELATED APPLICATIONS

This application is a continuation-in-part of and incorporates by reference U.S. patent application Ser. No. 11/639,531, entitled "Droplet-based washing" filed on Dec. 15, 2006, the application of which claims priority to and incorporates by reference related provisional U.S. Patent Application Nos. 60/745,058, entitled "Filler Fluids for Droplet-Based Microfluidics" filed on Apr. 18, 2006; 60/745,039, entitled "Apparatus and Methods for Droplet-Based Blood Chemistry," filed on Apr. 18, 2006; 60/745,043, entitled "Apparatus and Methods for Droplet-Based PCR," filed on Apr. 18, 2006; 60/745,059, entitled "Apparatus and Methods for Droplet-Based Immunoassay," filed on Apr. 18, 2006; 60/745,914, entitled "Apparatus and Method for Manipulating Droplets with a Predetermined Number of Cells" filed on Apr. 28, 2006; 60/745,950, entitled "Apparatus and Methods of Sample Preparation for a Droplet Microactuator," filed on Apr. 28, 2006; 60/746,797 entitled "Portable Analyzer Using Droplet-Based Microfluidics," filed on May 9, 2006; 60/746,801, entitled "Apparatus and Methods for Droplet-Based Immuno-PCR," filed on May 9, 2006; 60/806,412, entitled "Systems and Methods for Droplet Microactuator Operations," filed on Jun. 30, 2006; and 60/807,104, entitled "Method and Apparatus for Droplet-Based Nucleic Acid Amplification," filed on Jul. 12, 2006.

In addition to the patent applications cited above, this application is a continuation of and incorporates by reference International Patent Application No. PCT/US2009/050101, entitled "Bead Manipulation Techniques" International filing date of Jul. 9, 2009, the application of which claims priority to and incorporates by reference related provisional U.S. Patent Application 61/079,346, entitled "Digital Microfluidic Spacio- and Spectral-Multiplexing of Assays," filed on Jul. 9, 2008; 61/080,731, entitled "Dielectrophoresis on a Droplet Actuator," filed on Jul. 15, 2008; 61/084,637, entitled "Digital Microfluidics Multi-well Droplet Actuator Device and Methods," filed on Jul. 30, 2008; 61/103,302, entitled "Bead Incubation and Washing on a Droplet Actuator," filed on Oct. 7, 2008; 61/108,997, entitled "Adjustable Magnets and Magnetic Fields on a Droplet Actuator," filed on Oct. 28, 2008; 61/122,791, entitled "Bead Incubation and Washing on a Droplet Actuator," filed on Dec. 16, 2008; and 61/149,808, entitled "Droplet-Based Platform for Evaluating Enzymatic Activity," filed on Feb. 4, 2009.

GOVERNMENT INTEREST

This invention was made with government support under CA114993 awarded by the National Institutes of Health. The United States Government has certain rights in the invention.

The foregoing statement applies only to aspects of this disclosure originating in U.S. Patent Application No. 61/084,637, entitled "Digital Microfluidics Multiwell Droplet Actuator Device and Methods," filed on Jul. 30, 2008, U.S. Patent Application No. 61/103,302, entitled "Bead Incubation and Washing on a Droplet Actuator," filed on Oct. 7, 2008, and U.S. Patent Application No. 61/122,791, "Bead Incubation and Washing on a Droplet Actuator," filed on Dec. 16, 2008.

FIELD OF THE INVENTION

The present invention generally relates to bead manipulation techniques. In particular, the present invention is directed to a method of redistributing magnetically responsive beads in a droplet.

BACKGROUND

Droplet actuators are used to conduct a wide variety of droplet operations. A droplet actuator typically includes one or more substrates configured to form a surface or gap for conducting droplet operations. The one or more substrates include electrodes for conducting droplet operations. Liquids that are subjected to droplet operations are typically surrounded by an immiscible filler fluid. When the droplet actuator is configured to form a gap, the gap between the substrates is typically filled or coated with the filler fluid. Droplet operations are controlled by electrodes associated with the one or more substrates. Droplets containing particles, such as beads or cells, may be subjected to various droplet operations on a droplet actuator. Droplets associated with particles may require various methods that may include structures, to be manipulated by the droplet actuator.

Beads, whether or not magnetically responsive have a tendency to settle and form aggregates due to one or more forces that may include gravity, friction, electric and magnetic forces. Aggregation may also occur due to surface interactions between beads or between substances bound to beads or interactions between beads and droplet actuator substrates. Regardless of the causes, aggregation has a direct impact on the performance of assays. Immunoassays for example, has critical time consuming stages like incubation and washing that may be influenced by the aggregation of beads.

During incubation, where interaction of different antibodies and antigens result in binding events, the available surface area on the beads for binding is reduced due to aggregation, thereby impeding reaction kinetics and consequently increasing time to result and/or reducing assay sensitivity. Protocols used for incubation, including but not limited to duration of incubation may be influenced by the mixing efficiency within the droplets and also the reaction and binding kinetics, all of which may be impacted by bead aggregation. When it comes to washing, unwanted unbound substances that are trapped in the interstices of bead aggregates are difficult to separate, remove or wash away, thereby resulting in reduced assay sensitivity. Time to results is impacted if more number of washes are required.

Therefore, there is a need in droplet actuators for resuspending and/or circulating beads within a droplet to break up or loosen up aggregates when required to improve the overall assay performance without having to compromise on sensitivity and the overall time to result.

BRIEF DESCRIPTION OF THE INVENTION

The invention provides a method of redistributing magnetically responsive beads in a droplet. The method may include providing a droplet including magnetically responsive beads. The droplet may be provided within a region of a magnetic field having sufficient strength to attract the magnetically responsive beads to an edge of the droplet or towards an edge of the droplet, or otherwise regionalize or aggregate beads within the droplet. The method may also include conducting on a droplet operations surface one or more droplet operations using the droplet without removing the magnetically responsive beads from the region of the magnetic field. The droplet operations may in some cases be electrode-mediated. The droplet operations may redistribute and/or circulate the magnetically responsive beads within the droplet. In some cases, the droplet may include a sample droplet may include a target analyte. The redistributing of the magnetically responsive beads may cause target analyte to bind to the magnetically responsive beads. In some cases, the droplet may include unbound substances in a wash buffer. The redistributing of the magnetically responsive beads causes unbound substances to be freed from interstices of an aggregated set or subset of the magnetically responsive beads.

In certain embodiments, the droplet operation may be selected to agitate contents of the droplet. The droplet operation may include transporting the droplet. The droplet operation may include elongating the droplet. In some cases, elongating the droplet may include flowing the droplet onto a region of the droplet operations surface atop two or more activated droplet electrodes causing the droplet to take on an elongated configuration. The droplet operation may include merging the droplet with another droplet. The droplet operation may include splitting the droplet to yield two or more daughter droplets. In some cases, two or more of the daughter droplets each may include a substantial subset of the magnetically responsive beads. In some cases, the droplet operation may include merging two or more of the daughter droplets. In some cases, further may include removing the droplet or a sub-droplet thereof including at least a subset of the magnetically responsive beads from the magnetic field. In certain embodiments, one or more droplet operations may be repeated in a series of two or more incubation cycles. The droplet operations surface may be in a droplet operations gap of a droplet actuator. The droplet operations surface may be coated by a liquid filler fluid. The droplet may be surrounded by a liquid filler fluid.

The invention also provides a method of incubating magnetically responsive beads in a droplet. The droplet including magnetically responsive beads may include one or more substances having affinity for one or more of the magnetically responsive beads. The method may include redistributing the magnetically responsive beads in the droplet in accordance with the method of any of the methods described herein.

Further, the invention provides a method of washing magnetically responsive beads in a droplet. The droplet including magnetically responsive beads provided may also include one or more unbound substances selected for removal. The method may include merging the droplet including magnetically responsive beads with a wash droplet to yield a combined droplet. The method may include redistributing the magnetically responsive beads in the droplet in accordance with the method of any of the methods described herein. The method may include splitting the combined droplet to yield a droplet including substantially all of the magnetically responsive beads and a reduced concentration of the unbound substances relative to the starting droplet, and a droplet substantially lacking magnetically responsive beads. The method may be repeated as necessary until a predetermined concentration or quantity of the unbound substances being removed is achieved.

In another method of washing magnetically responsive beads in a droplet, the method may include merging the droplet with magnetically responsive beads with a wash droplet in the magnetic field to yield a combined droplet and to redistribute the magnetically responsive beads within the combined droplet, and splitting the combined droplet to yield a droplet including substantially all of the magnetically responsive beads and a reduced concentration of the unbound substances relative to the starting droplet, and a supernatant droplet substantially lacking magnetically responsive beads.

In another method of washing magnetically responsive beads in a droplet, the method may include conducting one or more droplet operations using the droplet in the magnetic field to redistribute the magnetically responsive beads in the droplet in accordance with any of the other methods described herein, and merging the droplet including the redistributed magnetically responsive beads with a wash droplet to yield a combined droplet. Further, the method may include splitting the combined droplet to yield a first daughter droplet including substantially all of the magnetically responsive beads and a reduced concentration of the unbound substances relative to the starting droplet, and a second daughter droplet substantially lacking magnetically responsive beads.

The invention provides a method of redistributing magnetically responsive beads in a droplet, which method may include providing a droplet including magnetically responsive beads within a first region of a magnetic field having sufficient strength to attract the magnetically responsive beads to an edge of the droplet, and using electrodes to transport droplet to a second region of a droplet operations surface in which the magnetic field may be sufficiently reduced to permit the magnetically responsive beads to circulate in the droplet during the conduct of one or more droplet operations. The method may also include conducting the one or more droplet operations to cause the magnetically responsive beads to circulate in the droplet. In some cases, in the second region of the droplet operations surface, the beads are substantially free from the influence of the magnetic field. In some embodiments, at least a subset of the beads in the starting droplet are magnetically aggregated. The droplet may include a sample droplet including a target analyte. Circulation of the magnetically responsive beads may cause target analyte to bind to the magnetically responsive beads. In some cases, the droplet may include unbound substances in a wash buffer. In some cases, the circulation of the magnetically responsive beads causes disaggregation of an aggregated set or subset of the magnetically responsive beads freeing of unbound substances from interstices of the aggregated set or subset of the magnetically responsive beads. The one or more droplet operations may be selected to agitate contents of the droplet. The one or more droplet operations may include transporting the droplet. The one or more droplet operations may include elongating the droplet. In some cases, elongating the droplet may include flowing the droplet onto a region of the droplet operations surface atop two or more activated droplet electrodes causing the droplet to take on an elongated configuration. The droplet operation may include merging the droplet with another droplet. The droplet operation may include splitting the droplet to yield two or more daughter droplets. In some cases, two or more of the daughter droplets each may include a substantial subset of the magnetically responsive beads. The droplet operation may include merging two or more of these daughter droplets. One or more droplet operations may be repeated in a series of two or more incubation cycles. The droplet operations surface may be in a droplet operations gap of a droplet actuator. The droplet operations surface may be coated by a liquid filler fluid. The droplet may be surrounded by a liquid filler fluid.

In another method of incubating magnetically responsive beads in a droplet may include merging the droplet including magnetically responsive beads with a wash droplet to yield a combined droplet, redistributing the magnetically responsive beads in the combined droplet in accordance with the method of any of the methods described herein, and reintroducing the magnetically responsive beads into the first region of the magnetic field or into a region of another magnetic field having sufficient strength to attract the magnetically responsive beads to an edge of the droplet. In yet another method of washing magnetically responsive beads in a droplet, the method may include redistributing the magnetically responsive beads in the droplet in accordance with the method of any of the methods described herein and reintroducing the magnetically responsive beads into the first region of the magnetic field or into a region of another magnetic field having sufficient strength to attract the magnetically responsive beads to an edge of the droplet. These methods may also include splitting the combined droplet to yield a droplet including substantially all of the magnetically responsive beads and a reduced concentration of the unbound substances relative to the starting droplet, and a droplet substantially lacking magnetically responsive beads.

The invention also provides a method of incubating a droplet, including providing a droplet including magnetically responsive beads within a region of a magnetic field in which the magnetically responsive beads are caused to become aggregated; using electrodes to conduct on a droplet operations surface droplet operations using the droplet wherein the droplet operations may include: one or more droplet operations transporting the droplet away from the magnetic field to a locus of the droplet operations surface in which the magnetically responsive beads are resuspended in the droplet; and one or more droplet operations effecting an incubation cycle in the locus in which the magnetically responsive beads are resuspended in the droplet.

Further, the invention provides a method of washing beads in a droplet, including providing an elongated bead-containing droplet may include one or more unbound substances; providing an elongated wash droplet; restraining movement of beads within the elongated bead-containing droplet; merging end-to-end the elongated bead-containing droplet with the elongated bead containing droplet to yield a combined droplet; and splitting the combined droplet to form a droplet including substantially all of the beads and a droplet substantially lacking in beads. In some cases, restraining movement of beads within the elongated bead containing droplet may include restraining the beads in an end region of the elongated bead containing droplet. The method may also include conducting a resuspension cycle using the bead-containing droplet prior to conducting the merging step. Restraining movement of beads may be accomplished by providing the elongated bead-containing droplet in a magnetic field having a field strength which is sufficient to restrain movement of the beads. In some cases, merging end-to-end the elongated bead-containing droplet with the elongated bead containing droplet causes circulation within the combined droplet which redistributes the beads. In some cases, the restraining, merging and splitting steps are completed in less than about 30 seconds, or less than about 15 seconds, or less than about 10 seconds, or less than about 5 seconds.

The invention provides another method of washing beads, including providing the beads in a sample droplet may include a target substance on a droplet operations substrate within a magnetic field; transporting the sample droplet away from the beads, causing the droplet to split, yielding a supernatant droplet and leaving behind a daughter droplet including substantially all of the magnetically responsive beads; and subjecting the daughter droplet to a merge-and-split bead washing protocol. In some cases, the supernatant droplet includes more than 50% of the unbound substances being removed. In some cases, the supernatant droplet includes more than 75% of the unbound substances being removed.

The steps of any of the washing processes described herein may be repeated until the unbound substances selected for removal from the droplet are reduced by a predetermined amount. In some cases, the predetermined amount will be at least about 99%, or at least about 99.9%, or at least about 99.99%, or at least about 99.999%. The predetermined reduction may in some cases be achieved in 15 or fewer wash cycles, or 10 or fewer wash cycles, or 5 or fewer wash cycles. Further, the predetermined reduction may be achieved while retaining substantially all of the beads. In some cases, at least about 99.9% of the beads are retained, or at least about 99.99% of the beads are retained, or at least about 99.999% of the beads are retained.

The invention also provides a method of removing beads from a region of a magnetic field. The method may include providing a droplet including the beads in a region of the magnetic field in which the beads are aggregated by the magnetic field; elongating the droplet; transporting the droplet away from the region of the magnetic field in which the beads are aggregated out of the magnetic field or into a region of the magnetic field which may be sufficiently weak that the beads become disaggregated within the droplet. The droplet may be provided on a droplet operations surface of a droplet actuator. Elongating the droplet may include activating one or more electrodes to cause the droplet to take on an elongated conformation atop a droplet operations surface of a droplet actuator. In some cases, the droplet operations surface may be situated in a droplet operations gap of the droplet actuator. In certain embodiments, the transporting may include electrowetting-mediated droplet transporting. In certain embodiments, the transporting may include transporting the droplet away from the region of the magnetic field in a direction which follows an approximately lengthwise axis of the droplet.

The invention also provides a method of multiplexing detection in an assay. The method may include providing a set of two or more detection-ready droplets. Each droplet may include two or more sets of assay products. Each set of assay products may include a unique optical marker, such as a color-based marker. The method may include spectrally analyzing each of the two or more droplets to quantify the assay products. In some cases, no single droplet includes the same unique optical marker for two different analytes. In certain embodiments, two different droplets may include the same unique optical marker for two different analytes, one of such analytes in each of the droplets. The spectrally analyzing step may make use of a multi-channel spectral analyzer. The multi-channel spectral analyzer may include an excitation light source arranged to direct light in an excitation spectra into each of the droplets. The multi-channel spectral analyzer may include a electromagnetic radiation sensing device arranged to sense electromagnetic radiation emitted from the droplets. In certain embodiments, each droplet may include four or more sets of assay products, or ten or more sets of assay products. In certain embodiments, the method may include providing a set of five or more of the detection-ready droplets, or set of 25 or more of the detection-ready droplets, or a set of 50 or more of the detection-ready droplets. In certain embodiments, the unique optical marker may include a quantum dot marker. In some cases, the quantum dot marker may include a core material coated with a high bandgap material. In some cases, method may be executed on a fluorescing background substrate, and the quantum dot markers fluoresce at an excitation wavelength which differs from the excitation wavelength of the fluorescing background substrate. In some cases, assay products are bound to fluorescing beads, and the quantum dot markers fluoresce at an excitation wavelength which differs from the excitation wavelength of the fluorescing beads. In some cases, the method may be executed on a fluorescing background substrate, and the quantum dot markers fluoresce at an emission wavelength which differs from the emission wavelength of the fluorescing background substrate. In some cases, assay products are bound to fluorescing beads, and the quantum dot markers fluoresce at an emission wavelength which differs from the emission wavelength of the fluorescing beads. In certain embodiments, the assay products may include products of a droplet-based assay, such as a droplet-based immunoassay. In certain embodiments, the assay products may include products of a droplet-based assay executed on a droplet actuator. In certain embodiments, the assay products may include products of a droplet-based assay, and the detection-ready droplet has a volume which may be less than about 1000 nL, or less than about 500 nL. In certain embodiments, detection-ready droplets are substantially surrounded by a liquid filler fluid. In some cases, the liquid filler fluid may include an oil filler fluid. In certain embodiments, detection-ready droplets are sandwiched between two substrates. The method may also include analyzing light from each droplet to identify and/or quantify assay products. In some cases, analyzing light from each droplet may include dispersing the light from each droplet along a dispersion axis. In some cases, analyzing light from each droplet may include separately binning light from each droplet to provide a spectrum for each droplet. In some cases, analyzing light from each droplet may include using filters to isolate signals from each droplet.

The invention provides a droplet actuator with a first substrate including a droplet operations surface, electrodes arranged for conducting one or more droplet operations on the surface, and one or more dielectrophoresis electrode configurations arranged for attracting and/or trapping one or more particles in a droplet situated on the droplet operations surface. In some cases, the droplet actuator may include a second substrate separated from the droplet operations surface to form a droplet operations gap. In some cases, the one or more dielectrophoresis electrode configurations may include at least one dielectrophoresis electrode configuration mounted on the second substrate. The dielectrophoresis electrode configurations may include at least one quadripole electrode configuration. In some cases, the quadripole electrode configuration may include four opposing triangular electrodes arranged to form a particle capture zone. In some cases, the four opposing triangular electrodes are symmetrical. In some cases, the four opposing triangular electrodes may include one or more asymmetrical electrodes. In some cases, the quadripole electrode configuration may include four wires terminating at a particle capture zone. The dielectrophoresis electrode configurations may include at least one configuration may include two electrodes the two electrodes may include opposing fringed regions separated by a gap. The dielectrophoresis electrode configurations may include at least one configuration may include multiple triangular electrodes arranged to form a particle trap zone. The dielectrophoresis electrode configuration doubles as a droplet operations electrode. The dielectrophoresis electrode configuration may include a travelling wave configuration.

The invention also provides a method of dispensing a droplet, including providing on a droplet operations surface a first droplet may include a first concentration of particles subject to dielectrophoretic forces, localizing the particles in a region of the first droplet, and conducting an electrowetting-driven droplet dispensing operation yielding a second droplet may include a second concentration of the particles, wherein the second concentration may be greater than the first concentration, and a third droplet may include a third concentration may include a third concentration of the particles, wherein the third concentration may be less than the first concentration.

DEFINITIONS

As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, dyed microparticles and nanoparticles, magnetic microparticles and nanoparticles, superparamagnetic microparticles and nanoparticles (e.g., DYNABEADS® particles, available from Invitrogen Corp., Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in in U.S. Patent Publication No. 20050260686, entitled, "Multiplex flow assays preferably with magnetic particles as solid phase," published on Nov. 24, 2005, the entire disclosure of which is incorporated herein by reference for its teaching concerning magnetically responsive materials and beads. Beads may be pre-coupled with a biomolecule (ligand). The ligand may, for example, be an antibody, protein or antigen, DNA/RNA probe or any other molecule with an affinity for the desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/

058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. The beads may include one or more populations of biological cells adhered thereto. In some cases, the biological cells are a substantially pure population. In other cases, the biological cells include different cell populations, e.g., cell populations which interact with one another.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic liquid, serum, plasma, sweat, tear, saliva, sputum, cerebrospinal liquid, amniotic liquid, seminal liquid, vaginal excretion, serous liquid, synovial liquid, pericardial liquid, peritoneal liquid, pleural liquid, transudates, exudates, cystic liquid, bile, urine, gastric liquid, intestinal liquid, fecal samples, liquids including single or multiple cells, liquids including organelles, fluidized tissues, fluidized organisms, liquids including multicelled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006; and Roux et al., U.S. Patent Pub. No. 20050179746, entitled "Device for Controlling the Displacement of a Drop Between two or Several Solid Substrates," published on Aug. 18, 2005; the disclosures of which are incorporated herein by reference. Certain droplet actuators will include a substrate, droplet operations electrodes associated with the substrate, one or more dielectric and/or hydrophobic layers atop the substrate and/or electrodes forming a droplet operations surface, and optionally, a top substrate separated from the droplet operations surface by a gap. One or more reference electrodes may be provided on the top and/or bottom substrates and/or in the gap. In various embodiments, the manipulation of droplets by a droplet actuator may be electrode mediated, e.g., electrowetting mediated or dielectrophoresis mediated or Coulombic force mediated. Examples of other methods of controlling liquid flow that may be used in the droplet actuators of the invention include devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed in droplet actuators of the invention.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles.

"Filler fluid" means a liquid associated with a droplet operations substrate of a droplet actuator, which liquid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; International Patent Application No. PCT/US2008/072604, entitled "Use of additives for enhancing droplet actuation," filed on Aug. 8, 2008; and U.S. Patent Publication No. 20080283414, entitled "Electrowetting Devices," filed on May 17, 2007; the entire disclosures of which are incorporated herein by reference. The filler fluid may fill the entire gap of the droplet actuator or may coat one or more surfaces of the droplet actuator. Filler fluid may be conductive or non-conductive. Filler fluid may also be a wax-like material that can be melted at elevated temperatures to fill the entire chip.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials, such as, for example, DYNABEADS® MYONE™ beads. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP. The magnetic field may be produced by any magnetic field generating device which is suitable for causing the intended effect. Examples of magnetic field generating devices include permanent magnets and electromagnets. The product of the field magnitude and the gradient generate the force on magnetically responsive beads. In configuring systems of the invention, the field magnitude or gradient may be altered as needed to achieve a desired result. In some cases, a combination of electromagnet plus rare earth magnet may be used to manipulate magnetically responsive beads.

"Washing" with respect to washing a bead means reducing the amount and/or concentration of one or more substances in contact with the magnetically responsive bead or exposed to the magnetically responsive bead from a droplet in contact with the magnetically responsive bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference. The unbound substances being removed from the liquid surrounding the beads The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

DESCRIPTION

Figure 1:
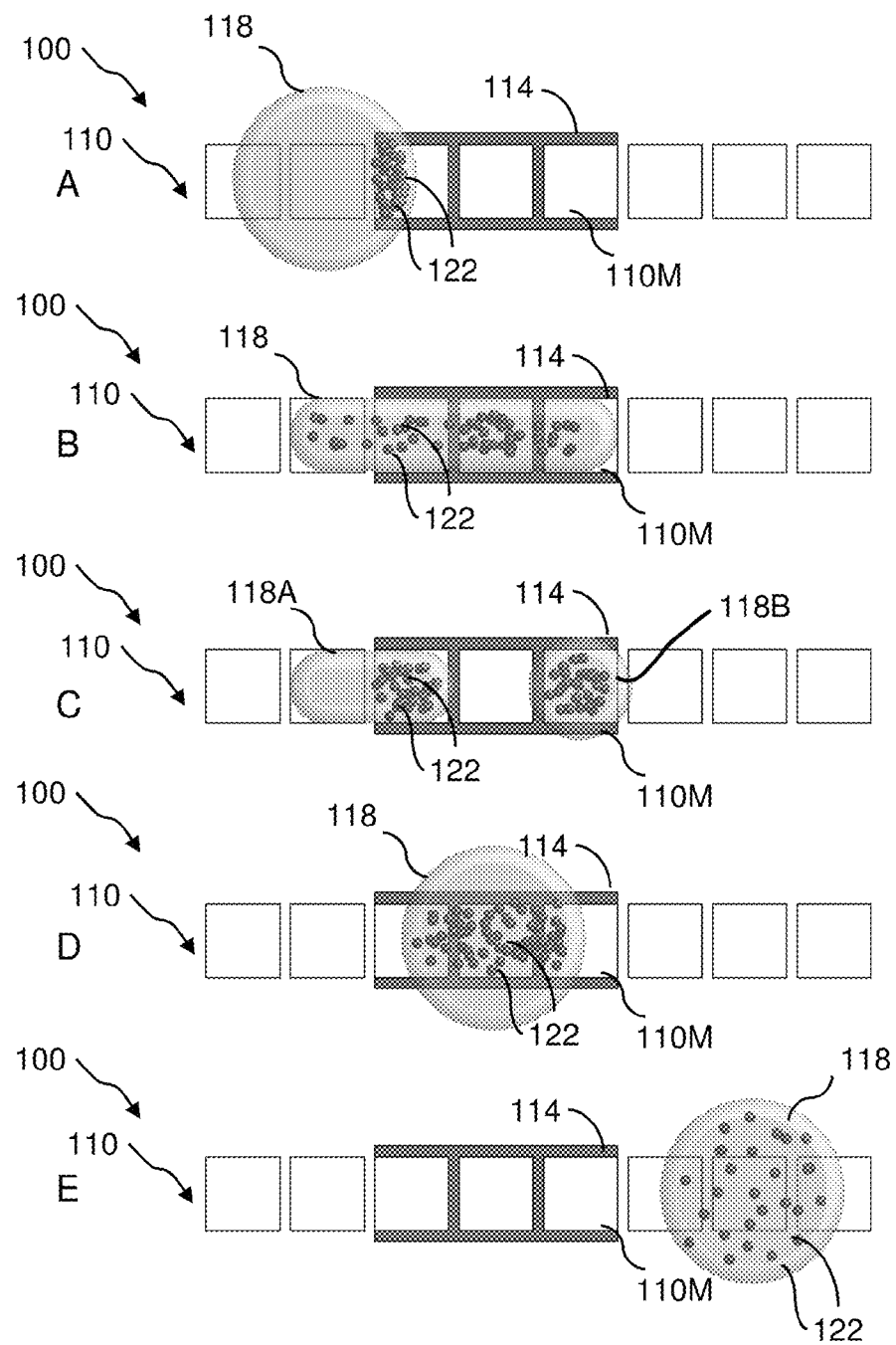
FIGS. 1A-1E illustrate top views of an electrode/magnet arrangement of a droplet actuator and a process of incubating droplets including magnetically responsive beads.

The invention provides devices and methods for resuspending or circulating beads in a bead-containing droplet on a droplet actuator. During an incubation or washing protocol, for example, a bead-containing droplet may be subjected to one or more droplet operations to resuspend or circulate beads within the droplet. These droplet operations may, for example, be mediated by electrowetting or other electric field mediated phenomena. Suitable droplet operations may be selected to improve reaction kinetics, such as by agitating, redistributing, and or circulating droplet contents and/or controlling droplet temperature. Redistribution or circulation of beads within a droplet may increase binding of a target analyte to the beads and/or free up unbound substances from within magnetically aggregated beads.

8.1 Bead Incubation and Washing

Magnetically responsive beads have a tendency to settle and form aggregates due to gravity and/or exposure to magnetic forces. Non-magnetically responsive beads may also aggregate due to surface interactions between beads or between substances bound to beads. Aggregation reduces the available surface area for binding and slows reaction kinetics, increasing time to result and/or reducing assay sensitivity. Interstices in magnetically responsive bead aggregates can also hold unbound substances. These trapped substances may be difficult or impossible to separate from the beads during washing processes, reducing sensitivity of assay results. The invention provides techniques for circulating or mixing beads within a droplet to overcome these issues. The invention also provides incubation protocols that make use of these recirculation techniques for improving binding of molecules to the magnetically responsive beads. Moreover, the invention provides washing protocols that make use of these recirculation techniques for removing unbound molecules from the magnetically responsive beads.

8.1.1 Incubation Protocols

As observed above, beads in a droplet on a droplet actuator are subject to bead aggregation issues. These bead-containing droplets may be provided on a droplet operations surface of a droplet actuator. The droplet operations surface may, in some cases, be provided within a droplet operations gap of a droplet actuator. The droplet may be partially or substantially completely surrounded by a filler fluid. The droplet may be provided in a reservoir associated with a droplet actuator. The reservoir may be in fluid communication with a liquid path configured for transporting liquid from the reservoir onto a droplet operations surface of a droplet actuator. Here again, the droplet operations surface may, in some cases, be provided within a droplet operations gap of a droplet actuator.

The bead-containing droplet may be subjected to bead resuspension protocols on the droplet actuator. During an incubation or washing protocol, for example, the bead-containing droplet may be subjected to one or more droplet operations to resuspend or circulate beads within the droplet. These droplet operations may, for example, be mediated by electrowetting or other electric field mediated phenomena. Suitable droplet operations may be selected to improve reaction kinetics, such as by agitating, redistributing, and or circulating droplet contents and/or controlling droplet temperature. Redistribution or circulation of beads within a droplet may increase binding of a target analyte to the beads and/or free up unbound substances from within magnetically aggregated beads.

Droplet transport is an example of a droplet operation selected to redistribute or circulate beads within a droplet. During transport from electrode-to-electrode, contents of the bead-containing are circulated and redistributed within the droplet. Other examples of droplet operations suitable for enhancing incubation or washing include splitting and merging droplet operations. Any combination of droplet operations may be used. Multiple droplet operations may be combined to provide a complete incubation cycle (e.g., transport-split-merge, transport-split-transport-merge-transport). Incubation cycles may be repeated any number of times to achieve a desired result, such as a desired degree of mixing of beads with contents of the droplet.

The incubated droplet may include any suitable components that require incubation. For example, the droplet may include reagents and/or sample for conducting an immunoassay. A droplet including beads having a binding affinity for an analyte may be subjected to one or more incubation cycles to improve binding of the analyte to the beads. Beads bound to an analyte may be subjected to one or more incubation cycles in a droplet with secondary antibody to improve binding of the secondary antibody to the target. In another case, the magnetic beads already containing the sample of interest can be incubated with an elution buffer to elute the sample bound to the beads and transport it to further processing. In that case, the beads would be transported to waste reservoir after eluting off the sample. It should also be noted that incubation cycles may be used to enhance the kinetics of chemical reactions even in droplets where beads are not present. As another example, a droplet including cells and reagents for supplying one or more metabolic requirements of the cells may be subjected to one or more incubation cycles to improve supply of the metabolic reagent to the cells. In some cases, the cells may be bound to beads. In another embodiment, the incubation can be between a chemiluminescence or fluorescence producing reagent with an enzyme on an immuno-complex bound to magnetic beads. Effective resuspension of magnetic beads by incubating the enzyme labeled magnetic beads would improve the sensitivity of the assay.

FIGS. 1A-1E illustrate top views of an electrode/magnet arrangement 100 of a droplet actuator and a process of incubating droplets including magnetically responsive beads. Arrangement 100 shows a path of electrodes 110. Droplet 118 is positioned in a droplet operations gap (not shown) or on a droplet operations surface where droplet 118 is subject to droplet operations mediated by electrodes 110. Droplet 118 includes magnetically responsive beads. Magnet 114 is provided in proximity to electrodes 110M. Electrodes 110M are a subset of electrodes 110. Magnet 114 is positioned relative to electrodes 110M such that when droplet 118 is atop one or more of electrodes 110M, magnetically responsive beads 122 within droplet 118 are attracted by the magnetic field of magnet 114. Alternatively, magnet 114 is positioned relative to electrodes 110M such that when droplet 118 is subject to droplet operations mediated by electrodes 110M, magnetically responsive beads 122 within droplet 118 are attracted by the magnetic field of magnet 114. The attraction of magnetically responsive beads 122 may cause beads 122 to move within droplet 118 in the direction of magnet 114. Magnetically responsive beads 122 may move towards an edge of droplet 118 which is proximate magnet 114. The parameters of the configuration may be adjusted such that beads 122 are attracted towards an edge of droplet 118 without exiting droplet 118. In this and other examples described herein which make use of magnetically responsive beads and magnets, the technique may be optimized by adjusting properties such as interfacial tension of droplet 118, properties and concentration of magnetically responsive beads 122, and the pull force of exerted by magnet 114 on magnetically responsive beads 122. The incubation technique shown in FIG. 1 illustrates the use of droplet operations to redistribute magnetically responsive beads 122 within droplet 118. One or more of the droplet operations may be conducted while the magnetically responsive beads 122 are being influenced or attracted by the magnetic field of magnet 114. Droplet 118 may be subjected to droplet operations mediated by electrodes 110M while magnetically responsive beads 122 within droplet 118 are being attracted to magnet 114. For example, droplet 118 may be transported along electrodes 110M by using electrodes 110M to create an electrowetting effect on a droplet operations surface.

In FIG. 1A, droplet 118 including beads 122 is positioned adjacent to and overlapping droplet operations electrodes 110M. Magnetically responsive beads 122 are attracted by the magnetic field of magnet 114, causing a concentration of beads to form at the edge of droplet 118 that is closest to magnet 114. In FIG. 1B, droplet 118 is transported to and elongated along several electrodes 110M using droplet operations mediated at least in part by electrodes 110M. In this manner, droplet 118 is caused to conform to an elongated geometry. The transformation of droplet 118 from a rounded configuration to an elongated configuration produces a flow of liquid within droplet 118 that redistributes beads 122 in droplet 118 allowing interaction of the beads with several parts of the droplet more effectively. In FIG. 1C, elongated droplet 118 is split using droplet operations to form daughter droplets 118A, 118B. Two daughter droplets 118A, 118B are illustrated here, but any number of daughter droplets may be formed within the scope of the invention. Splitting of droplet 118 redistributes beads 122 within the daughter droplets 118A, 118B. In FIG. 1D, daughter droplets 118A,118B are merged using droplet operations mediated by electrodes 110M to reform droplet 118. This merging is accomplished while beads 122 are being attracted by the magnetic field of magnet 114. The transporting, elongation, splitting, and merging operations of FIGS. 1B, 1C, and 1D are one example of an incubation cycle. Multiple incubation cycles may be performed to provide for resuspension and/or redistribution (i.e., mixing) of beads 122 of droplet 118, e.g., during incubation and/or washing of droplet 118. In FIG. 1E, droplet 118 is transported away from magnet 114 using droplet operations to adjacent electrodes 110. Droplet 118 may, for example, be transported a distance from magnet 114 sufficient to reduce or substantially eliminate the attractive force of the magnetic field of magnet 114 on magnetically responsive beads 122. For example, the magnetic force may be sufficiently reduced to permit beads 122 to be resuspended in droplet 118. Also, the droplet can be transported at higher switching speeds allowing very little time for the magnetic beads to get attracted. Higher droplet switching speeds would enable better binding efficiency of the analyte onto the magnetic beads thereby requiring lesser incubation time. In this case the magnet is right underneath the droplet containing magnetic beads, there is a higher chance of aggregation of beads since the magnetic beads are always under the effect of magnetic field gradient at every step of incubation. This effect would be more pronounced in cases of longer incubation times or multiple steps of incubation resulting in clumps of beads. However, incubation of the beads right over the magnet would be useful when the real estate available is very little and the sensitivity requirements are not as stringent, wherein the typical dynamic range of the analyte concentration is 1 ng/mL to 100 ng/mL and the incubation times are in the range of 30 seconds to 300 seconds.

FIGS. 2A-2E show the electrode/magnet arrangement 100 of FIG. 1 and a different process of incubating droplets including magnetically responsive beads. FIG. 2 illustrates removal of magnetically responsive beads 122 from the attraction of the magnetic field of magnet 114, followed by execution of an incubation cycle. At a sufficient distance from magnet 114, any attractive force exerted by the magnetic field may be sufficiently reduced to permit beads 122 to be resuspended and distributed within droplet 118, as illustrated in FIGS. 2B-2E. A series of droplet operations, such as split and merge droplet operations, may be used to agitate and mix beads 122 within the droplet 118 after droplet 118 has transported a sufficient distance from magnet 114 to permit resuspension of beads 122. In this case, since the droplet is incubated away from the magnet surface, the maximum magnetic field gradient is experienced only when the droplet is at position 2A. However this can also be alleviated by transporting the droplet at higher switching speeds allowing very little time for the magnetic beads to settle and get influenced by the magnetic field gradient.

In FIG. 2A, droplet 118 with beads 122 is positioned adjacent to droplet operations electrodes 110M, such that beads 122 are attracted by the magnetic field of magnet 114. A concentration of magnetically responsive beads 122 is formed at an edge of droplet 118 that is closest to magnet 114. In FIG. 2B, droplet 118 is transported using electrode mediated droplet operations away from magnet 114 and repositioned at a distance sufficient to permit resuspension of beads 122 in droplet 118. FIGS. 2C, 2D, and 2E show droplet elongation (i.e., formation of slug-shaped geometry), droplet splitting, and droplet merging, respectively. The incubation cycle cause spatial reorientation of the liquid of droplet 118 and redistribution of beads 122 within droplet 118.

FIGS. 3A-3C show the electrode/magnet arrangement 100 of FIG. 1 and illustrate a process of incubating droplets by transporting droplets back and forth. The incubation steps take place at a distance from the magnetic field of magnet 114 which is sufficient to permit the magnetically responsive beads 122 remain suspended within droplet 118 during incubation. A series of droplet transport operations are used to resuspend the beads within the droplet. Droplet 118 is transported using droplet operations along a path of droplet operation electrodes 110. The transporting steps agitate the liquid in droplet 118 and cause redistribution of magnetically responsive beads 122 within droplet 118. This kind of incubation sequence would allow for higher switching speeds than the sequences described earlier. Since there is a split-merge operation in the two incubation sequences (FIGS. 1 and 2), the switching speed is limited since at higher speeds, the droplets would not merge effectively. So, shuttling the droplet with no split-merge operation at higher speeds would achieve the same incubation efficiency.

Figure 4:
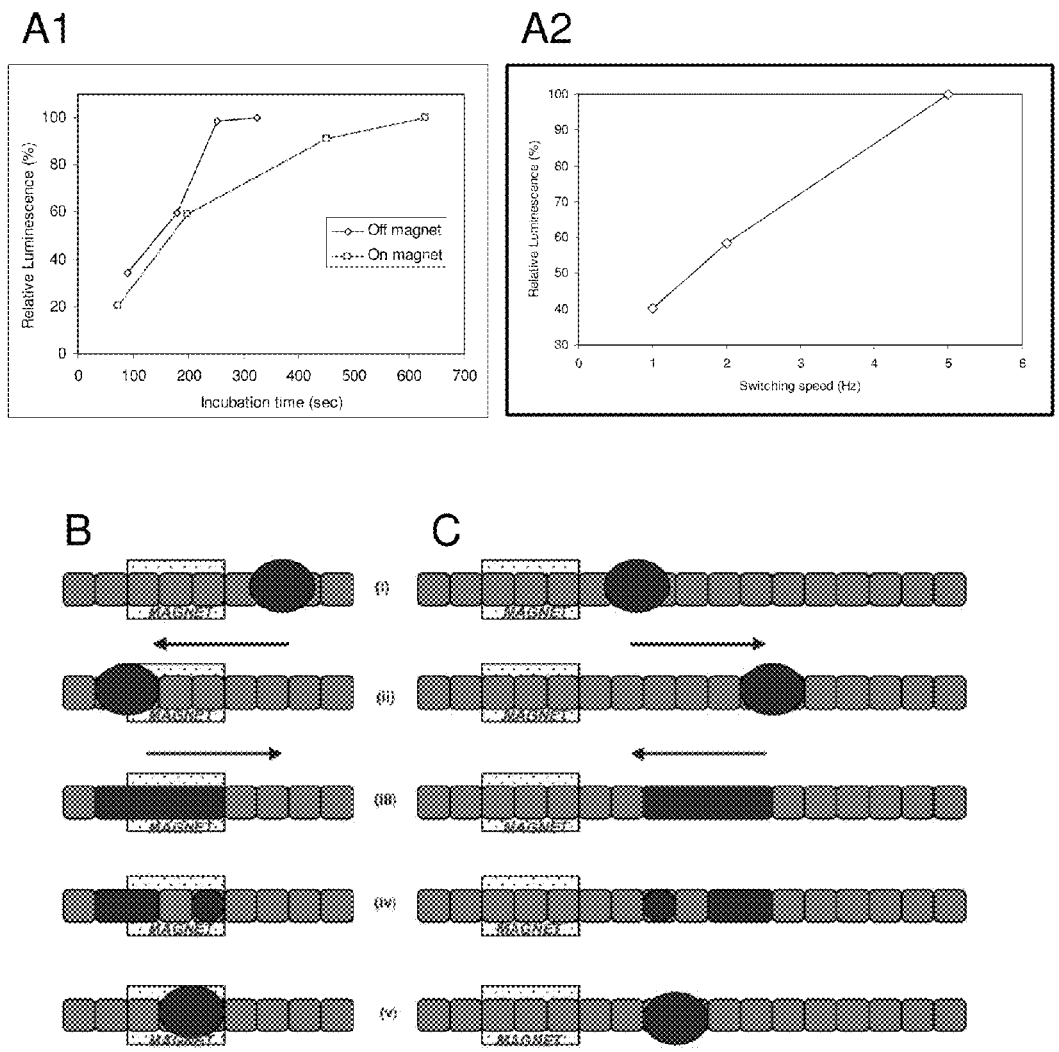
FIGS. 4A-C show the results of work comparing incubation time between on-magnet and off-magnet incubation protocols for an immunoassay.

FIGS. 4A-C show the results of work comparing incubation time between on-magnet and off-magnet incubation protocols for an immunoassay. Results are measured in chemiluminescence. The sequence of droplet operations in the incubation protocol involved shuttling the droplet along a linear path of electrodes with a splitting and merging step inserted between transport cycles. Immunoassays were performed on a 300 nL droplet that contained 5 ng/mL TnI as a model assay using two different incubation protocols, among many other possibilities, with one performed on-magnet as shown in FIG. 4B and the other off-magnet as shown in FIG. 4C. The first incubation protocol was performed by shuttling a merged droplet (sample droplet, capture antibody conjugated magnetic beads droplet and ALP-labeled reporter antibody droplet) across a set of seven electrodes (Steps i and ii in FIG. 4B) followed by a split and merge sequence performed at the center of the magnet (Steps iii, iv and v in FIG. 4B) so that the beads were about equally distributed between the split droplets. Since the droplets were transported at a switching frequency of 1 Hz, it takes 18 seconds for the droplets to complete one incubation cycle. Several such incubation cycles are repeated to obtain the required incubation time as a multiple of 18 seconds. In the second incubation protocol, the sequence of droplet operations and the number of electrodes used for incubation is the same but the only difference is that it is performed away from the magnet (the nearest the droplet gets to the magnet is two electrode widths—FIG. 4C(iii). Immunoassays were performed using both the incubation protocols with varying incubation times and a plot of incubation time versus signal was obtained for both the incubation protocols, as shown in FIG. 4A1. Time-to-saturation in the on-magnet incubation protocol was double that of the off-magnet protocol. The difference in time-to-saturation may occur because of the relatively greater recirculation of beads in the off-magnet protocol. Off-magnet incubation circulates the magnetically responsive beads in both the lateral (X-Y) and vertical (Z direction) dimensions.

In certain point of care applications, where the size of the droplet actuator and thereby the real estate on the droplet actuator is restricted, incubation might need to be performed on the magnet which will take about 10 minutes if 100% antigen has to be captured leaving only 5 minutes for all other operations within the time to result budget of 15 minutes. Therefore, in such a case, incubation may be performed only for 5 minutes but still capturing 80% of the antigen. On the other hand, if real estate is not an issue and if a few more electrodes off-magnet could be utilized for incubation, then 100% of the antigen can be captured within 4 minutes. The same effect of off-magnet incubation could also be obtained by mechanically moving the magnet away from the droplet actuator.

Figure 2:
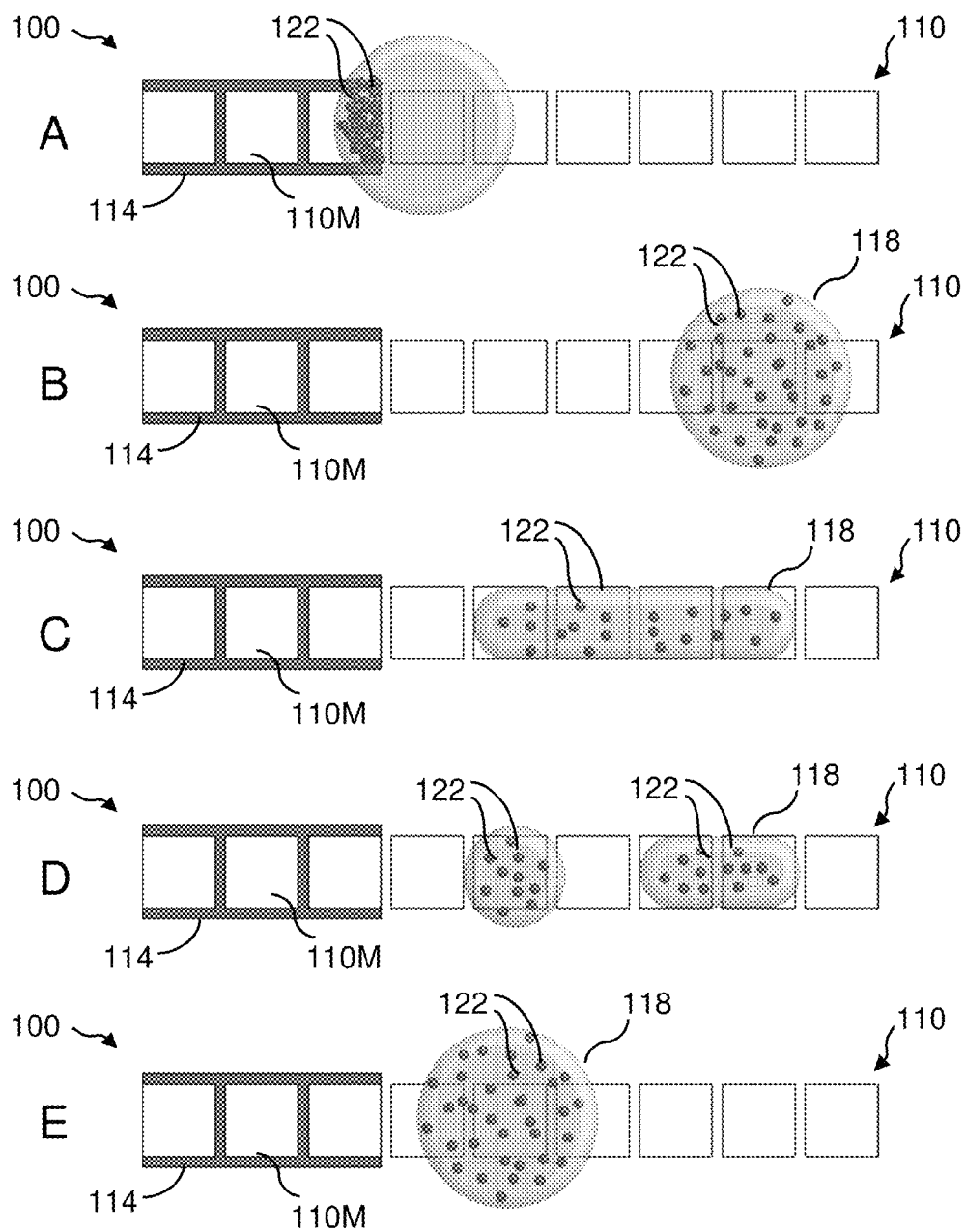
FIGS. 2A-2E show the electrode/magnet arrangement of FIG. 1 and a different process of incubating droplets including magnetically responsive beads.
Figure 3:
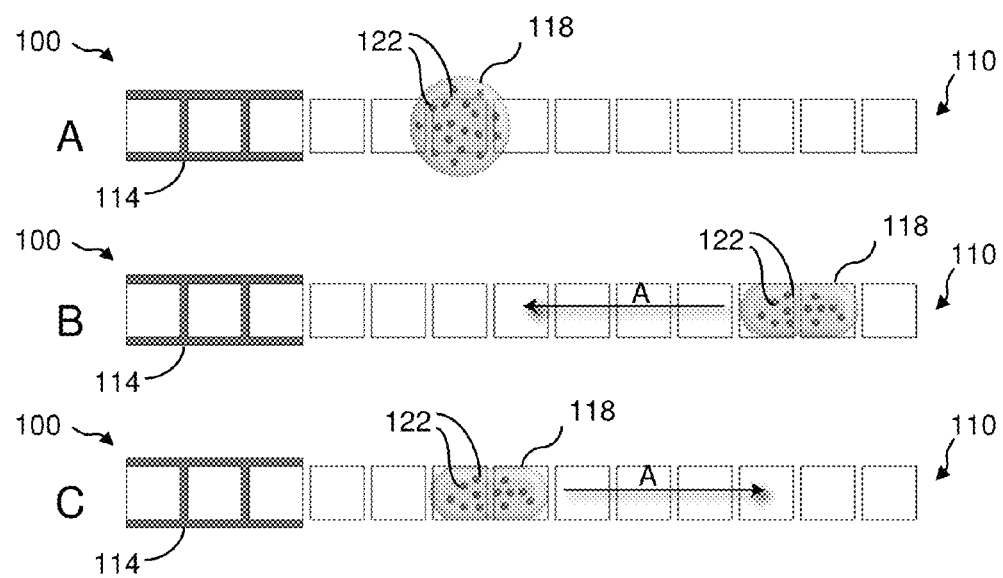
FIGS. 3A-3C show the electrode/magnet arrangement of FIG. 1 and illustrate a process of incubating droplets by transporting droplets back and forth.

FIG. 4A2 shows the result of work comparing the signal obtained by using different switching speeds while incubating the droplet using the sequence described in FIG. 3. Results were measured in chemiluminescence. Immunoassays were performed on a 600 nL droplet that contained 10 pg/mL of Tumor necrosis factor-α (TnF-α). The sequence of droplet operations in the incubation protocol involved shuttling the droplet along a linear path of electrodes with no split-merge operation as shown in FIG. 3. Effect of switching speed on the signal obtained was studied by performing the immunoassay using different switching speeds at the same incubation time. Since the total incubation time was fixed, the droplets had to be oscillated for a larger number of cycles at higher switching speeds in order to maintain the same total incubation time.

8.1.2 Washing Protocols

The invention provides washing protocols for removing unbound molecules from the magnetically responsive beads. The input to a washing protocol is a bead-containing droplet including unbound substances, and the output is typically a bead-containing droplet in which the concentration and/or quantity of these unbound substances is reduced relative to the concentration and/or quantity present in the input droplet.

Washing is thus a critical step in the implementation of many assay protocols. In some embodiments, washing is performed using a merge-and-split wash protocol. A merge-and-split wash protocol generally involves merging a bead-containing droplet with a wash droplet and then splitting off a supernatant droplet which carries away at least a portion of the unbound substances. In some cases, an initial droplet is subjected to one or more splitting steps prior to the initial wash droplet merge step. Droplet splitting steps are typically performed in the presence of a magnet, so that the split yields one or more bead-containing droplets in which the concentration and/or quantity of unbound substances is reduced relative to the concentration and/or quantity present in prior to the split and one or more droplets without a substantial amount of beads wherein the concentration and/or quantity of unbound substances is increased relative to the concentration and/or quantity present prior to the split. Bead retention is important, particularly when the process involves multiple wash cycles, each cycle may potentially reduce the number of retained beads. The washing steps may be repeated as needed until the unbound substances are sufficiently depleted from the liquid surrounding the beads. In some cases, the unbound substances are substantially or completely depleted from the liquid surrounding the beads.

FIGS. 5A-5E illustrate top views of an electrode/magnet arrangement 500 of a droplet actuator (not shown) and a process of washing magnetically responsive beads. Wash buffer droplet 516 and magnetically responsive bead droplet 514 are elongated. A series of merge and split operations are used to remove unbound material from liquid surrounding the beads. The merge and split operations may provide for substantially complete replacement of liquid in droplet 514 surrounding beads 522 in the bead droplet. Thus, substantially all unbound supernatant in droplet 514 may be replaced with wash buffer from droplets 516 during the washing operation.

Figure 5:
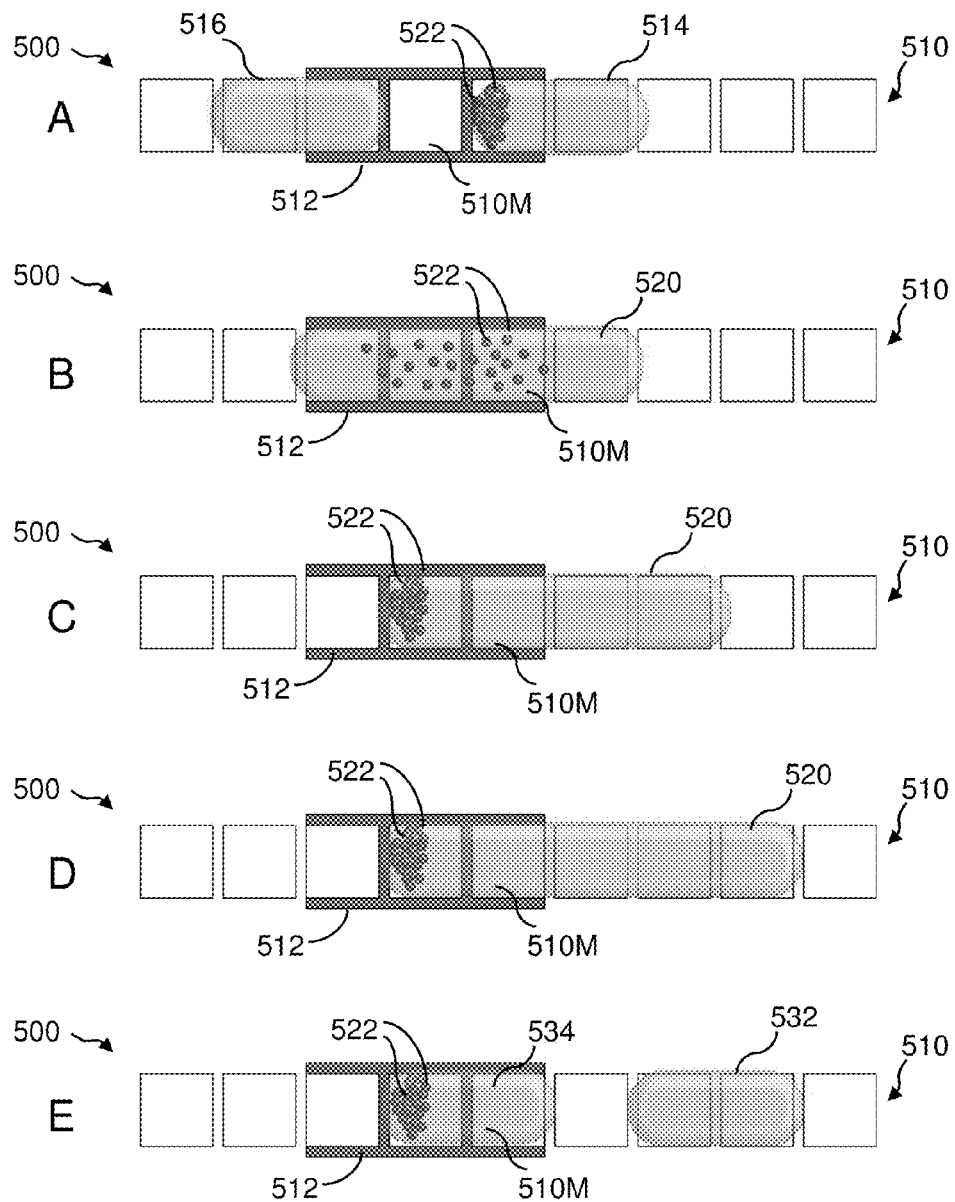
FIGS. 5A-5E illustrate top views of an electrode/magnet arrangement of a droplet actuator (not shown) and a process of washing magnetically responsive beads.

Electrode/magnet arrangement 500 may include an arrangement (e.g., a path or array) of droplet operations electrodes 510. Droplets 514 and 516 are positioned in a droplet operations gap (not shown) or on a droplet operations surface where droplets 514 and 516 are subject to droplet operations mediated by electrodes 510. Droplet 514 includes magnetically responsive beads 522. Magnet 512 is provided in proximity to electrodes 510M. Electrodes 510M are a subset of electrodes 510. Magnet 512 is positioned relative to electrodes 510M such that when droplet 514 is atop one or more of electrodes 510M, magnetically responsive beads 522 within droplet 514 are attracted by the magnetic field of magnet 512. Alternatively, magnet 512 is positioned relative to electrodes 510M such that when droplet 514 is subject to droplet operations mediated by electrodes 510M, magnetically responsive beads 522 within droplet 514 are attracted by the magnetic field of magnet 512. The attraction of magnetically responsive beads 522 may cause beads 522 to move within droplet 514 in the direction of magnet 512. Magnetically responsive beads 522 may move towards an edge of droplet 514 which is proximate to magnet 512. The parameters of the configuration may be adjusted such that beads 522 are attracted towards an edge of droplet 514 without exiting droplet 514. In this and other examples described herein which make use of magnetically responsive beads and magnets, the technique may be optimized by adjusting properties such as interfacial tension of droplets 514 and 516, properties and concentration of magnetically responsive beads 522, and the pull force of exerted by magnet 512 on magnetically responsive beads 522. The size, strength, orientation relative to beads, and number of magnets may also be varied for the purpose of optimization. The washing technique shown in FIG. 5 illustrates the use of droplet operations to redistribute magnetically responsive beads 522 within droplet 514 during the droplet washing operation. One or more of the droplet operations may be conducted while the magnetically responsive beads 522 are being influenced or attracted by the magnetic field of magnet 512. Droplet 514 may be subjected to droplet operations mediated by electrodes 510M while magnetically responsive beads 522 within droplet 514 are being attracted to magnet 512. For example, droplet 514 may be transported along electrodes 510M by using electrodes 510M to create an electrowetting effect on a droplet operations surface.

Droplet 516 may include a wash buffer. Droplet 514 may include magnetically responsive beads 522. Bead droplet 514 and wash buffer droplet 516 may, for example, be 2× droplets, meaning that their footprint is approximately 2 times the area of one droplet operations electrode 510. Bead droplet 514 and wash buffer droplet 516 may be configured as slug-shaped droplets (i.e., elongated droplets) by performing droplet operations on the 2× droplets using two underlying active droplet operations electrodes 510. Because the excess droplet volume is now spread over a second active droplet operations electrode 510, the droplets are elongated and conform to the shape of two electrodes.

FIG. 5A shows bead droplet 514 that has beads 522 therein positioned such that beads 522 are attracted by the magnetic field of magnet 512. A concentration of beads is formed at the edge of bead droplet 514 that is closest to magnet 512. FIG. 5B shows bead droplet 514 and buffer droplet 516 are merged to form merged droplet 520 while beads 522 remain under the attractive influence of magnet 512. Merging of bead droplet 514 and wash droplet 516 provides flow patterns within the merged droplet 520 that redistribute beads 522. FIGS. 5C and 5D show elongation of droplet 520 in distally relative to magnet 512 and beads 522. Elongation may be achieved by activating the contiguous droplet operations electrodes 510. As droplet 520 is extended, beads 522 remain concentrated on magnet 512. FIG. 5E shows droplet 520 split using droplet operations to form supernatant droplet 532 and washed bead droplet 534. Supernatant droplet 532 includes unbound particles and reagents, such as unbound reporter antibody and sample contaminants, from bead droplet 514. Supernatant droplet 532 is typically discarded in a waste reservoir (not shown) or transported into another process, e.g., into contact with a different bead set for capturing a different target from the sample. FIGS. 5A through 5E show an example of a set of droplet operations that comprise a wash cycle. Several wash cycles may be performed to provide for sufficient removal of unbound material.

The wash cycle may yield a bead-containing droplet having a decreased quantity or substantially decreased quantity of an unwanted substance or substances relative to the starting concentration of the unwanted substance or substances. The resulting droplet may in some embodiments have a volume which is approximately the same as the starting volume. In some embodiments, the wash cycle may be repeated until a predetermined maximum quantity of the one or more components is met or exceeded in the resulting droplet. The predetermined amount may represent a substantial reduction relative to the starting concentration. In some cases, the resulting droplet may be substantially free of the unwanted substance. For example, in some embodiments, the reduction in amount of the unwanted substance exceeds 99, 99.9. 99.99, 99.999, 99.9999, 99.99999, 99.999999 percent on a molar basis.

Generally, each wash cycle results in retention of sufficient beads for conducting the intended assay without unduly detrimental effects on the results of the assay. In certain embodiments, each execution of a wash cycle results in retention of more than 99, 99.9. 99.99, 99.999, 99.9999, 99.99999, or 99.999999 percent of beads. In still other embodiments, the amount of retained beads is calculated and the results are adjusted accordingly.

In some cases, the wash cycle is repeated until the reduction in amount of the unwanted substance exceeds 99, 99.9. 99.99, 99.999, 99.9999, 99.99999, 99.999999 percent on a molar basis and more than 99, 99.9. 99.99, 99.999, 99.9999, 99.99999, or 99.999999 percent of beads is retained.

Figure 6:
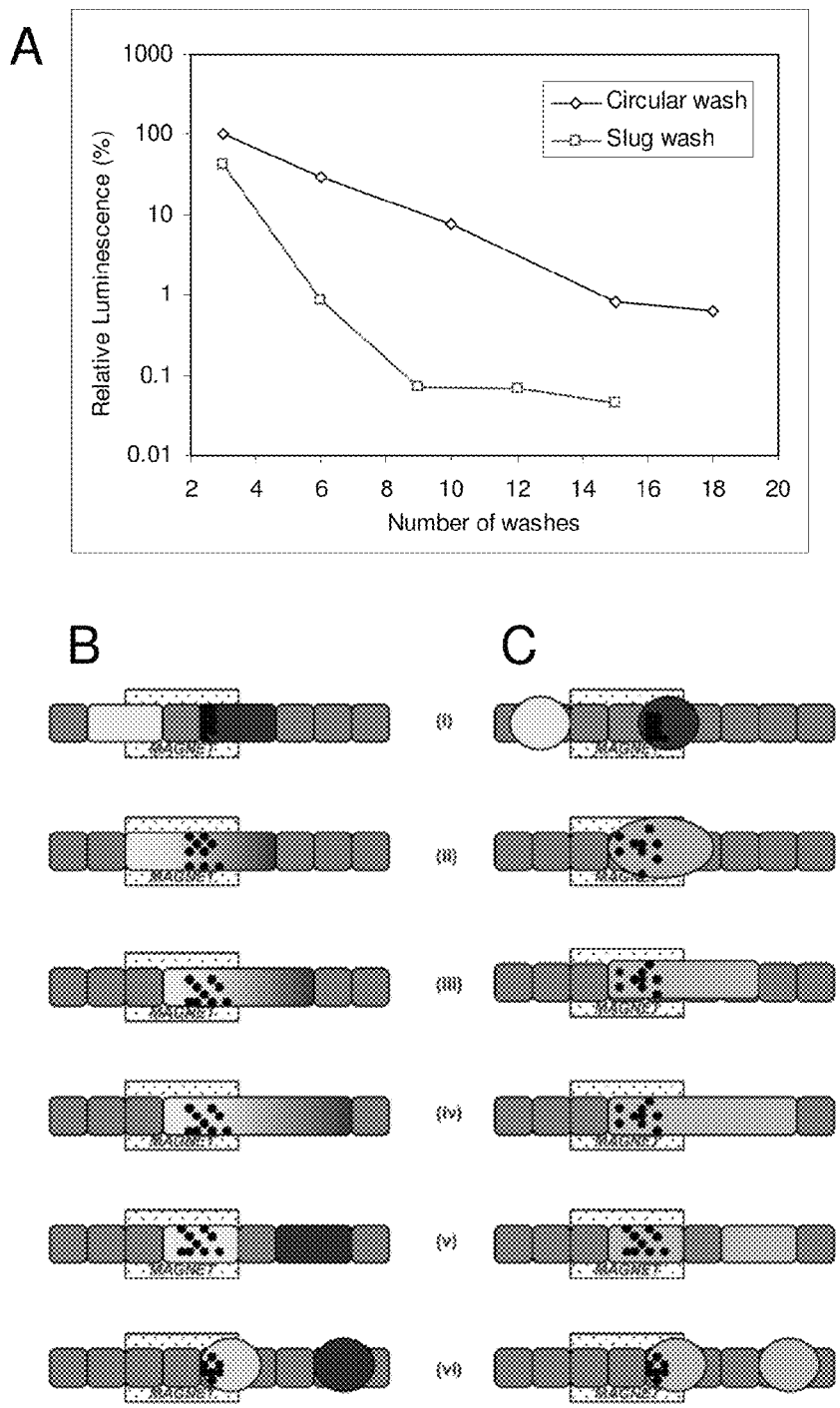
FIGS. 6A-6C show a comparison of washing protocols between slug shaped and circular shaped wash droplets on immunoassay performance measured in chemiluminescence.

FIGS. 6A-6C show a comparison of washing protocols between slug shaped and circular shaped wash droplets on immunoassay performance measured in chemiluminescence. While incubation benefits greatly from higher mixing efficiency, washing by serial dilution benefits from no-mixing or low-mixing conditions. Ideally, the wash droplet should maximize dilution of the liquid surrounding the beads and minimize dilution of the supernatant that is carrying away the unbound substances. Immunoassays were tested using only two wash protocols to determine the optimum washing protocol required to achieve a total time to result of <15 minutes. Immunoassays were performed on a 300 nL droplet containing 0 ng/mL TnI using either an elongated droplet or a circular droplet. 0 ng/mL TnI was chosen for this study because this sample would have the greatest amount of unbound reporter antibodies that must be removed during washing. Schematics of the washing protocols for the elongated and circular cases are shown in FIGS. 6B and 6C, respectively. In the first washing protocol, the wash buffer droplet and the magnetic bead droplet are less rounded or circular and more elongated, which was achieved by operating on the 2× droplets using two electrodes each. By activating two electrodes, the 2× droplet conforms to the shape of two electrodes as illustrated in FIG. 6A. Even though the two protocols in FIGS. 6B(vi) and 6C(vi) appear similar, the effect of washing, as depicted by the shading, is quite different. The second washing protocol involves merging the wash droplet with the magnetic bead droplet where the shape of the droplets is circular or almost circular as shown in FIG. 6B. The circular shape of the droplet is obtained by operating on a 2× (denotes two unit droplets) droplet using only one electrode.

The magnetic bead droplets were washed with varying numbers of wash cycles using the two wash protocols described above, and the chemiluminescence was read with a PMT after adding the chemiluminescence reagent. A plot of number of wash cycles versus the chemiluminescent signal was obtained for both the washing protocols, as illustrated in FIG. 6A. Wash cycles may typically range from about 2 to about 30 seconds. The time for each wash cycle generally depends on the distance a wash droplet has to travel from the wash reservoir to the magnetic beads en route to the waste reservoir, transport speed of the droplets, dispensing and disposal rates of the droplets.

Since washing on droplet actuator involves several dilution steps, the time to result can be seriously affected when several wash cycles are required to achieve the desired wash efficiency. FIG. 6A shows the chemiluminescence signal obtained from an immunoassay after the droplets were subjected to different numbers of wash cycles and different wash protocols. In both the cases presented herein, incubation was performed using the off-magnet incubation protocol for 3 minutes. Each wash cycle takes about 8-10 seconds in the slug-based protocol and 8-14 seconds in the circular droplet protocol. It can be seen from FIG. 6A, that when washing was performed using slugs of liquid (or elongated droplets as shown in FIG. 6C) desired wash levels were achieved using fewer wash cycles when compared to washing using circular shaped droplets. In the former, mixing was minimized and the bulk of the unbound material from the supernatant was replaced with fresh wash buffer, whereas in the latter mixing was facilitated by operating the 2× droplets using only one electrode each. The shading used in FIGS. 6B and 6C depict the situation achieved by operating the 2× droplet using two electrodes and one electrode respectively. Also, it was observed visually that the dispersion of magnetic beads in the lateral plane was higher in the elongated droplet washing when the fresh wash buffer droplet merged with the magnetic bead droplet. This would enable the breaking up of aggregates and any unbound antibody trapped in the interstices to diffuse into the supernatant and be washed away instantly or in subsequent washes. Hence desired wash levels were achieved in ~10 washes using elongated droplet washing, as compared to >18 washes in the rounded droplet washing. The washing behavior has two distinct regimes, one regime where washing is very pronounced and the second where the washing is more subtle. In the slug based washing case, the washing is pronounced with each wash cycle up to 9 cycles, after which the effect of washing is almost subtle or negligible. In the rounded droplet protocol, the washing effect is pronounced until the 15th wash, although the step wash efficiency is less than that observed for the slug-based protocol. Washing is only marginally effective for the circular droplet protocol between the 15th and $18^{th}$ cycles. This may occur because the free unbound material may be washed away in the first few cycles, after which washing only removes the unbound material trapped between the beads. Removal of substances trapped between the beads may be improved by including resuspension cycles in the wash protocol.

Figure 7:
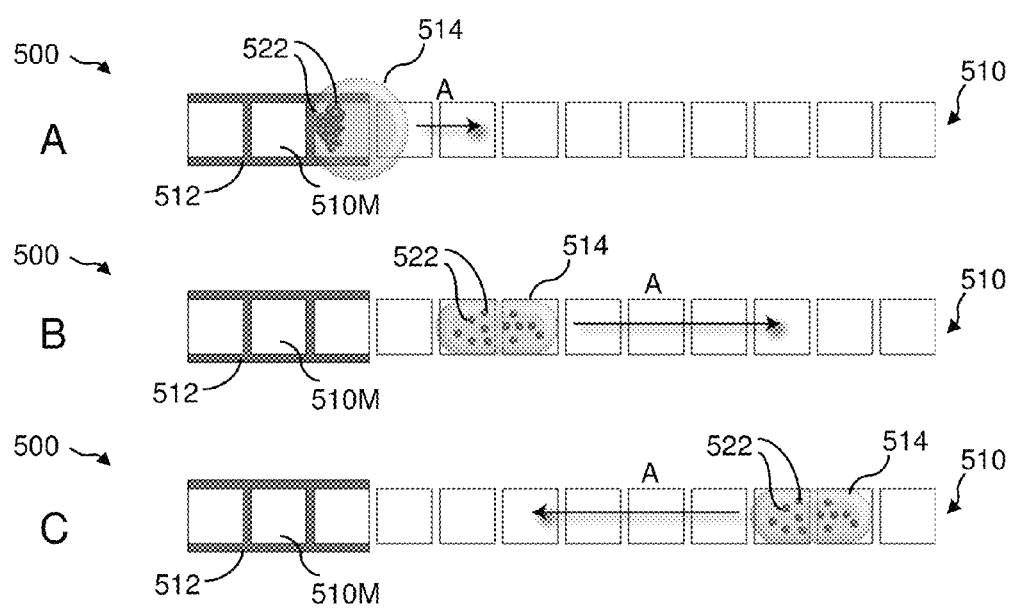
FIGS. 7A-7C illustrate top views of the electrode/magnet arrangement of FIG. 5 and show a process of resuspending magnetically responsive beads during a wash protocol.

FIGS. 7A-7C illustrate top views of the electrode/magnet arrangement 500 of FIG. 5 and show a process of resuspending magnetically responsive beads during a wash protocol. Droplet resuspension cycles are used to resuspend the magnetically responsive beads during or between wash cycles to free material that would otherwise remain trapped in interstices of bead aggregates. FIG. 7A shows bead droplet 514 that includes magnetically responsive beads 522 being transported using droplet operations away from magnet 512 in the direction of arrow A. FIGS. 7B and 7C show transporting of bead droplet 514 along a path of droplet operation electrodes 510 in the direction of arrow A. Two transport operations are shown in FIGS. 7B and 7C, but any number of transport operations may be used to comprise a resuspension cycle. Transporting of bead droplet 514 provides for sufficient resuspension of beads 522 such that unbound material from the interstices of bead aggregates may be effectively removed in subsequent wash cycles. Other droplet operations, such as merging and splitting, or rounding and elongating, may be included in the resuspension cycle.

A complete wash protocol may include a series of wash cycles, such as the slug based wash cycles of FIG. 5, interspersed with a one or more resuspension cycles. Depending on the sensitivity of the assay required and the time to result requirement, any number of wash cycles may be interspersed with any number of resuspension cycles. For example, a complete wash protocol sequence may include, for example, four wash cycles, four resuspension cycles, and four wash cycles.

Figure 8A:
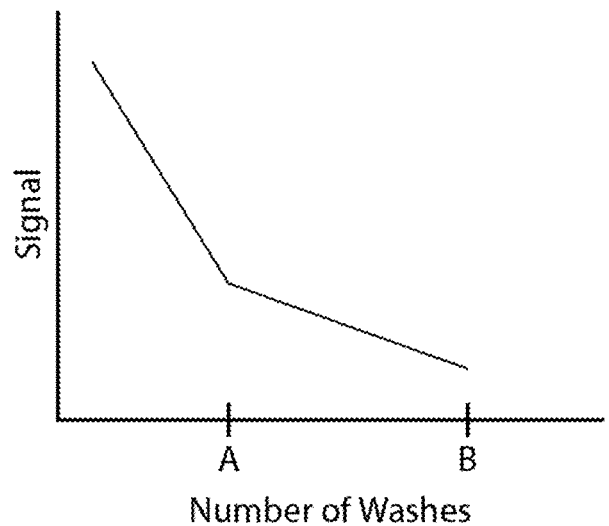
FIGS. 8A and 8B show plots comparing the results of washing without resuspension cycles and with resuspension cycles, respectively.
Figure 8B:
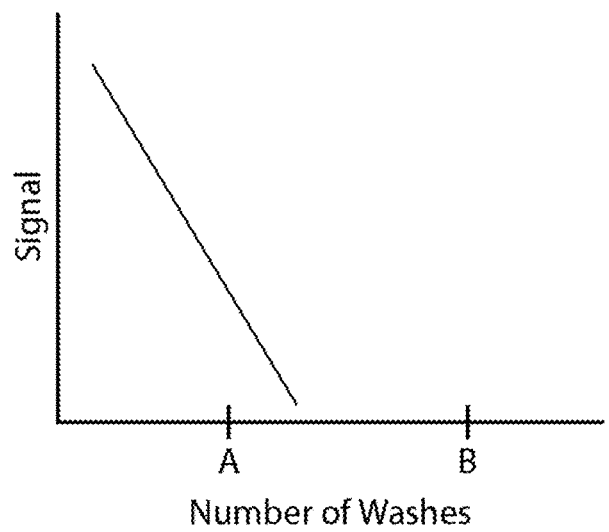

FIGS. 8A and 8B show plots comparing the results of washing without resuspension cycles and with resuspension cycles, respectively. FIG. 8A illustrates that a washing protocol in the absence of one or more resuspension cycles provides an initial drop in signal after a number of wash cycles (A). As the number of wash cycles increase (B), there is a further reduction in signal that may be due to loss of unbound material from the interstices of bead aggregates. FIG. 8B illustrates that a washing protocol including resuspension cycles provides more efficient removal of unbound material to a near zero level using fewer numbers of wash cycles (A).

Figure 9:
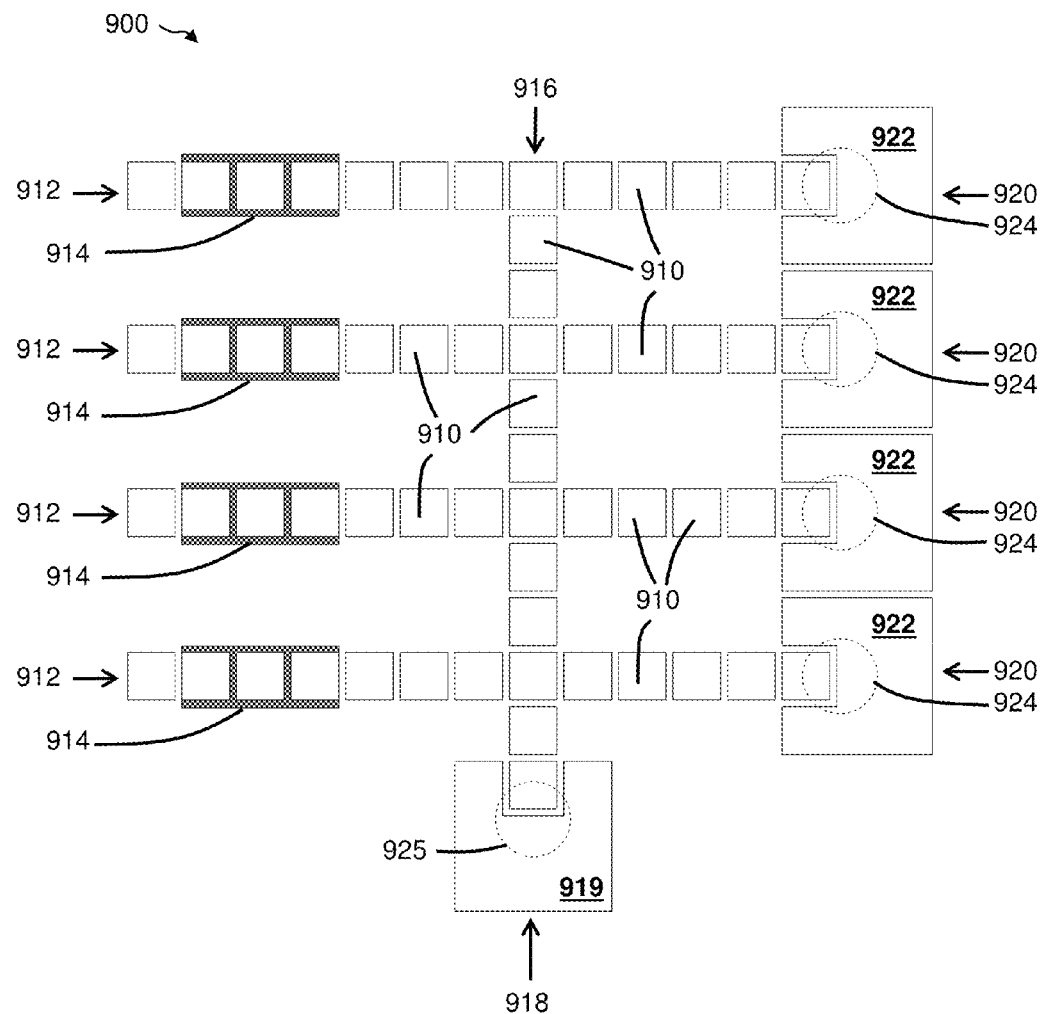
FIG. 9 illustrates a top view of an electrode/magnet arrangement on a droplet actuator configured for efficient washing.

FIG. 9 illustrates a top view of an electrode/magnet arrangement 900 on a droplet actuator configured for efficient washing. Droplet actuator 900 includes an arrangement of droplet operations electrodes 910. Electrodes 910 are arranged to provide wash lanes 912 and waste lane 916. Wash lanes 912 are associated with magnets 914 arranged to permit a droplet to be transported into the field of the magnet for immobilizing or restraining movement of magnetically responsive beads within the droplet. Wash reservoirs 920 including reservoir electrodes 922 are provided for dispensing wash droplets onto wash lanes 912. Wash reservoirs 920 may be associated with one or more openings 924 in a droplet actuator substrate (not shown) for transporting wash liquid onto reservoir electrode 922 for use in dispensing wash droplets. Waste reservoir 918 including reservoir electrode 919 is provided for disposing of waste droplets from waste lane 916. Waste reservoir 918 may be associated with one or more openings 925 in a droplet actuator substrate (not shown) for transporting waste liquid out of reservoir 918 to a locus which is exterior to the droplet operations gap. Reservoirs 918 and 920 may be virtual reservoirs or may be partially bounded by a physical barrier (not shown), such as a gasket or spacer partially surrounding the reservoir electrode and including an opening for dispensing of droplets along electrode path 912 or disposal of droplets along path 916.

Droplet actuator 900 may be used to conduct a bead washing protocol. Bead-containing droplets may be provided in wash lanes 912. Washing protocols, optionally including resuspension protocols, may be conducted on lanes 912. Waste droplets may be transported along lane 916, across lanes 912 into waste reservoir 918. Alternatively, each wash lane 912 may be associated with its own waste reservoir. Supernatant (i.e., waste) droplets from wash lanes 912 may be transported using droplet operations to wash lane 916. Supernatant droplets may then be transported in waste lane 916 to waste reservoir 918. Because waste lane 916 is common to wash lanes 912, supernatant droplets must be transported serially (i.e., one after another).

In an alternative example, individual waste reservoirs 920 may be provided for each wash lane 912. Supernatant droplets may be transported simultaneously to individual waste reservoirs. Multiple, individual waste reservoirs provide for increased efficiency (e.g., time to result) in a washing protocol. Multiple waste reservoirs also provide for a reduction in the number of droplet operations electrodes 910 that are required to transport a supernatant droplet to a waste reservoir. Reducing the number of operations electrodes 910 also reduces the potential for cross-contamination between subsequent droplets used in a protocol.

8.1.3 Bead-Mediated Droplet Splitting

In some embodiments, the invention provides a means of splitting a bead-containing droplet. In particular, it is sometimes useful to split a bead-containing droplet in a manner which concentrates the beads into a smaller droplet, thereby providing a substantial reduction in unbound substances surrounding the droplet. For example, in an assay a droplet comprising sample and beads may be incubated together to permit a target substance from the sample to bind to the beads. Following incubation, it may be desirable to remove a large aliquot of sample from the beads prior to initiating a merge-and-split wash protocol. The invention provides techniques for conducting such separation.

FIGS. 10A-10C show a top view of an electrode/magnet arrangement 1000 on a droplet actuator and illustrates a process of separating beads from a droplet. Magnetically responsive beads are split from a rounded or generally circular shaped droplet. In some embodiments, droplet 1016 may have a generally rounded shape. In some cases droplet 1016 has a length at its longest cross-section is less than about 2 times the droplet's width measured along a width axis which is arranged at a 90° angle relative to the lengthwise axis, e.g., as illustrated with respect to droplet 1016 in FIG. 10B. In another embodiment, the droplet's length at its longest cross-section is less than about 1.5 times the droplet's width.

Electrode/magnet arrangement 1000 includes an arrangement of droplet operations electrodes 1010 configured for conducting droplet operations. Droplet 1016 is provided in a droplet operations gap (not shown) or on a droplet operations surface where droplet 1016 is subject to droplet operations mediated by electrodes 1010. Magnet 1014 is provided in proximity to electrodes 1010M. Electrodes 1010M are a subset of electrodes 1010. Magnet 1014 is positioned relative to electrodes 1010M such that when droplet 1016 is atop one or more of electrodes 1010M, any magnetically responsive beads 1022 within droplet 1018 are attracted by the magnetic field of magnet 1014. Alternatively, magnet 1014 is positioned relative to electrodes 1010M such that when droplet 1016 is subject to droplet operations mediated by electrodes 1010M, magnetically responsive beads 1022 within droplet 1016 are attracted by the magnetic field of magnet 1014. The attraction of magnetically responsive beads 1022 may cause beads 1022 to move within droplet 1016 in the direction of magnet 1014. Magnetically responsive beads 1022 may move towards an edge of droplet 1016 which is proximate magnet 1014. The parameters of the configuration may be adjusted such that beads 1022 are attracted towards an edge of droplet 1016, and when droplet 1016 is transported away from magnet 1014, a bead-containing droplet 1023 splits off of droplet 1016. In this and other examples described herein which make use of magnetically responsive beads and magnets, the technique may be optimized by adjusting properties such as interfacial tension of droplet 1016, properties and concentration of magnetically responsive beads 1022, and the pull force exerted by magnet 1014 on magnetically responsive beads 1022. Droplet 1016 may be formed using a buffer having an interfacial tension which is sufficiently low to permit magnetic beads 1022 to remain behind atop magnet 1014 when bead-containing droplet 1023 is transported away from magnet 114. The transporting away may be mediated by the electrodes, e.g., by electrowetting-mediated or dielectrophoresis-mediated droplet operations. In order to enhance the "snapping off" of beads from a droplet that is being transported away from magnetically restrained beads, higher surfactant concentrations may be used. The magnetic bead concentration and the pull force of the magnet may be relatively high.

In general, the following parameters may be adjusted so that transport of a magnetically responsive bead-containing droplet away from the magnetic field will leave behind a highly concentrated droplet including the magnetically responsive beads, which is essentially snapped off as the bead-containing droplet moves away from the magnetic field: size of the droplet relative to the droplet operations electrode, interfacial tension of the droplet, magnetic bead properties and concentration, pull force of the magnet exerted on the magnetically responsive beads, and number, size and orientation of magnets used. For example, the surfactant may be Tween 20, and the concentration of Tween 20 may range from about 0.02% to about 0.1%. Of course, the required concentration will vary depending on the surfactant type. The desired interfacial tension range may typically be in the range of about 1 dynes/cm to about 4 dynes/cm. In general, the greater the size of the droplet relative to the footprint of the electrode, the more favorable is it for bead-mediated droplet splitting to occur. The magnetic bead concentration range is typically from about 1 mg/mL to about 30 mg/mL. Pull force of the magnet may typically range from about 1 lbs to about 100 lbs.

FIG. 10A shows droplet 1016 with beads 1022 therein positioned at a droplet operations electrode 1010M in proximity to magnet 1014. Beads 1022 are attracted and aggregated by magnet 1014. Because a single droplet operations electrode 1010M is active, droplet 1016 is generally circular in shape. FIG. 10B shows droplet 1016 transported using droplet operations away from droplet operations electrode 1010M to an adjacent droplet operations electrode 1010. As droplet 1016 moves away from droplet operations electrode 1010M, a concentration of beads 1022 is formed at an edge of droplet 1016 that is closest to magnet 1014. As droplet 1016 is transported away from magnet 1014, the geometry of droplet 1016 is distorted as the concentration of beads 1022 is restrained while the droplet moves away from magnet 1020. The bead-retaining force of the interfacial tension of droplet 1016 is overcome by the bead-attracting force of magnet 1014 on beads 1022, resulting in the breaking away of a portion of the droplet including the beads. FIG. 10C shows droplet 1016 transported using droplet operations still further away from droplet operations electrode 1010M and to a droplet operations electrode 1010. Droplet 1023 including beads 1022 breaks away (snaps off) from droplet 1016. A similar result can be achieved using a barrier that permits a droplet including magnetically responsive beads or substantially non-magnetically responsive beads to be transported while restraining transport of the beads with the main body of the droplet. The above described technique may also be employed in wash protocols. For example, after the merger of the wash droplet with the bead-containing droplet, the bead-mediated droplet splitting can be employed to result in a bead droplet 1022 with little or no unbound substances and another droplet 1016 that contains most or all of the unbound substances. The process can be required till sensitivity and time to result requirements are met.

FIGS. 11A, 11B, and 11C show a top view of the electrode/magnet arrangement 1000 shown in FIGS. 10A-10C and a process of transporting beads within a droplet. Magnetically responsive beads may be transported within the elongated droplet away from a magnet. The steps shown in FIGS. 11A, 11B, and 11C are substantially the same as those that are described in FIGS. 10A, 10B, and 10C except that, instead of processing a 1× droplet using droplet operations mediated by single active electrodes, droplet 1116 is a slug-shaped 3× droplet and is subjected to droplet operations using three active electrodes for each droplet operation, so that the droplet maintains an elongated form during the droplet operations. Droplet 1116 may be subjected to droplet operations in a manner which causes it to take on a generally elongated shape. In some cases, droplet 1116 length at its longest cross-section is greater than about 1.5 times the droplet's width measured along a width axis which is arranged at a 90° angle relative to the lengthwise axis, e.g., as illustrated with respect to droplet 1116 in FIG. 11A. In another embodiment, the droplet's length at its longest cross-section is greater than about 2 times the droplet's width. In yet another embodiment, the droplet's length at its longest cross-section is greater than about 3 times the droplet's width.

Figure 10:
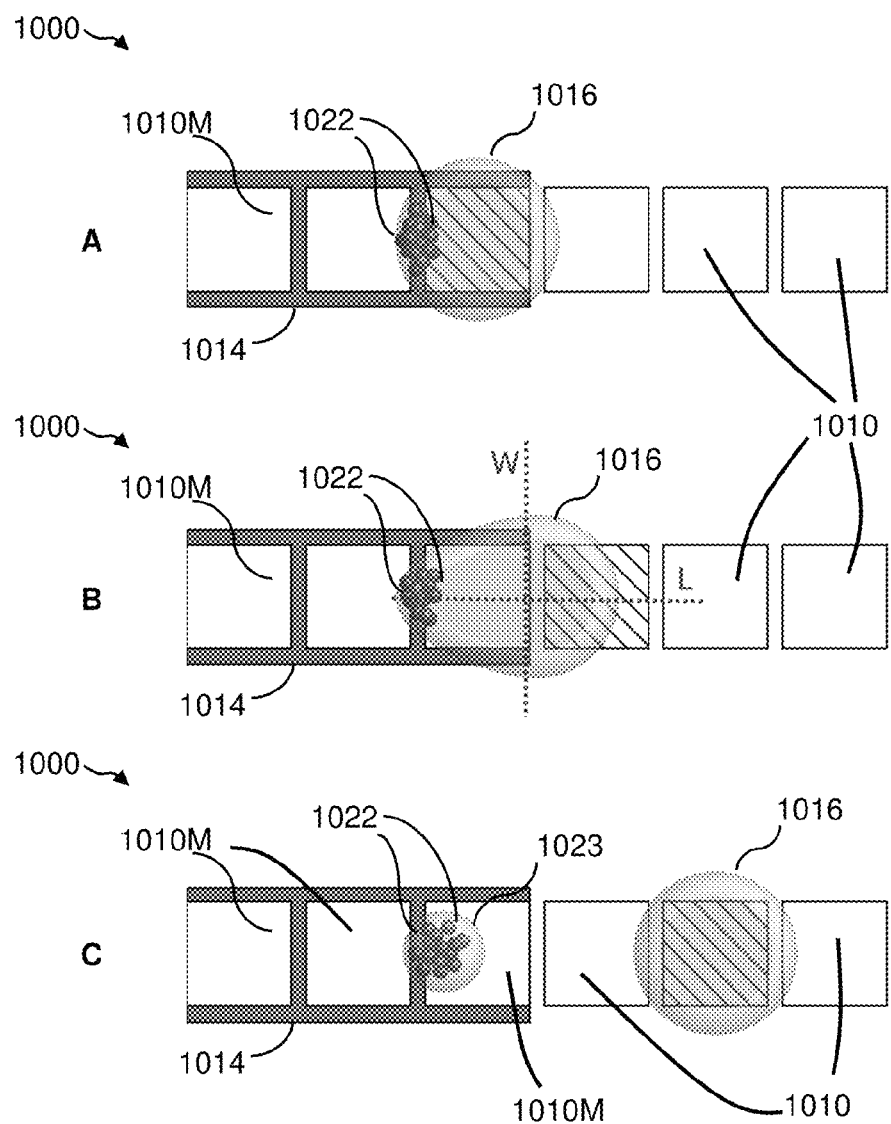
FIGS. 10A-10C show a top view of an electrode/magnet arrangement on a droplet actuator and illustrates a process of separating beads from a droplet.
Figure 11:
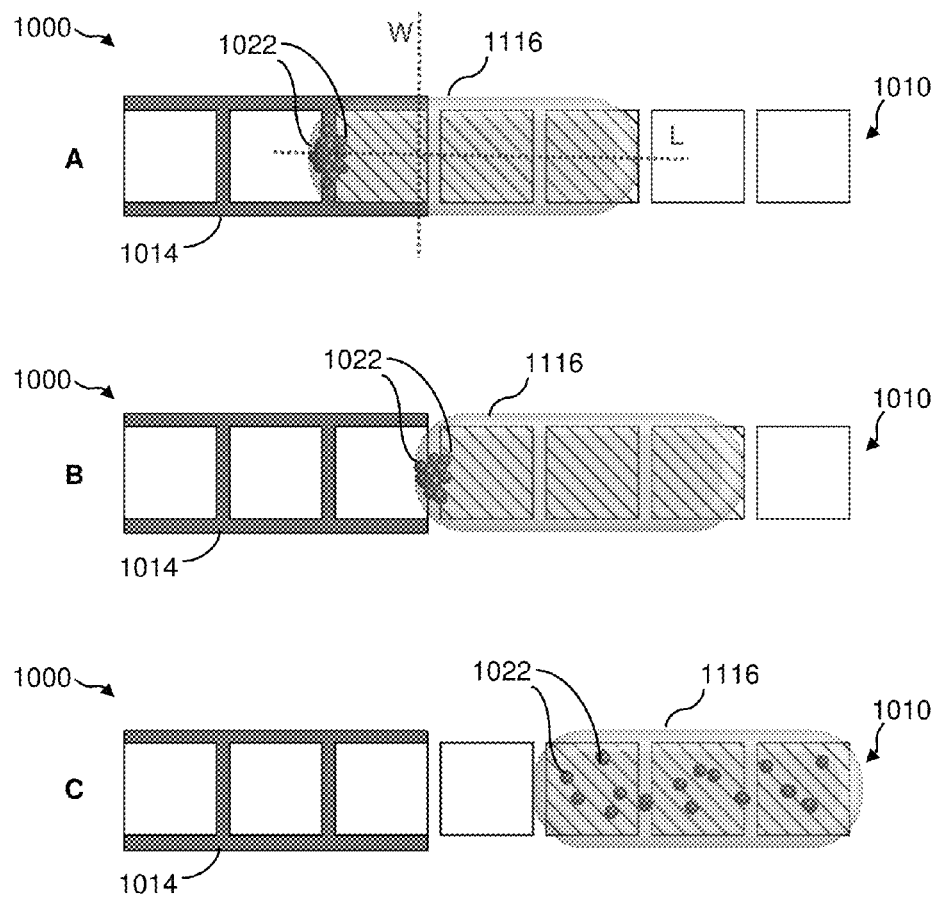
FIGS. 11A-11C show a top view of the electrode/magnet arrangement shown in FIGS. 10A-10C and a process of transporting beads within a droplet.

FIGS. 11A, 11B, and 11C show the process steps of transporting beads 1022 within an elongated droplet 1116 away from magnet 1014. FIG. 11A shows droplet 1116 with beads 1022 therein positioned at droplet operations electrodes 1010 adjacent to magnet 1014. Beads 1022 are attracted and aggregated within an end region of droplet 1116 by magnet 1014. Because three droplet operations electrodes 1010 are active, droplet 1116 takes on an elongated shape. FIG. 11B shows droplet 1116 transported using droplet operations away from droplet operations electrode 1010M to an adjacent droplet operations electrode 1010. As droplet 1116 moves away from magnet 1014, beads 1022 remain within droplet 1116. In general, the following parameters may be adjusted so that transport of a magnetically responsive bead-containing droplet away from a magnetic field will either leave behind or retain the magnetically responsive beads: interfacial tension of the droplet, magnetic bead properties and concentration, pull force of the magnet exerted on the magnetically responsive beads, the number, size and orientation of magnets. The method illustrated in FIG. 11 provides a means for retaining beads in a droplet in which the parameters are such that the beads would otherwise be lost from the droplet if the same droplet were transported away from the magnet in a rounded droplet configuration. Thus, the methods illustrated in FIGS. 10 and 11 provides techniques by which the droplet actuator may be used to selectively leave the beads behind or retain the beads in the droplet as the droplet is transported away from the magnet. In the method illustrated in FIG. 11, the bead-retaining force of the interfacial tension of droplet 1116 overcomes the bead-attracting force of magnet 1014 on beads 1022, resulting in the retention of the beads in the droplet. FIG. 11C shows droplet 1116 with beads 1022 resuspended therein.

8.1.4 Component Ratios

Figure 12:
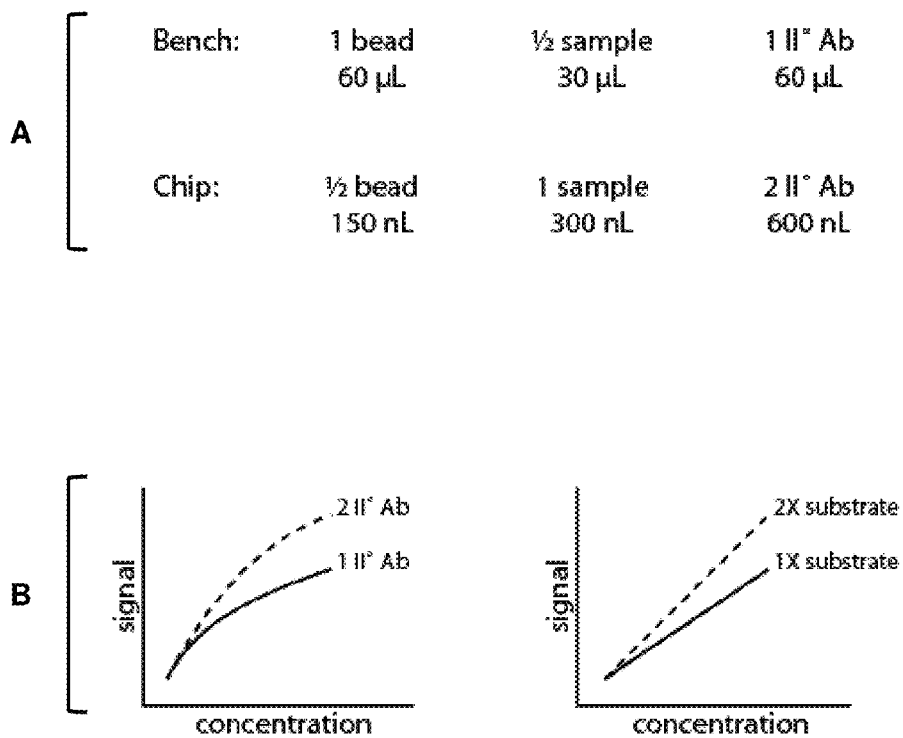
FIGS. 12A and 12B show a comparison of bench top and droplet actuator immunoassay reagent ratios and a plot of reagent concentration versus signal strength.

FIGS. 12A and 12B show a comparison of bench top and droplet actuator immunoassay reagent ratios and a plot of reagent concentration versus signal strength. As shown in FIG. 12A, the ratio of three components of an immunoassay, beads (i.e., capture antibody conjugated to beads), sample (e.g., serum, plasma), and secondary antibody (II° Ab) are provided. For a bench top immunoassay, a typical ratio is 1 part beads (60 µL): ½ part sample (30 µL): 1 part II° Ab (60 µL). A reagent ratio for a droplet actuator based immunoassay is typically ½ bead droplet (150 nL): 1 sample droplet (300 nL): 2 II° Ab droplets (600 nL). The use of fewer beads (i.e., ½ bead droplet or ½ concentration of beads) in a droplet actuator immunoassay provides for increased efficiency of bead washing and a sufficient reduction in non-specific binding of non-target analytes to the capture beads. In addition, the concentration of secondary antibody is the same in both bench top and droplet actuator immunoassays, but the volume of secondary antibody solution is double in the droplet actuator assay. FIG. 12B illustrates the improvement in detection signal that is provided by the use of 2 droplets of secondary antibody and 2 droplets of detection substrate in a droplet actuator immunoassay.

8.1.5 Incubation of Beads with Chemiluminescent Substrate

Figure 13:
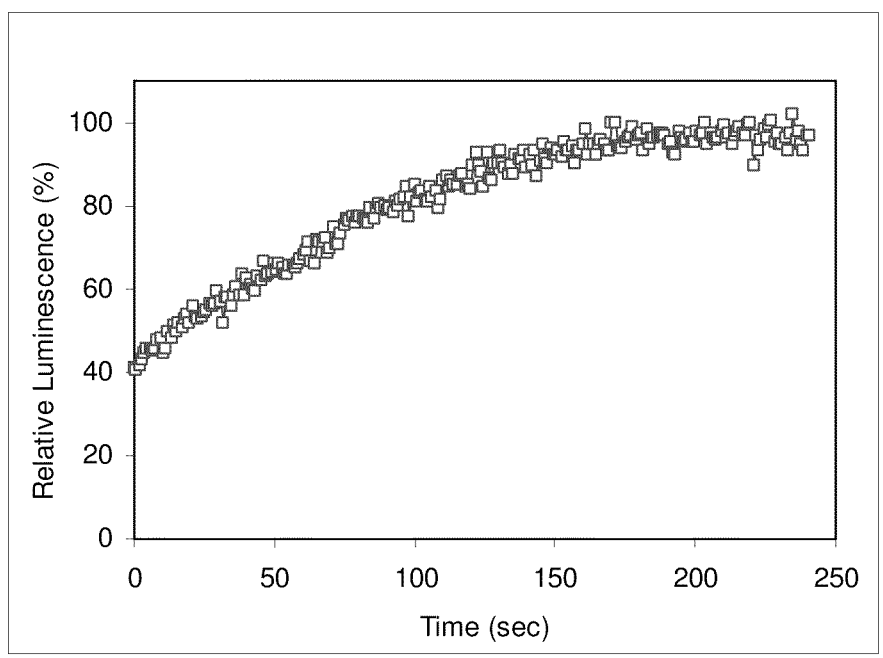
FIG. 13 shows a plot of the kinetics of a reaction between a chemiluminescent substrate and ALP on magnetically responsive beads for Troponin I (TnI).
Figure 14:
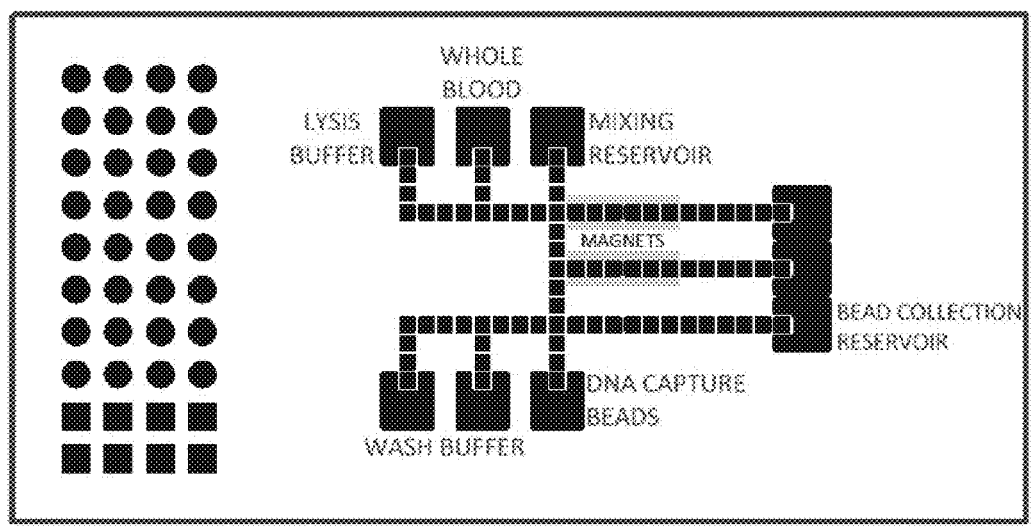
FIG. 14 is a top view of a droplet actuator layout that may be used for extracting DNA from a whole blood sample.

Another parameter which may influence the time to result in an immunoassay is the generation of a signal during the incubation of a chemiluminescent substrate with the washed magnetically responsive beads that include the antigen-antibody complex. FIG. 13 shows a plot of the kinetics of a reaction between a chemiluminescent substrate and ALP on magnetically responsive beads for Troponin I (TnI). Immunoassays were performed on TnI (100 ng/mL) using an on-magnet incubation protocol and a circular shaped droplet washing protocol. As shown in FIG. 14, about 90% of the end point signal was obtained in about 120 to about 130 seconds. For a lower concentration of the analyte, maximum signal was achieved in about <120 seconds. Based on this data, for the type of substrate used, 2 minutes may be selected as an optimum incubation time to generate maximum signal for the chemiluminescence reaction. However, if the chemiluminescence reaction is observed to behave as a flash signal instead of a glow reaction, the 2 minute incubation may be reduced to about a few seconds. The peak intensity of flash signal obtained is again a function of the mixing efficiency between the magnetic beads and the trigger solution. Efficient mixing can be obtained by oscillating the magnetic beads with the substrate solution at high switching speeds.

Immunoassay kits were obtained from Beckman Coulter for Troponin I (TnI) containing capture antibodies conjugated to magnetic beads, reporter antibodies labeled with alkaline phosphatase (ALP) and standards (0 ng/mL-100 ng/mL). Chemiluminescence substrate for ALP (Lumigen APS-5) was obtained from Lumigen Inc. (Southfield, Mich., USA). Wash buffer was 0.05 M Tris-HCl, 0.1M NaCl, 0.02% Tween20 and 0.1 mg/mL bovine serum albumin, pH 9.5. Discarded whole blood samples (obtained from anonymous healthy individuals) were procured from Duke University Medical Center, Durham, USA. TnI standards were prepared by dilution into whole blood at a ratio of 1 part TnI standard: 4 parts blood. The concentrations of the standards that were used to spike the samples were 5, 25, and 100 ng/mL resulting in final TnI concentrations of 1, 5 and 20 ng/mL in blood. A sample droplet was mixed with a droplet containing magnetic beads with primary capture antibodies and another droplet containing the secondary antibody labeled with ALP (reporter antibody). All the droplets were dispensed from their respective on-droplet actuator reservoirs and transported to the reactor zone. During incubation, droplets were shuttled, split and merged to improve binding efficiency. After the formation of the capture antibody-antigen-reporter antibody complex, the magnetic beads were immobilized with a magnet while the unbound material was washed away. After the serial dilution based wash steps, each droplet was transported into a detection loop where a chemiluminescent reagent droplet was dispensed and merged with the bead droplet to produce chemiluminescence from the enzyme-substrate reaction. The chemiluminescent product droplet was then transported to the detection spot and the end point glow of chemiluminescence was detected using the PMT.

8.1.6 Rapid Immunoassays

Using optimized protocols for incubation and washing, a full immunoassay was performed on TnI (5 ng/mL). Magnetically responsive beads were incubated with capture antibody, analyte and secondary antibody labeled with ALP reporter using an off-magnet incubation protocol. Ten slug-based washes were performed to remove the unbound material from the supernatant (wash time approximately 2 minutes). The droplet with washed magnetically responsive beads with the antigen-antibody complex was mixed with one droplet of a chemiluminescent substrate and incubated for 2 minutes. The end point chemiluminescence was detected using a photon counter. In this example, the total time to result was approximately 10 minutes per immunoassay.

8.1.7 Extraction of Human Genomic DNA

FIG. 14 is a top view of a droplet actuator layout 1500 that may be used for extracting DNA from a whole blood sample. Layout 1500 includes six on-actuator reservoirs, each with a capacity of ~2 µL, which may be used for storing and dispensing different reagents. A typical protocol for DNA extraction on a droplet actuator may include the following steps. A droplet of magnetically responsive beads, such as paramagnetic Dynabeads® DNA Direct Universal from Dynal Biotech (1.05 µm diameter), suspended in a lysis buffer is dispensed from an on-droplet actuator reservoir and transported using droplet operations to a specific location on the droplet actuator. The beads, which are magnetically responsive, are held by a permanent magnet placed underneath the droplet actuator. Droplets of whole blood are dispensed from a reservoir and mixed with droplets of lysis buffer (including 10 M NaOH) dispensed from another on-droplet actuator reservoir, into a mixing reservoir in the ratio of 1:6 and mixed for about 10 seconds. Mixing can be performed by one of the several means, for example, by dispensing a droplet and merging the droplet back into the reservoir. Droplets of the cell lysate are transported across the DNA capture beads in succession and the supernatant is pinched off while holding the beads. Droplets of wash buffer stored in separate on-droplet actuator reservoirs are used to wash the beads to remove cell debris. Purified genomic DNA captured on the beads is eluted and collected at the bead collection reservoir. A modification of the protocol would be to have the beads mixed with the cell lysate in the same reservoir and then concentrate the beads into a droplet using a magnet positioned closer to the reservoir and then transport the droplet with the DNA-attached beads to a different location for washing and elution. The collected DNA may be amplified either on the droplet actuator as part of an integrated sample-to-answer droplet actuator or in a commercial thermocycler for further DNA processing or diagnostic applications.

8.1.8 Immunoassay on a Droplet Actuator

Figure 15A:
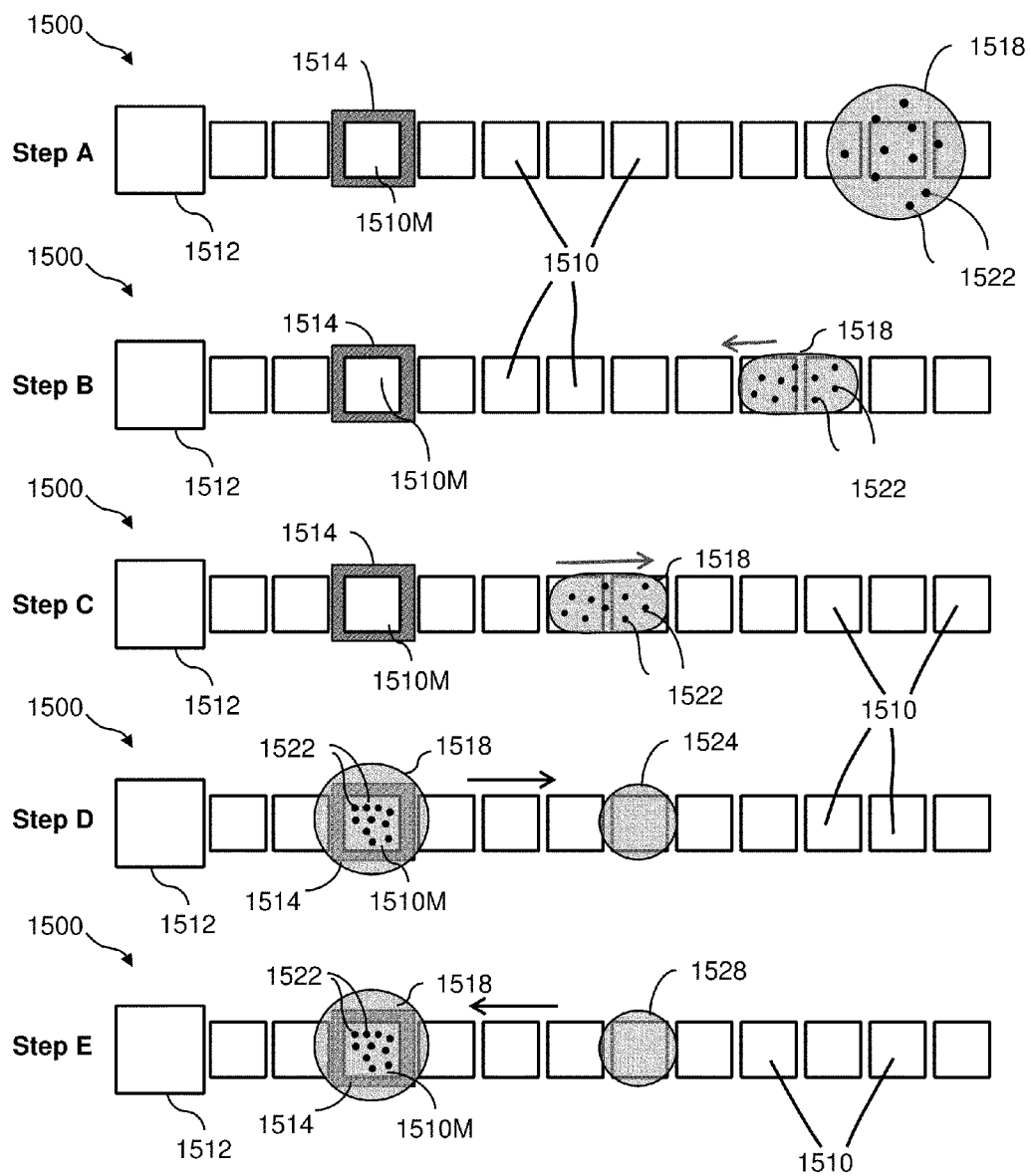
FIGS. 15A and 15B illustrate top views of an electrode/magnet arrangement and show steps in an exemplary, non-limiting, immunoassay process.
Figure 15B:
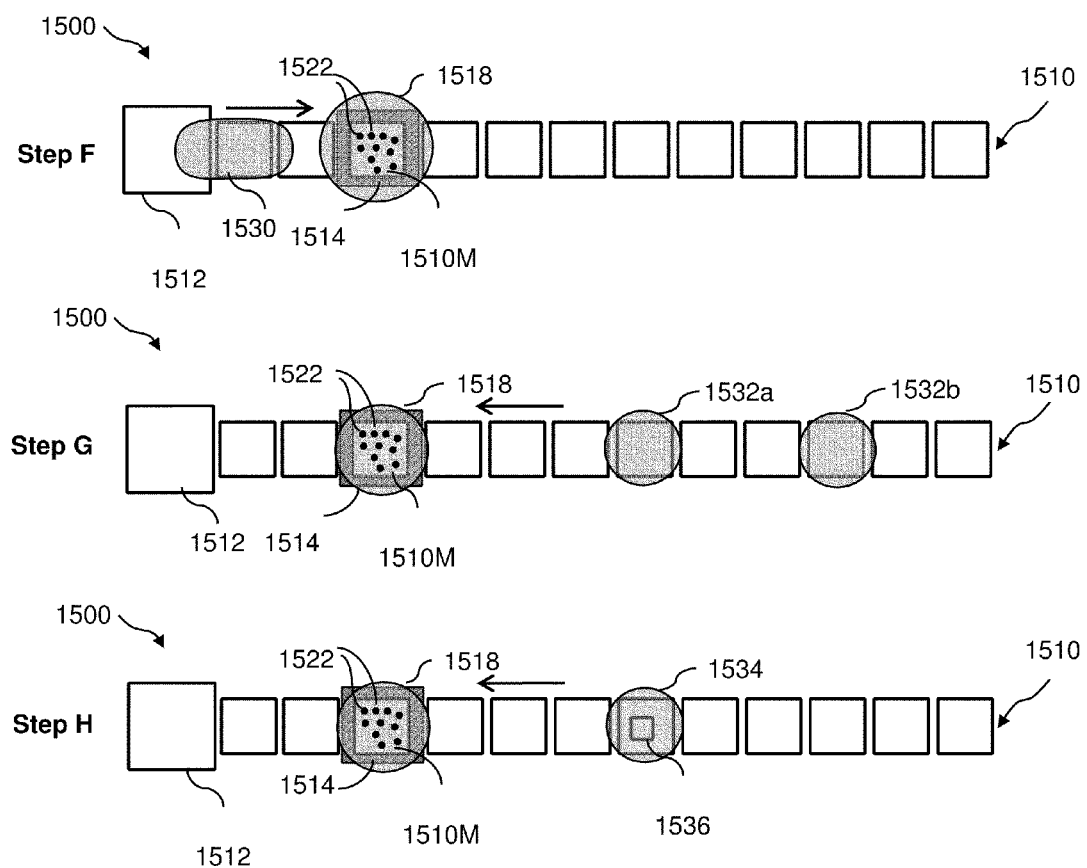

FIGS. 15A and 15B illustrate top views of an electrode/magnet arrangement 1500 and show steps in an exemplary, nonlimiting, immunoassay process. In this non-limiting embodiment, all steps involved in the immunoassay, including sample and reagent aliquoting, incubation with antibodies, bead washing, and enzymatic detection, are fully automated and under software control. The protocol that is illustrated is only an example and the sequence of addition of reagents may vary depending on the assay protocol.

Electrode/magnet arrangement 1500 includes an arrangement of droplet operations electrodes 1510 configured for conducting droplet operations. Droplet 1518 is provided in a droplet operations gap (not shown) or on a droplet operations surface where droplet 1518 is subject to droplet operations mediated by electrodes 1510. Magnet 1514 is arranged in proximity to droplet operations electrodes 1510M. Electrodes 1510M are a subset of electrodes 1510. Magnet 1514 is positioned relative to electrodes 1510M such that when droplet 1518 is atop one or more of electrodes 1510M, any magnetically responsive beads 1522 within droplet 1518 are attracted by the magnetic field of magnet 1514. Alternatively, magnet 1514 is positioned relative to electrodes 1510M such that when droplet 1518 is subject to droplet operations mediated by electrodes 1510M, magnetically responsive beads 1522 within droplet 1518 are attracted by the magnetic field of magnet 1514. The attraction of magnetically responsive beads 1522 may cause beads 1522 to move within droplet 1518 in the direction of magnet 1514. Magnetically responsive beads 1522 may move towards an edge of droplet 1518 which is proximate magnet 1514. Various techniques described herein for manipulating beads in droplets may also be employed with electrode/magnet arrangement 1500. As illustrated, droplet 1518 is a 3× droplet, meaning that its footprint is approximately 3 times the area of one droplet operations electrode 1510. Droplet 1518 may be formed by merging a magnetic bead-containing droplet with a sample droplet, e.g., by merging a 1× magnetic bead containing droplet with a 2× sample droplet. Magnetically responsive beads 1522 are coated with a primary antibody that has an affinity for a specific target antigen. An example of a process of cytokine detection on a droplet actuator may include one or more of the following steps:

Step A of FIG. 15A shows a droplet 1518 that has magnetically responsive beads 1522 therein and is positioned at a certain droplet operations electrode 1510. Droplet 1518 is formed by merging a 1× magnetic bead containing droplet with a 2× sample droplet.

Steps B and C of FIG. 15A show an incubation process, in which droplet 1518 is repeatedly transported back and forth via droplet operations to adjacent electrodes 1510. Repeated transporting of droplet 1518 is used during incubation of beads 1522 and sample in order to provide sufficient resuspension and mixing of magnetically responsive beads 1522 for optimal antibody and antigen binding. Typically, two or three droplet operations electrodes 1510 may be used to transport a 3× droplet 1518, which takes on an elongated or slug shaped geometry. In one nonlimiting example, droplet 1518 may be incubated for 6 minutes using 2 droplet operations electrodes 1510 and transporting droplet 1518 over a span of 8 electrodes at a switching speed of 5 Hertz (Hz). The incubation cycle may include any combination of droplet operations that provides for sufficient mixing of beads 1522 with the contents of droplet 1518. It will be appreciated that timing and steps of the incubation protocol may vary depending on the sample content, the degree and/or specificity of affinity of the beads for the target substance, and the purpose of the assay being performed. Droplet 1518 is illustrated in the figure as a 2× droplet; however, in other embodiments, the droplet may have a size which ranges from about 1× to about 6×, or even larger. In some cases, the droplet may have a size which is approximately 1×, 2×, 3×, 4×, 5×, 6×, or larger.

Step D of FIG. 15A shows droplet 1518 that has magnetically responsive beads 1522 therein transported to droplet operations electrode 1510M. A supernatant droplet 1524 is split off using droplet operations. Because magnetically responsive beads 1522 are attracted to magnet 1514, they are retained in droplet 1518 during the splitting operation. Supernatant droplet 1524 is substantially free of beads. In one example, supernatant droplet 1524 is a 1× droplet and droplet 1518 is now a 2× droplet. Supernatant droplet 1524 may be discarded or transported downstream for use in another process (e.g., merged with another set of beads having affinity for a different target). Droplet 1518 may also be subjected to a wash protocol, such as a merge-and-split wash protocol, to remove additional unbound materials from the beads.

Step E of FIG. 15A shows a reagent droplet 1528 that includes secondary antibody being transported using droplet operations to droplet operations electrode 1510M. Reagent droplet 1528 is merged with droplet 1518 (i.e., a 2× droplet) using droplet operations to form, for example, a 3× reaction droplet. In one example, reagent droplet 1528 is a 1× droplet that includes biotinylated secondary antibody that has an affinity to the target antigen. Merged droplet 1518 is subjected to one or more on-magnet or off-magnet incubation cycles. In one embodiment, merged droplet 1518 is incubated for about 4 minutes the incubation cycle described in steps B and C. Following the incubation period, droplet 1518 is transported using droplet operations to droplet operations electrode 1510M, and a 1× supernatant droplet is split off using droplet operations, as described in step D, in order to yield a 2× droplet 1518. The supernatant droplet (not shown) that includes unbound secondary antibody may be discarded. In an alternative embodiment, droplet 1528 is parked on the electrode path at a position which is outside the attractive influence of the magnet, and droplet 1518 is transported away from the magnet and merged with droplet 1528. The combined droplet may, for example, be positioned in a manner which is similar to the position of droplet 1518 in Step A.

Step F of FIG. 15B shows a bead washing step, in which a wash droplet 1530 is transported from wash reservoir 1512 along droplet operations electrodes 1510. Wash droplet 1530 merges with droplet 1518. Beads 1522 may be restrained during a droplet splitting operation in which one or more bead-free supernatant droplets are removed from droplet 1518. The process may be repeated, and in some cases beads may be resuspended during the washing step, e.g., using the resuspension techniques discussed herein. This is done to remove any unbound material trapped in between the interstices of the magnetic beads. Here, as in other steps and other processes described herein, supernatant droplets may be discarded or transported elsewhere for use as input to another process.

Step G of FIG. 15B shows one or more reagent droplets 1532 (e.g., 1532a, 1532b) transported to droplet operations electrode 1510M. In one example, reagent droplet 1532a that includes a blocking agent (e.g., Elisa Synblock) and reagent droplet 1532b that includes a streptavidin-enzyme conjugate (e.g., streptavidin-alkaline phosphatase (ALP) or streptavidin-horseradish peroxidase) are transported to droplet operations electrode 1510M and merged using droplet operations with droplet 1518. Merged droplet 1518 is incubated for 4 minutes using droplet operations, as described in steps B and C of FIG. 15A. Following the incubation period, droplet 1518 is transported to droplet operations electrode 1510M and a supernatant droplet (i.e., a 1× droplet) is split off using droplet operations, as described in step D of FIG. 15A, in order to yield a 2× droplet 1518. The supernatant droplet (not shown) that includes unbound streptavidin-enzyme conjugate may be discarded. Droplet 1518 is subsequently washed, for example 15 times, as described in step F of FIG. 15B. Following bead washing, a 1× supernatant droplet is split off droplet 1518, as described in step D of FIG. 15A, in order to yield a 1× droplet 1518. The supernatant droplet (not shown) is discarded. Droplet 1518 that includes antibody-antigen sandwich is now ready for detection. In an alternative embodiment, droplet 1528 is parked on the electrode path at a position which is outside the attractive influence of the magnet, and droplet 1518 is transported away from the magnet and merged with droplet 1528. The combined droplet may, for example, be positioned in a manner which is similar to the position of droplet 1518 in Step A. Following this step, the merged droplet may be subjected to an incubation protocol, followed by immobilization of the beads at the magnet and splitting of the droplet to yield a supernatant droplet.

Step H of FIG. 15B shows droplet 1534 (1× droplet) that includes a detection substrate 1536 transported to droplet operations electrode 1510M and merged using droplet operations with droplet 1518. The detection substrate 1536 is converted by the enzyme conjugate into a fluorescent signal (product formation time about 15-20 seconds). The chemiluminescent signal is measured by a detector (not shown) in order to determine the quantity of antigen that is present. In some embodiments, wash buffer droplets may be transported across the detection window following each chemiluminescent droplet to clean up the detection window and the detection loop prior to the next detection.

In a related embodiment, the invention may make use of an enzyme or a series of enzymes to generate a signal amplification cascade. The cascade improves the sensitivity of the detection system. As an example, the signal cascade may terminate with firefly luciferase converting luciferin to light in a "flash" chemiluminescence reaction. In one example, β-galactosidase may be coupled to an antibody or streptavidin. Luciferin-β-galactoside, which is not a substrate for luciferase, may be delivered to the immuno-complex, incubated and hydrolyzed to free luciferin and galactose by the β-galactosidase. The luciferin is then delivered to the PMT where it is mixed with excess ATP and firefly luciferase. All of the luciferin is rapidly converted to light in a flash reaction. Beta-galactosidase can form 700 pmole luciferin per ng enzyme per minute which is equivalent to $7^{12}$ photons per second. In this method the background is very low, and unlike the currently used glow substrates, all of the assay signal may be captured in the short time of the flash reaction. This method also reduces or eliminates the currently observed contamination of long-lived glow chemiluminescent products on-actuator because of the short life time of the luciferin product. It just decays away spontaneously so washing to remove glowing products is eliminated. This system is not a signal regeneration loop like the one used in pyrosequencing.

The steps in the flash assay may be achieved using droplet operations. For example, a droplet protocol may include providing a first droplet comprising β-galactosidase-antibody or β-galactosidase-streptavidin. A second droplet including luciferin-β-galactoside, which is not a substrate for luciferase, may be combined with the first droplet to yield a third droplet. The third droplet may be incubated and hydrolyzed to free luciferin and galactose by the beta-galactosidase. The third droplet including freed luciferin may be transported using droplet operations into the presence of a sensor, such as a PMT, where it is combined using droplet operations with a droplet comprising excess ATP and luciferase (e.g., firefly luciferase). The luciferin is rapidly converted to light in a flash reaction.

The flash assay of the invention may be performed on a droplet actuator, in oil. In some embodiments, a common detection window is used for multiple assays. Where glow assays are used, microdroplets from previous reactions may create background signal that interferes with detection of subsequent droplets. The flash assay of the invention provides a means whereby multiple droplets may be processed for detection in a common detection window on a droplet actuator in a filler fluid with little or no background signal remaining between droplets. For example, little or no background signal from a previous droplet may remain in oil or in microdroplets in oil in proximity to the detection window. In some cases, background signal interference from previous droplets is substantially eliminated by using the flash procedure.

In flash assays, it may be useful to use wash droplets that include the trigger solution to clean droplet transport lanes. Electrode paths that have been used to transport the substrate may be washed by transporting one or more wash droplets across some portion or all of the same area. The wash droplets may include the flash enzyme. For example, the wash droplet(s) may include luciferase or luciferase and ATP.

As another example, acridinium ester (AE) may be used as a chemiluminescent label in a flash assay of the invention. The AE signal quickly rises to a high value, typically in less than about 10, 9, 8, 7, 6, 5, 4, 3, 2 or 1 seconds upon addition of the trigger solution. The signal decays to very low values, typically in less than about 60, 30, 20, or 10 seconds. This decay may eliminate contamination on the detection loop and the detection spot. However, contamination may still be present on the wash lanes and the incubation region by free secondary antibody bound with AE which can potentially affect the subsequent assays performed on the same lane. Transporting 1, 2, 3, 4, 5, 6, 7, 8, 9, 10, or more droplets of the AE trigger solution over the electrodes that are contaminated with antibody bound with AE would produce chemiluminescence which would decay quickly, substantially eliminating AE contamination.

8.1.9 IL-6 and TNF-α Example

A 1× droplet including beads with capture Ab was combined using droplet operations with a 2× droplet sample to yield a 3× reaction droplet. The 3× reaction droplet was subjected to an off-magnet incubation protocol for 6 minutes (shuttled the 3× droplet using 2 electrodes over a span of 8 electrodes with no split at a switching speed of 5 Hz). The reaction droplet was transported to the magnet, and a 1× supernatant droplet was split from the reaction droplet to yield a 2× bead-containing droplet. A 1× droplet including biotinylated secondary Ab was added to the 2× droplet to yield a 3× droplet, which was incubated for 4 minutes using the same protocol at a switching speed of 5 Hz. The reaction droplet was again transported to the magnet, and a 1× supernatant droplet was split from the reaction droplet to yield a 2× bead-containing droplet. Beads were washed using a merge-and-split wash protocol. Wash buffer droplets were 2× slugs of IA wash buffer. This process was repeated 5 times to remove most of the unbound secondary antibody and sample from the supernatant. After washing, a 1× supernatant droplet was split off of the bead droplet using droplet operations to yield a 1× reaction droplet. A 1× droplet including phosphate free Synblock and a 1× droplet including Streptavidin-ALP were added to the 1× bead droplet to yield a 3× reaction droplet. Synblock acts as the blocking agent preventing any non-specific adsorption of reagents onto the beads while the streptavidin-ALP binds to the biotinylated secondary antibody. The 3× reaction droplet was incubated using the same incubation protocol at 5 Hz for 4 minutes. The droplet was transported to the magnet, and a 1× supernatant droplet was split off from the 3× reaction droplet to yield a 2× reaction droplet. The 2× reaction droplet was then subjected to merge-and-split droplet washing protocol. The process was repeated 15 times to ensure no unbound streptavidin-ALP floating in the supernatant which would result in false positives. After washing is complete, the 2× droplet was split at the magnet to yield a final 1× bead-containing droplet. The 1× droplet with the magnetic beads containing the immuno-complex was merged with a 1× chemiluminescent substrate droplet and incubated for 120 seconds. Three wash droplets were transported over the detection pathway and spot to remove any potential contaminants prior to introducing the next droplet for detection.

Figure 16:
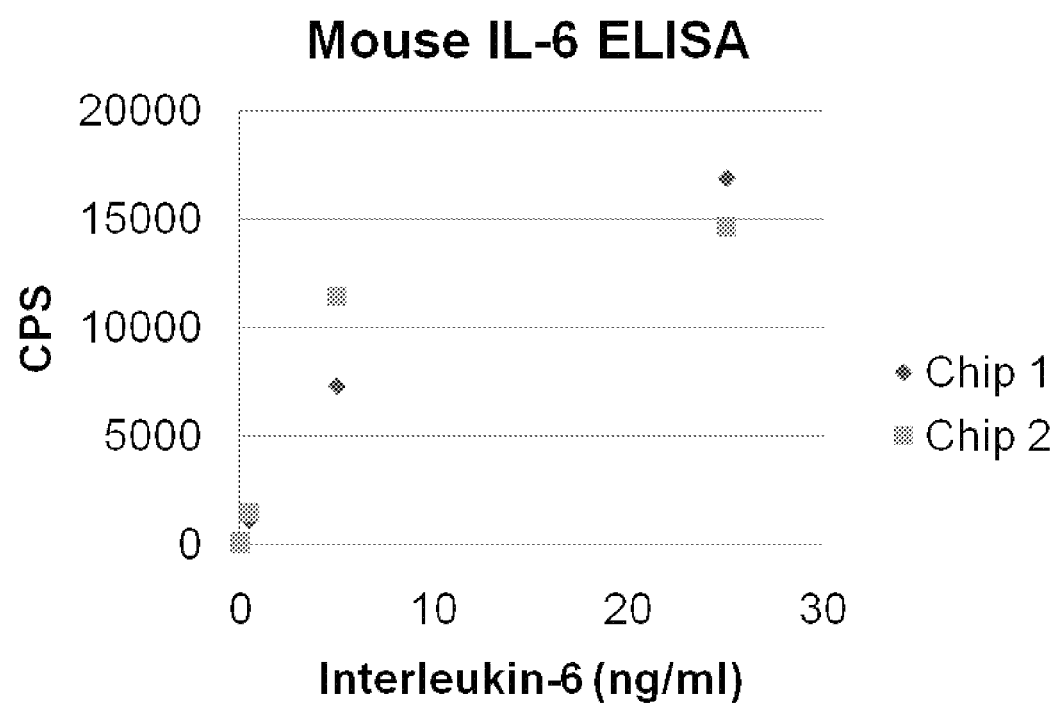
FIG. 16 shows a plot of two 5-point standard curves for cytokine IL-6.

FIG. 16 shows a plot of two 5-point standard curves for cytokine IL-6. Two 5-point standard curves (0, 0.05, 0.5, 5, and 25 ng/mL of IL-6) were obtained in 2 runs for IL-6 performed on 2 separate droplet actuators.

Figure 17:
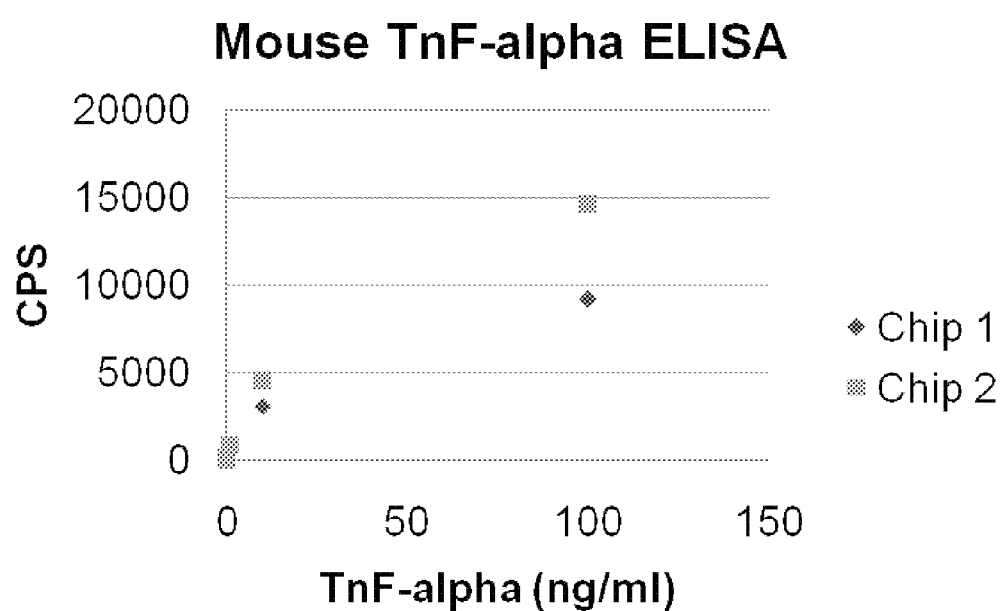
FIG. 17 shows a plot of two 6-point standard curves for cytokine TNF-α.

FIG. 17 shows a plot of two 6-point standard curves for cytokine TNF-α. In this example, two 6-point standard curves (0, 0.01, 0.1, 1, 10, and 100 ng/mL of TNF-α) were obtained in 2 runs for TNF-α performed on 2 separate droplet actuators.

8.2 Digital Microfluidic Spatio- and Spectral-Multiplexing of Assays

The invention also provides a microfluidics assay multiplexing platform that uses digital microfluidics and quantum dots. The invention makes use, in some embodiments, of an integrated multi-well droplet actuator in combination with a spectrometer system. Immunoassays may be multiplexed using quantum dots in droplets on a droplet actuator as optical reporters. For example, the spectral multiplexing capability of quantum dots may be combined with the spatial multiplexing of digital microfluidics, in order to provide a unique, highly multiplexed platform for the problem of cytokine profiling. The microfluidics assay multiplexing platform of the invention may address the key technical barriers that are associated with current state-of-the art technologies in cytokine profiling, such as antibody cross-reactivity and sample volume requirements.

8.2.1 Assay Formats

Figure 18:
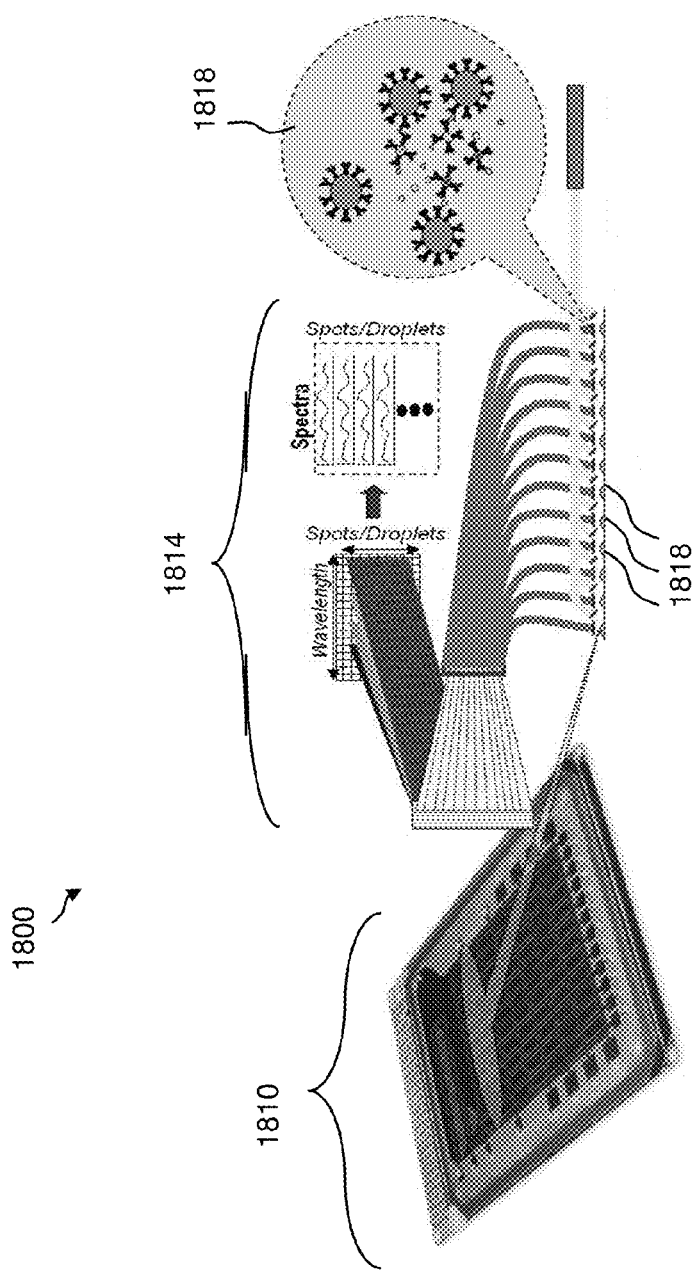
FIG. 18 illustrates a perspective view of a microfluidics assay multiplexing platform of the invention.

FIG. 18 illustrates a perspective view of a microfluidics assay multiplexing platform 1800 of the invention. Platform 1800 makes use of digital microfluidics to achieve spatial multiplexing and quantum dots to achieve spectral multiplexing. Platform 1800 includes a multi-well droplet actuator 1810 in combination with a spectrometer system 1814. The system is capable of processing multiple droplets 1818 for performing various assays, such as immunoassays. In one example, multi-well droplet actuator 1810 is a 12-well droplet actuator. In one example, spectrometer system 1814 is a 12-channel spectrometer system. An example of spectrometer system 1814 is described in more detail with reference to FIGS. 21, 22, and 23.

In one example, platform 1800 of the invention may be used to perform automated and multiplexed cytokine assays. For example assays may be multiplexed using multiple reaction pathways and multiple types of quantum dots on a single multi-well droplet actuator 1810. Droplet actuator 1810 may, in one nonlimiting example, include 8 reagent reservoirs and 12 sample reservoirs for performing 8-plex immunoassays on 12 samples for a total of 96 immunoassays (i.e., 96-plex capability when all 12 samples are the same or 8-plex assays on each of the 12 different samples). Platform 1800 provides a spatio-spectral multiplexing platform by which cytokine immunoassays may be performed by spatially dividing a sample into, for example, 12 droplets and by performing, for example, a further 4-plex immunoassays in each droplet using quantum dots. When 4-plex spectral multiplexing is added, droplet actuator 1810 can be used to perform up to 384-plex assays on a single sample loaded into 12 sample reservoirs where a 4-plex spectral multiplexing is performed on each of the 8-plex spatially multiplexed samples. When 12 different samples are loaded into the sample reservoirs, then 32-plex assays can be performed on each of the 12 samples. Examples of immunoassays that may be performed by use of the microfluidics assay multiplexing platform 1800 of the invention are described in more detail with reference to FIGS. 19, 20A, and 20B. Additionally, an example of multi-well droplet actuator 1810 that has 96-plex capability is illustrated in FIGS. 24A and 24B.

Figure 19:
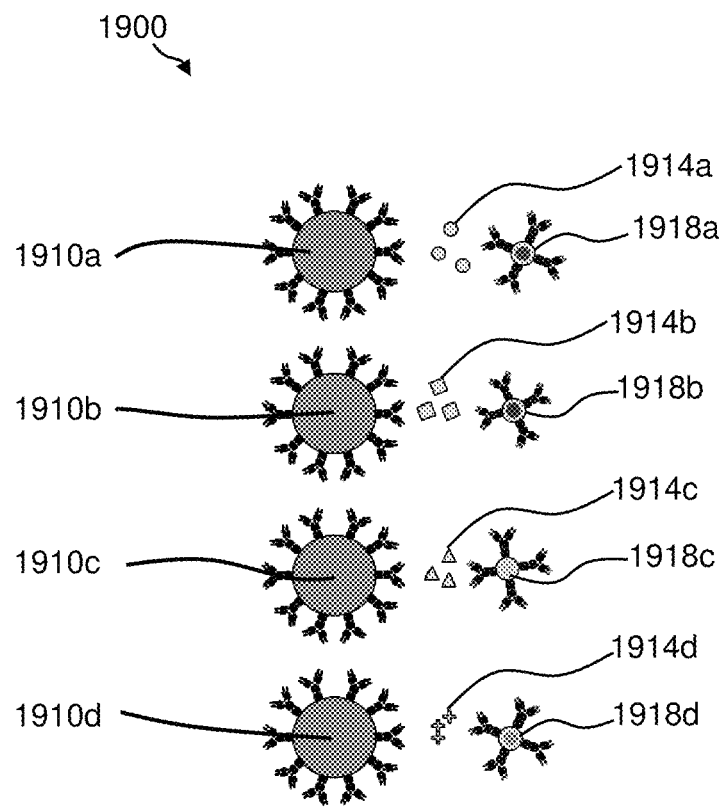
FIG. 19 illustrates the components of an example of a 4-plex immunoassay that may be performed in a single droplet (not shown) using quantum dots within the microfluidics assay multiplexing platform of the invention.
Figure 20:
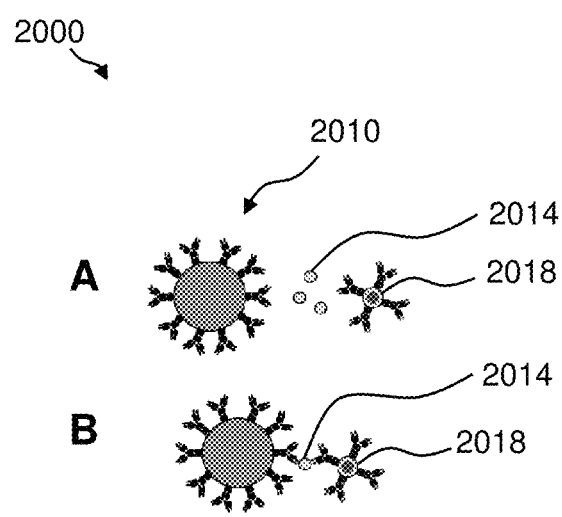
FIGS. 20A and 20B illustrate the components of an example of an immunoassay "sandwich" formation process that may be performed in a single droplet (not shown) using quantum dots within the microfluidics assay multiplexing platform of the invention.

FIG. 19 illustrates the components of an example of a 4-plex immunoassay 1900 that may be performed in a single droplet (not shown) using quantum dots within the microfluidics assay multiplexing platform of the invention. For example, FIG. 19 shows multiple beads 1910 (1910a, 1910b, 1910c, 1910d), multiple types of analytes 1914 (e.g., an analyte 1914a, 1914b, 1914c, and 1914d), and multiple types of quantum dots 1918 (e.g., a quantum dot 1918a, 1918b, 1918c, and 1918d).

Beads 1910 may be any suitable size, including for example, microbeads, microparticles, nanobeads and nanoparticles. In some cases, beads 1910 may be magnetically responsive; in other cases beads 1910 may not be significantly magnetically responsive. Examples of suitable magnetically responsive beads are described in U.S. Patent Publication No. 2005-0260686, entitled, "Multiplex flow assays preferably with magnetic particles as solid phase." Beads 1910 have an affinity for a certain target substance, such as for a certain type of cell, protein, DNA, and/or antigen. When the target substance contacts beads 1910, the target substance may bind to beads 1910. Analytes 1914a, 1914b, 1914c, and 1914d may be different types of target substances to which beads 1910 have an affinity. In one example, analytes 1914a, 1914b, 1914c, and 1914d may be different protein cytokine analytes.

Quantum dots 1918, which are also known as semiconductor nanocrystals, are generally composed of an inner semiconductor core, usually cadmium sulfide (CdS) or cadmium telluride (CdTe), that is surrounded by a high bandgap material, such as zinc sulfide (ZnS). The emission spectrum of quantum dots 1918 is associated with the size of quantum dots 1918, which usually ranges between about 2 nanometers (nm) and about 20 nm. Quantum dots 1918 may be commercially available from suppliers, such as, but not limited to, Life Technologies (Carlsbad, Calif.) and Evident Technologies (Troy, N.Y.). Quantum dots have unique optical properties including narrow emission spectra, broad-range excitation, and high photostability.

The use of quantum dots in digital microfluidics immunoassays provides certain advantages. For example, sensitivity may be increased by using quantum dots rather than using the traditional organic dyes. The flexibility in choices of emission spectra of quantum dots allows the choice of a type of quantum dot that has a wavelength that differs from the autofluorescence background of another key assay component, such as magnetically responsive beads or a PCB substrate or the sample, thus improving signal-to-background noise ratio. Referring to FIG. 19, quantum dot 1918a, 1918b, 1918c, and 1918d may be representative of quantum dots that have different emission spectra, respectively. FIG. 19 shows beads 1910 that are conjugated to capture antibodies; respective analytes 1914a, 1914b, 1914c, and 1914d; and four types of quantum dots 1918 that are conjugated to their appropriate detection antibody.

FIGS. 20A and 20B illustrate the components of an example of an immunoassay "sandwich" formation process 2000 that may be performed in a single droplet (not shown) using quantum dots within the microfluidics assay multiplexing platform of the invention. For example, FIG. 20A shows a certain bead 2010, certain analytes 2014, and a certain quantum dot 2018. FIG. 20B shows analyte 2014 that is bound to both the bead 2010 and to the quantum dot 2018. Analyte 2014 is therefore sandwiched between bead 2010 and quantum dot 2018, thereby forming the link between bead 2010 and a certain type of quantum dot 2018.

The process that is shown in FIGS. 20A and 20B is an example of an immunoassay sandwich format that incorporates quantum dots, where the assay antibody sandwich occurs on a solid support (e.g., bead 2010) and the secondary optical labels (e.g., quantum dot 2018) may be imaged using a fluorescent microscope. Although magnetic beads are shown in the figure for solid support, the surface of the droplet actuator modified with capture elements, such as nucleic acids, antibodies or antigens, can be used as a fixed solid support instead of magnetic beads. In one example, the binding and the number of immobilized quantum dots may be correlated to the level of an analyte, such as prostate-specific antigen (PSA), by fluorescent imaging of quantum dots on, for example, a carbon substrate. Furthermore, a spatially multiplexed cytokine approach using a protein microarray with a single type of quantum dot may be used to detect certain cytokines (e.g., TNF-α, IL-8, IL-6, MIP-1β, IL-13 and IL-1) in a single solution down to a parts-per-million concentration level. Any analytes detectable using a sandwich immunoassay or competitive immunoassay format may be detected using the protocols of the invention.

Separate pools of beads 2010 may be conjugated to the corresponding capture antibody of the cytokine protein of interest. By way of example, four separate conjugations occur for a 4-plex assay. In addition, four detection antibodies may be separately conjugated to four types of quantum dots (e.g., quantum dots 2018*a*, 2018*b*, 2018*c*, and 2018*d*). Referring again to FIG. 19, four pairs of conjugates (e.g., four bead 2010/quantum dot 2018 pairs) with their respective protein cytokine analytes 2014 is shown. These conjugates represent separate droplet pools of conjugates (of course, without analyte at this point) may be combined prior to introduction on the multi-well droplet actuator 1810 of microfluidics assay multiplexing platform 1800. When combined with a sample that includes analytes 2014 (e.g., cytokine analytes), the beads 2010, analytes 2014, and quantum dots 2018 form a sandwich. After the conjugate and sample are mixed, multiple wash steps may occur in order to remove unbound quantum dots 2018. After washing, the sample may be resuspended in a droplet and transported to the detection zone (e.g., the interface between multi-well droplet actuator 1810 and spectrometer system 1814) of multi-well droplet actuator 1810.

8.2.2 Detection System

By using, for example, four types of quantum dots (e.g., quantum dots of different emission spectrum) and multiple separate detection spots that are provided in microfluidics assay multiplexing platform 1800, the multiplexing capability may be expanded to n-plex. An important aspect of combining two multiplex-schemes, is utilizing compatible antibody pairs. Certain spectrometer tools and algorithms are provided for spectral uncoupling of the assay signal from the respective types of quantum dots.

Figure 21:
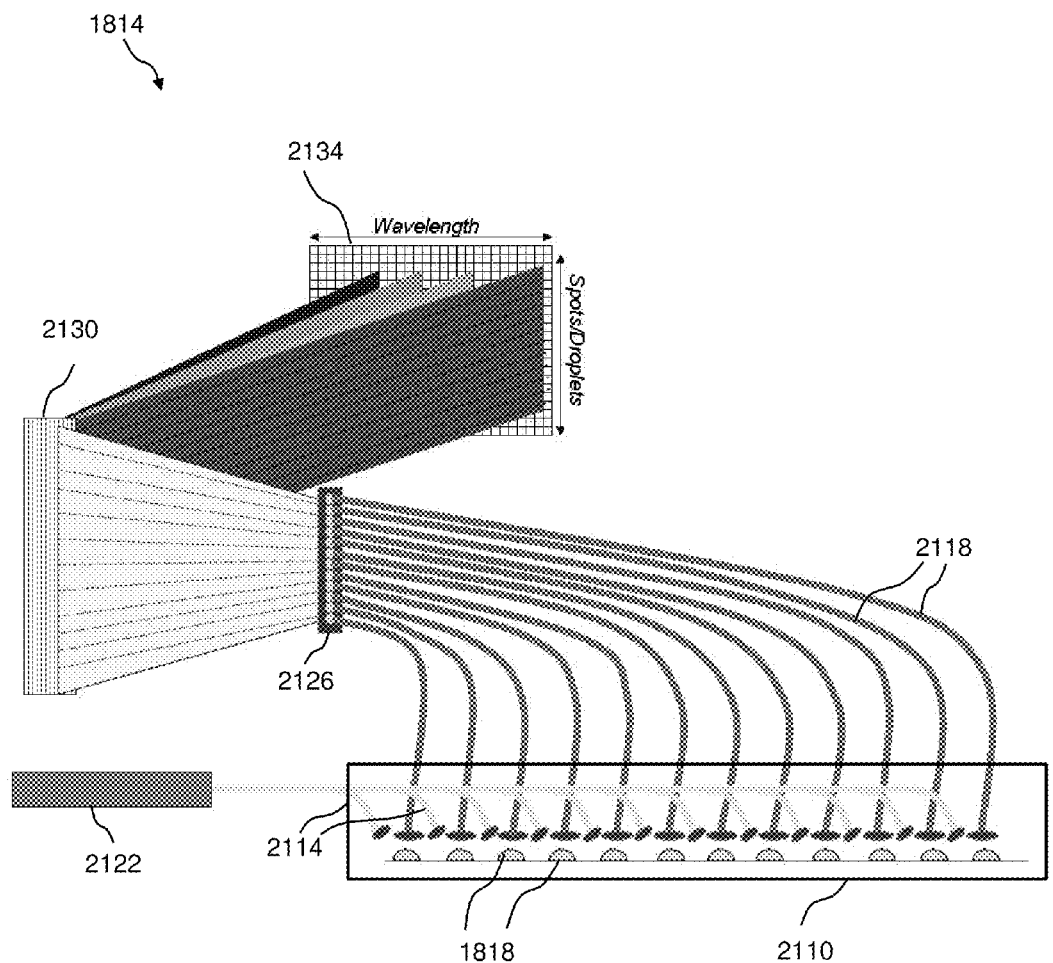
FIG. 21 illustrates a perspective view of spectrometer system of microfluidics assay multiplexing platform of the invention.

FIG. 21 illustrates a perspective view of spectrometer system 1814 of microfluidics assay multiplexing platform 1800 of the invention. Spectrometer system 1814 may include multiple optical fibers arranged to excite and collect quantum dot fluorescence from multiple microfluidic droplets. In one embodiment, spectrometer system 1814 may be a 12-channel spectrometer system that includes a 12-channel fiber-based readout head 2110. In this embodiment, 12 excitation fibers 2114 enter fiber-based readout head 2110 and 12 collection fibers 2118 exit fiber-based readout head 2110. Excitation fibers 2114 and collection fibers 2118 are optical fibers. 12-channel fiber-based readout head 2110 is designed to hold one end of each excitation fiber 2114 and each collection fiber 2118 in alignment with a respective liquid channel (not shown) of multi-well droplet actuator 1810 and with a respective droplet 1818. An example of a 12-channel fiber-based readout head 2110 is described in more detail in FIG. 23.

The opposite ends of the 12 excitation fibers 2114 are optically coupled to a light source, such as an ultraviolet (UV) source 2122. The opposite ends of the 12 collection fibers 2118 may be arranged in a linear array, e.g., a spectrometer slit 2126. The slit 2126 may be imaged through a diffraction grating 2130 onto a two-dimensional (2D) charge-coupled device (CCD) array 2134. This arrangement preserves the spatial information (y-axis) from each droplet 1818 and disperses the spectral information onto the x-axis.

While a spectrometer system, such as spectrometer system 1814, may be the preferred method of separating spectral information from multiple quantum dots because of cost, size, and performance advantages, microfluidics assay multiplexing platform 1800 is not limited to spectrometer system 1814 only. Alternatively, an optical system for separating spectral information may include dichroic beamsplitters in combination with narrowband filters. For example, a filter-based design that may measure 12 spots and 4 spectral channels may include 36 separate dichroic beamsplitters (e.g., 3 per detection spot), 48 narrowband filters, and 48 detectors. However, filter-based designs may be considerably more costly and complex as compared with the fiber-based spectrometer system, especially as the multiplexing number increases, such as to 8 multiplexed quantum dots.

Figure 22:
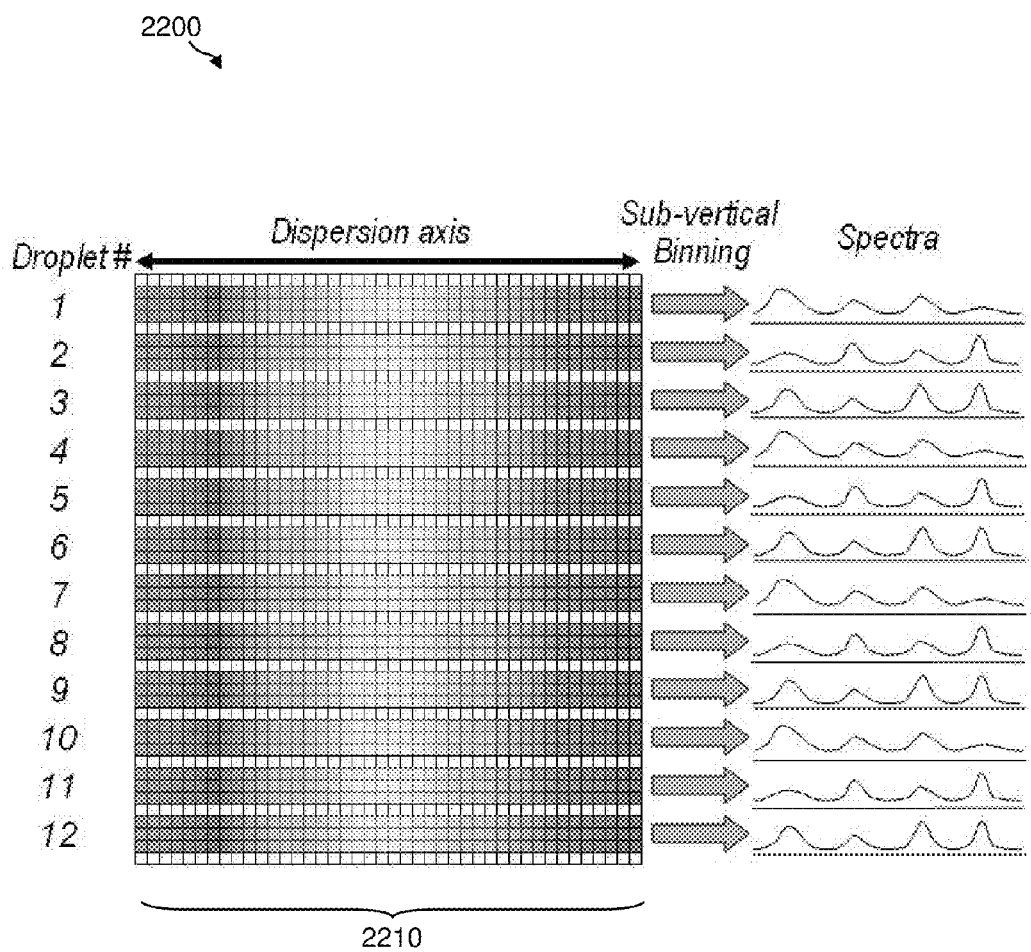
FIG. 22 illustrates a concept for turning the information of a 2D CCD array into multiple spectra.

FIG. 22 illustrates a concept 2200 for turning the information of a 2D CCD array 2134 into multiple spectra. A grid area 2210 represents 2D CCD array 2134. Information from each spot is dispersed along the x-axis, which is the dispersion axis. Vertical pixels are binned in each vertical sub-section corresponding to the different droplets (e.g., each of the 12 droplets 1818). These summed pixels create a spectrum for each droplet.

Figure 23:
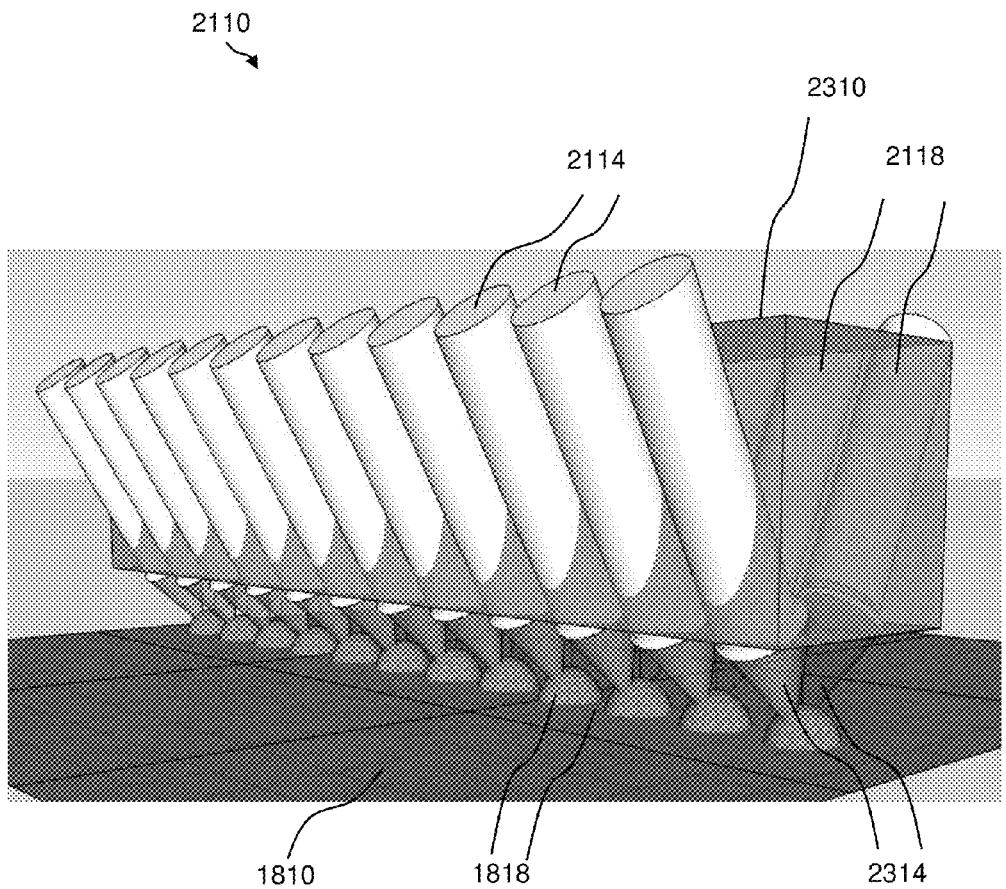
FIG. 23 illustrates a perspective view of 12-channel fiber-based readout head of FIG. 21, showing more details thereof.

FIG. 23 illustrates a perspective view of 12-channel fiber-based readout head 2110 of FIG. 21, showing more details thereof. 12-channel fiber-based readout head 2110 includes the 12 excitation fibers 2114 and 12 collection fibers 2118, as described in FIG. 21. Additionally, 12-channel fiber-based readout head 2110 further includes support block 2310 in which are embedded one end of the 12 excitation fibers 2114 and 12 collection fibers 2118. A substrate, such as block 2310, may be formed, for example, of an epoxy resin material. A substrate, such as block 2310, secures the ends of excitation fibers 2114 and collection fibers 2118 in a desired position relative to assay droplets on multi-well droplet actuator 1810.

A coupling lens may be provided at the end of each excitation fiber 2114 and collection fiber 2118. FIG. 23 shows coupling lenses 2314 that are arranged to distribute light to, and/or collect light from, droplets 1818. Excitation fibers 2114 in combination with coupling lenses 2314 are used to focus the excitation light from, for example, UV source 2122 onto droplets 1818. Collection fibers 2118 in combination with coupling lenses 2314 are used to collect the quantum dot fluorescence from each droplet 1818.

The 12-channel fiber-based readout head 2110 makes use of oblique incidence excitation and collection from each droplet. Droplets 1818 represent microfluidic droplets each including multiple types of quantum dots. FIG. 23 shows two fibers (e.g., one excitation fiber 2114 and one collection fiber 2118) per droplet 1818. At the end of each excitation fiber 2114 and collection fiber 2118 are the coupling lenses 2314 that either focus the excitation light to the quantum dots in the droplet 1818 or collect light from the droplet 1818 to the collection fiber 2118. These excitation fiber 2114 and collection fiber 2118 pairs are arranged linearly along the length of the detection zone on multi-well droplet actuator 1810 that includes droplets 1818; however, it will be appreciated that the arrangement need not be linear at the collection end. Any fiber array pattern (e.g., grid or other preselected arrangement, such as an irregular arrangement) at the sample end, and the fibers may coalesce into a linear format at the spectrometer slit. In the specific embodiment illustrated here, the droplets 1818 on multi-well droplet actuator 1810 may have a spacing of, for example, about 4.5 millimeters (mm) between assay-based droplets.

The operation of example spectrometer system 1814 is generally as follows. In order to detect quantum dot emission from 12 separate spots without optical crosstalk, the design of spectrometer system 1814 incorporates the 12 collection fibers 2118 from 12 droplets 1818 to a vertical position along the narrow slit 2126, as shown in FIG. 21. The collected light from the end of each collection fiber 2118 at slit 2126 is imaged onto the 2D CDD array 2134, dispersed along the (x-axis) wavelength axis and confined to a defined area along the y-axis. FIG. 22 shows the binning scheme from 2D CDD array 2134. As shown in FIG. 22, light from each droplet 1818 is confined to a vertical zone and dispersed along the x-axis (dispersion axis). Each of these vertical zones is separately binned to provide the spectra shown in FIG. 22. Sub-vertical binning allows the separation of spatial and spectral information over the 12 droplets 1818 that are being interrogated. In the alternative embodiment of the dichroic system, separate filters are provided for each quantum dot and each droplet measurement channel.

8.2.3 System Integration

Platform 1800 of the invention provides high immunoassay multiplexability by dividing the multiplexability down into both the spatial and spectral regime, by combining spatial multiplexing in the digital microfluidic platform and spectral multiplexing in quantum dots. Microfluidics assay multiplexing platform 1800 provides sandwich immunoassay capability with the ability to reach detection limits that are clinically prognostic. While FIGS. 18 through 23 describe a combined multiplex approach of a 4-plex spectral multiplex capability with a 12-plex spatial multiplex capability, this is exemplary only. Microfluidics assay multiplexing platform 1800 of the invention may be used to combine n-plex spectral multiplex capability with a m-plex spatial multiplex capability, where n and m denote two numbers for the order of multiplexing and in a limiting case can be the same order. Microfluidics assay multiplexing platform 1800 of the invention may be, for example, a 96-plex protein assay system that provides spectral multiplexing to an 8-plex spectral capability combined with 12-plex spatial capability, thereby proving 96-plex capability using only about 30 microliter (μL) total sample. In existing multiplexing technology, achieving multiplexability beyond 10-plex in a single solution without assay cross-reactivity is an extremely difficult exercise. However, by combining spatial and spectral multiplexing in the microfluidics assay multiplexing platform 100 of the invention, this antibody-crosstalk barrier can be mitigated and reduced to order of spectral multiplexing. For example, instead of a 10-plex (where 10 antibody pairs resulting in 100 combinations need to be tested for cross reactivity), with spectral multiplexing, two 5-plex assays can be setup which broadens the potential combinations of antibody pairs (where 5 antibody pairs result only in 25 combinations).

8.3 Dielectrophoresis

The invention provides a droplet actuator having unique electrode structures for manipulating particles within a droplet on the droplet actuator, as well as methods of performing such manipulations. The invention makes use of dielectrophoresis (DEP). Polarizable particles are concentrated at locations of highest or lowest electrical field strength. The droplet actuator of the invention includes electrodes configured to produce non-uniform electrical fields, i.e., fields in which electrical field intensities are spatially variable. In this manner, particles may be concentrated, regionalized, isolated, or trapped within or guided to a region of a droplet on a droplet actuator. The DEP electrodes of the invention may be configured in association with the top substrate (when present) and/or on the bottom substrate of the droplet actuator. Typically, the DEP electrodes will be on a surface of the top and/or bottom substrate and will be covered with a dielectric coating. In certain embodiments, the electrodes used for establishing a DEP effect may double as electrowetting electrodes.

FIGS. 24A and 24B illustrate one configuration of a portion of a droplet actuator of the invention. FIG. 24B shows a cross-section of FIG. 24A along the line xy. The droplet actuator includes a top substrate 2401 and a bottom substrate 2402 separated by a gap 2403. DEP electrodes 2405A,B,C,D are associated with top substrate 2401. A droplet operations electrode 2410, which may be part of a path or array of droplet operations electrodes (not shown), is associated with bottom substrate 2402. DEP electrodes 2405 and droplet operations electrode 2410 are each coated with a dielectric 2420A, 2420B. A hydrophobic coating may also be provided on the dielectric, rendering hydrophobic the surfaces of top substrate 2401 and bottom substrate 2402 exposed to gap 2403.

DEP electrodes 2405A,B,C,D are wire electrodes having a quadripolar DEP geometry. In the illustrated embodiment, they terminate at DEP region 2425 which is centrally located relative to droplet operations electrode 2410. Other arrangements are possible within the scope of the invention. In DEP particle trapping configuration, electrodes 2405A and D will have the same phase and electrodes 2405B and C will have an opposite phase relative to the phase of electrodes 2405A and D. However, other arrangements are possible within the scope of the invention. For example, in one embodiment, particles may be trapped and rotated by applying a difference between each of adjacent electrodes 2405A,B,C,D, which is less than 180°. For example, it may be useful to apply a 90° difference between each of electrodes 2405A,B,C,D, e.g., electrode 2405A is 0°, 2405B is 90°, 2405C is 180°, and 2405D is 270°.

Generally speaking, DEP region 2425 is configured such that DEP fields can influence one or more particles within a droplet on a droplet operations electrode. The size of DEP region 2425 may be selected based on the number, size, and/or DEP properties of particles to be influenced by the DEP fields. For example, where particles are to be trapped, more particles can be trapped in a larger DEP region 2425. Similarly, where it is desirable to trap a single particle, the size of the DEP region 2425 may be selected accordingly.

Figure 24:
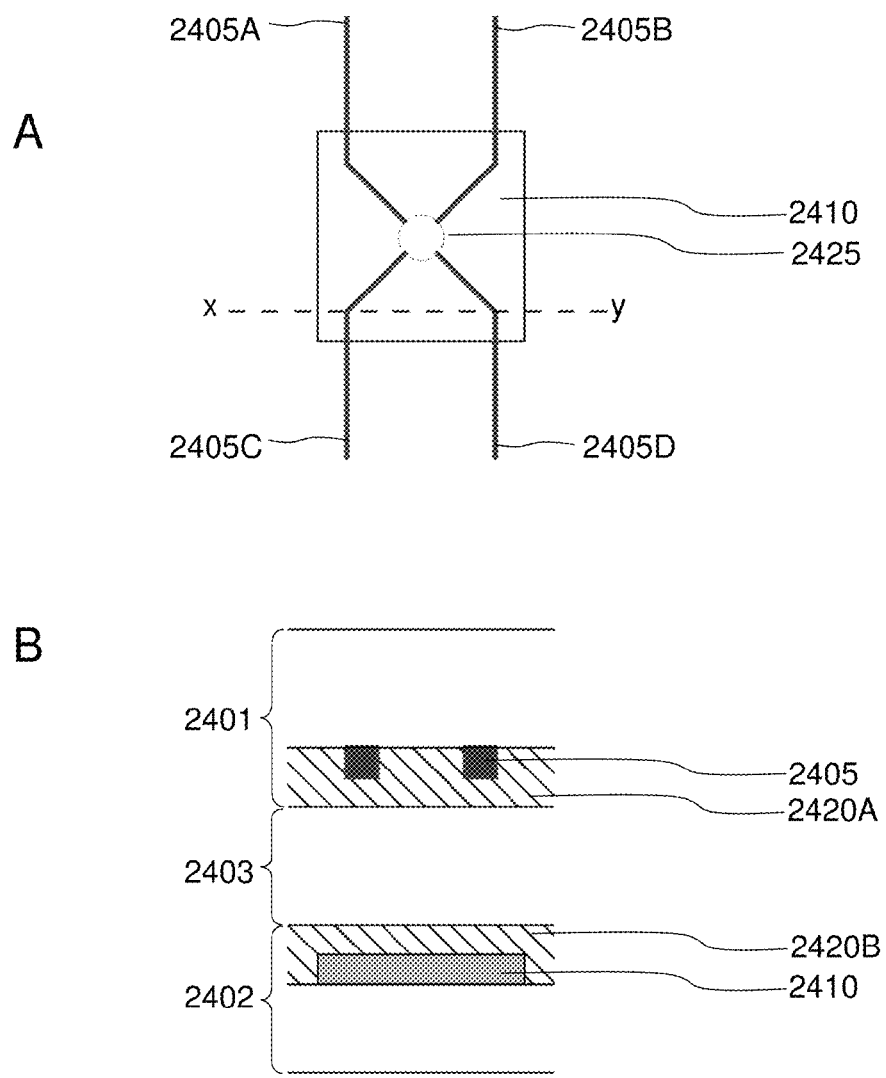
FIGS. 24A and 24B illustrate one configuration of a portion of a droplet actuator of the invention.
Figure 25:
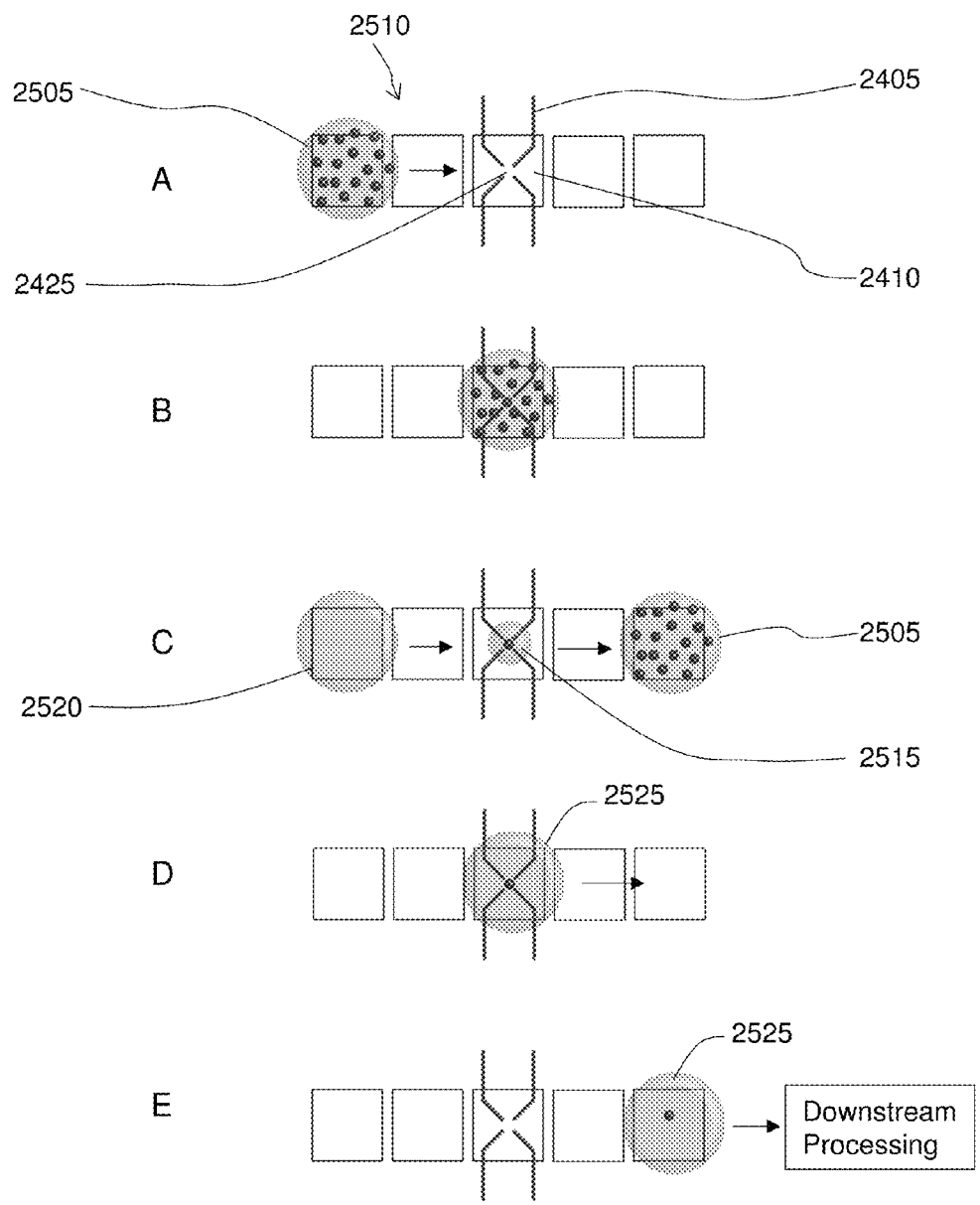
FIGS. 25A-25E illustrate the configuration of FIG. 24 in operation.

FIGS. 25A-25E illustrate the configuration of FIG. 24 in operation. As shown in FIG. 25A, droplet 2505 comprising one or more particles may be situated on a path of electrodes 2510 including electrode 2410. FIG. 25B illustrates that droplet 2505 may be transported along path 2510 onto electrode 2410 using droplet operations. At electrode 2410, DEP electrodes may be activated, thereby trapping one or more particles in DEP region 2425. FIG. 25C illustrates that droplet 2505 may be transported using droplet operations along electrode path 2510 away from electrode 2410, leaving behind daughter droplet 2515, including the trapped one or more particles. A daughter droplet will be formed where the DEP force is greater than the interfacial tension of the droplet being transported away. Alternatively, a variety of droplet operations may be used to remove one or more droplets including the remaining (not trapped) particles. For example, this may be accomplished using a wash protocol whereby a new droplet lacking particles is combined with droplet 2505, and the combined droplet is split to remove a droplet including untrapped particles. This process can be repeated until only trapped particles remain in the droplet on electrode 2410. In the process illustrated in FIGS. 25C, 25D and 25E, a new droplet 2520 (e.g., a buffer droplet, reagent droplet, or sample droplet) is transported along electrode path 2510 onto electrode 2410 into contact with droplet 2515, yielding a new combined droplet 2525. DEP electrodes 2405 may be deactivated to release the one or more particles into droplet 2525. Droplet 2525 may be transported along electrode path 2510 or otherwise subjected to additional droplet operations or analyses. Trapped particles may have different DEP properties relative to droplets that are not trapped. In this manner, particles having different DEP properties may be separated.

Figure 26:
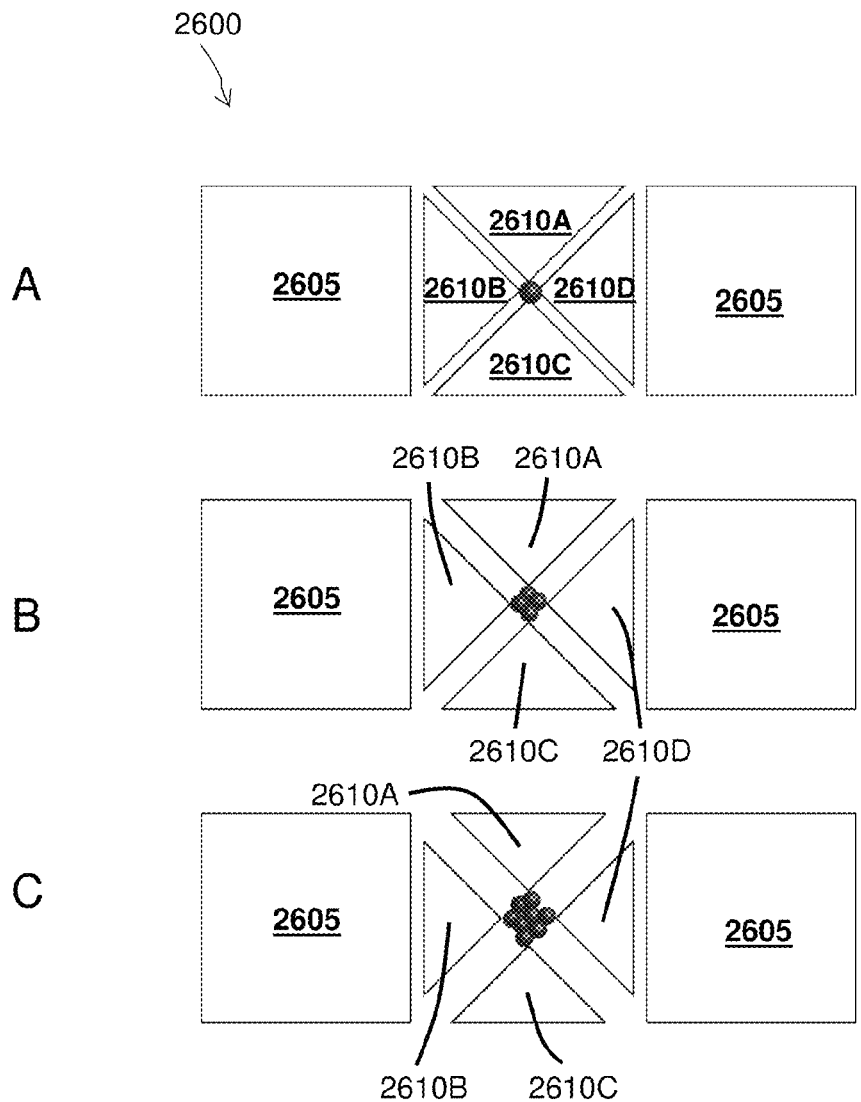
FIGS. 26A-26C illustrate an electrode path, including a specialized electrode, which can be used as a droplet operations electrode and as a DEP electrode.

FIGS. 26A-26C illustrate an electrode path 2600, including a specialized electrode 2610, which can be used as a droplet operations electrode and as a DEP electrode. Electrode 2610 is configured to provide a quadripole trapping geometry having 4 electrodes 2610A, B, C and D. In the illustrated version, each of the electrodes 2610A, B, C and D is a 45-45-90° triangle, with the 90° angles facing each other to form a square electrode or an electrode which is approximately square. It will be appreciated that a variety of other electrode configurations are possible to achieve the same effect. For example, in the illustrated embodiment, particles are trapped at a location which is central to the 4 electrodes, but they could be at any point on or near the electrode, preferably within the footprint of the droplet. Electrode configuration 2610 is positioned within a path of square droplet operations electrodes 2605.

In normal droplet operations, the electrodes 2610A-D can be operated in tandem as an ordinary droplet operations electrode. However, in DEP mode of operation, the electrodes can be used to trap particles. In this mode, electrodes 2610A and C will have a first phase and electrodes 2610B and D will have a second phase which is opposite (i.e., differs by 180°) relative to the first phase. FIGS. 26A, 26B and 26C illustrate that different gap sizes can be used to establish trapping zones for differently sized particles or for capturing different amounts of particles. Among other things, by controlling the number of particles captured, it is possible to aliquot particles from one droplet into multiple sub-droplets, each sub-droplet having an approximately equal quantity of the particles.

Figure 27:
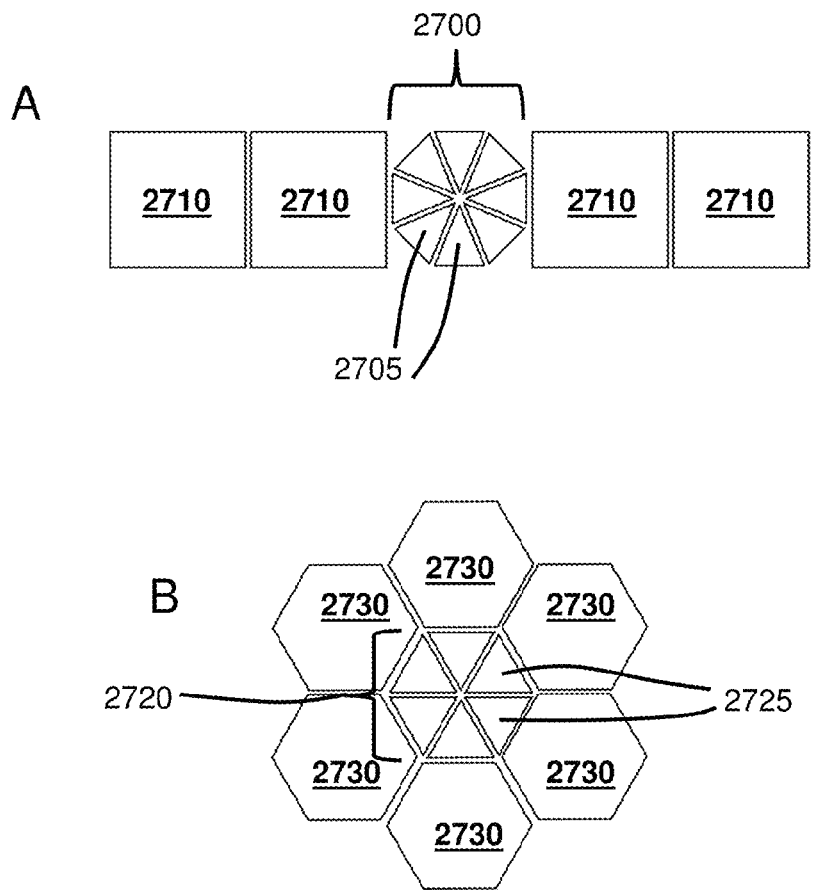
FIG. 27A illustrates an octagon-shaped DEP electrode configuration based on the use of 8 triangular shaped electrodes.
FIG. 27B illustrates a hexagon-shaped DEP electrode configuration based on the use of 8 triangular shaped electrodes.

FIG. 27A illustrates an octagon-shaped DEP electrode configuration 2700 based on the use of 8 triangular shaped electrodes 2705. Opposite electrodes will generally have phases which differ by about 180°. Gaps between the triangular electrodes can be selected to establish trapping zones for trapping particles based on size or quantity. Electrode configuration 2700 is positioned within a path of square droplet operations electrodes 2710.

FIG. 27B illustrates a hexagon-shaped DEP electrode configuration 2720 based on the use of 6 triangular shaped electrodes 2725. Opposite electrodes in the will generally have phases which differ by about 180°. Gaps between the triangular electrodes can be selected to establish trapping zones for trapping particles based on size or quantity. Electrode configuration 2720 is positioned within grid of hexagonal droplet operations electrodes 2730.

Figure 28:
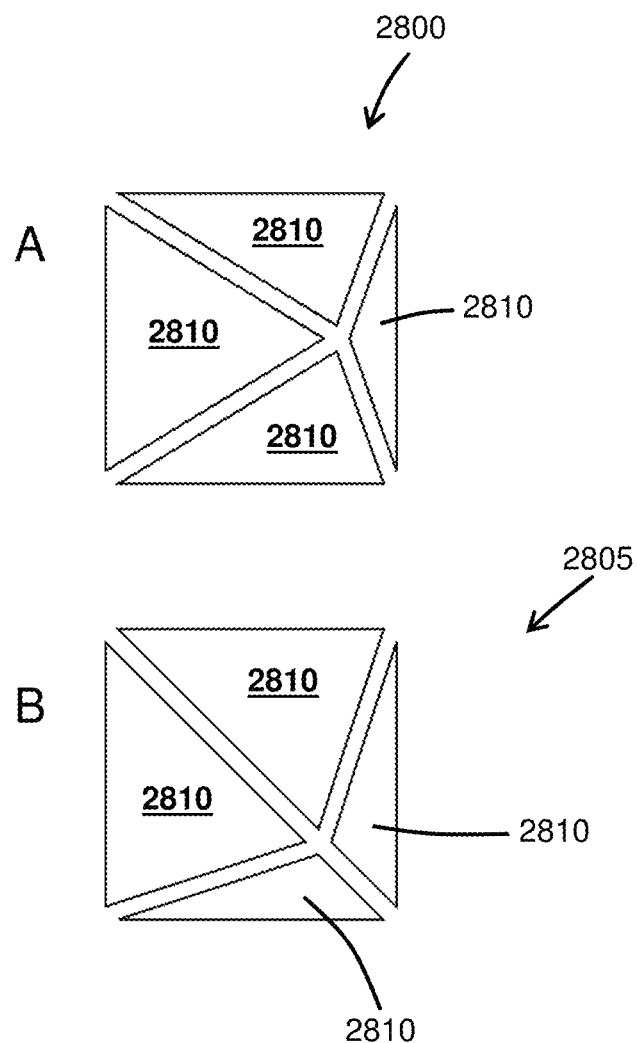
FIGS. 28A and 28B illustrate asymmetrical quadripole DEP electrode arrangements, formed from differently sized trianglular electrodes.

FIGS. 28A and 28B illustrate asymmetrical quadrupole DEP electrode arrangements 2800 and 2805, formed from differently sized trianglular electrodes 2810.

Figure 29:
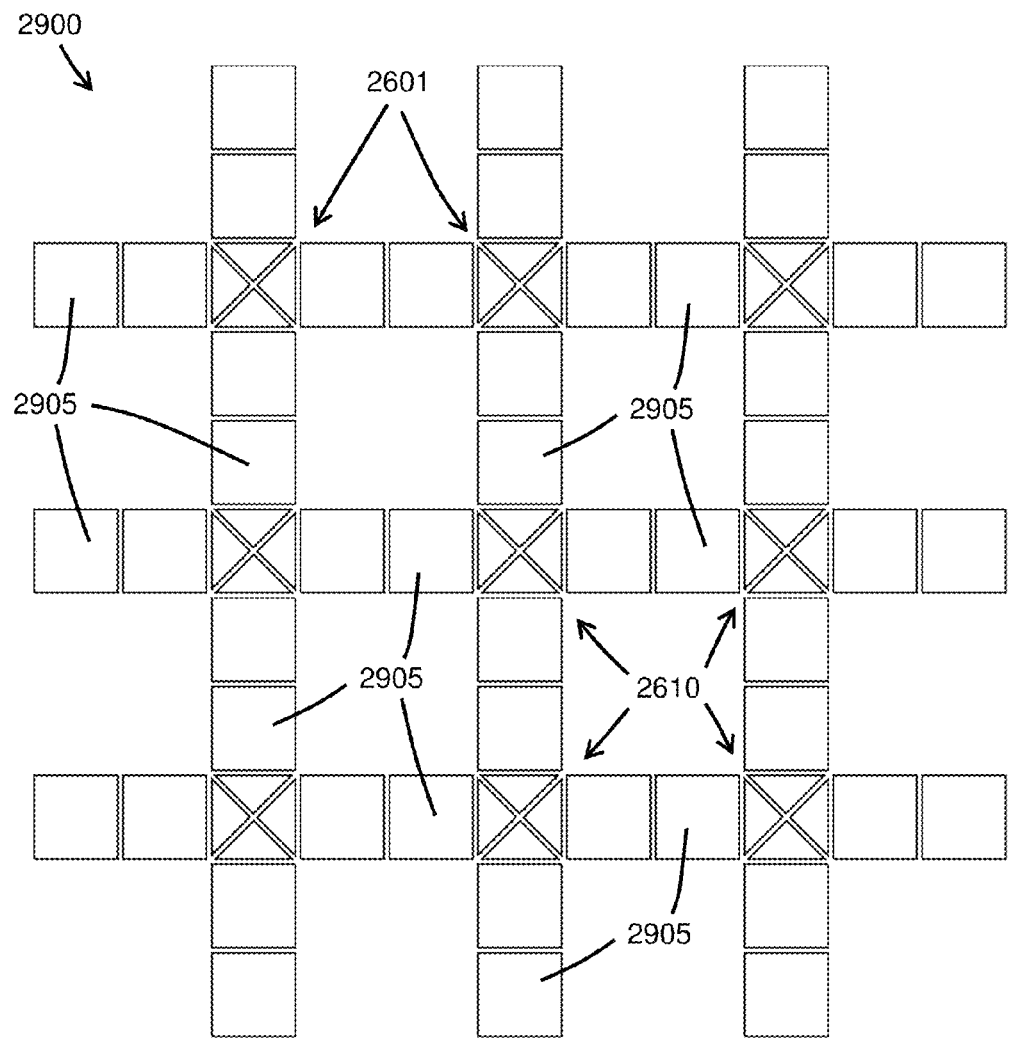
FIG. 29 illustrates an embodiment in which quadripole electrodes are arranged in an electrode array.

FIG. 29 illustrates an embodiment in which quadrupole electrodes 2610 are arranged in an electrode array 2900. In one embodiment, each electrode 2610 has a different DEP voltage configuration and can be used to trap a different type of particle. In the specific non-limiting embodiment illustrated here, a droplet including particles to be trapped may be transported to a DEP electrode from any direction on the array, and a droplet including the trapped one or more particles can be transported away from the quadrupole electrodes in any direction. Further, it should be noted that a droplet including particles to be trapped can be introduced directly onto the DEP electrode via an opening in a substrate, such as the top substrate (not shown). Similarly, a droplet including the trapped one or more particles may be extracted via an opening in a substrate, such as the top substrate (not shown). For example, it may be useful in some circumstances to flow liquid including one or more cells or particles to which cells are adhered into a reservoir associated with the top substrate for culturing or for collection and further processing. Further, the droplet operations electrodes and DEP electrodes may be associated with the top and/or bottom substrate.

Figure 30:
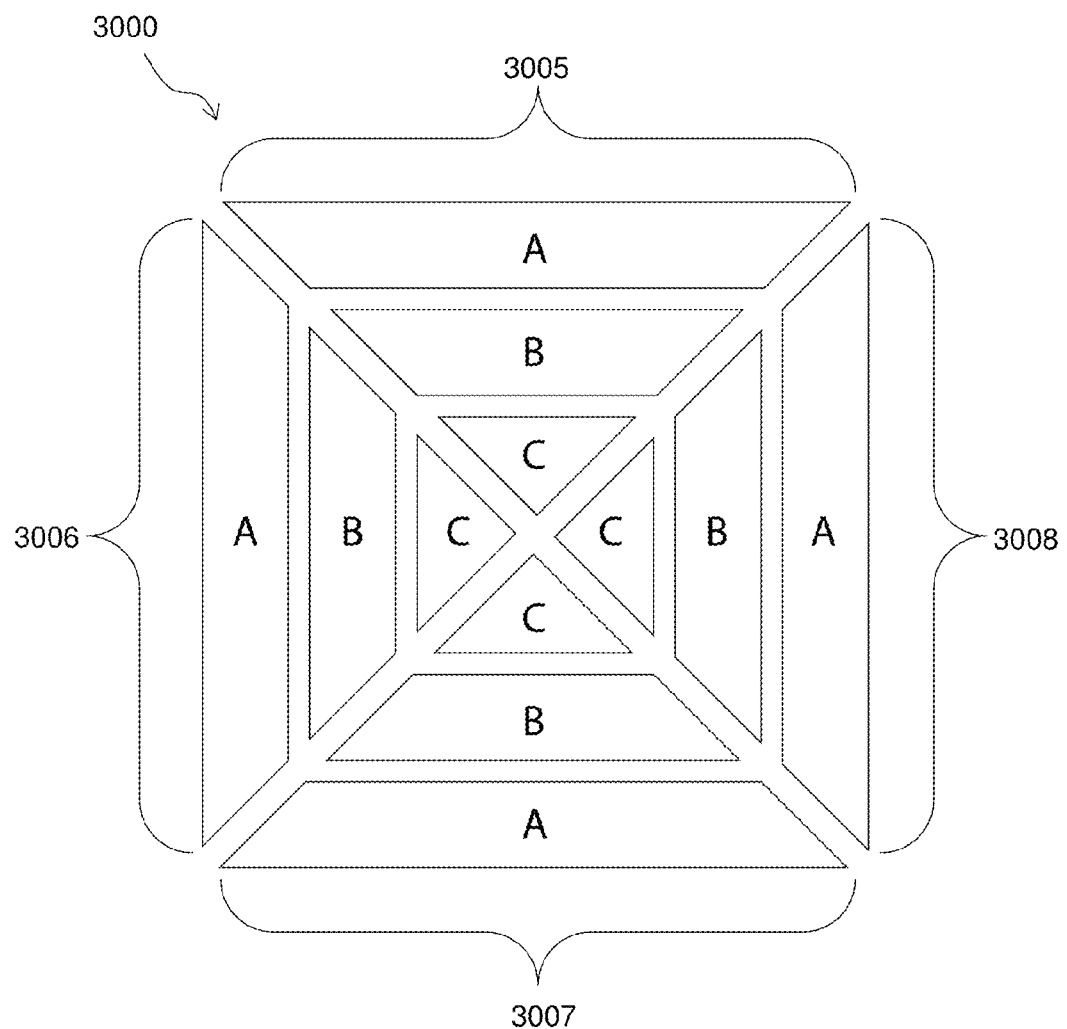
FIG. 30 shows a dynamically tunable quadripole DEP electrode arrangement in which each triangular electrode is further subdivided into sections A, B, C and D.

FIG. 30 shows a dynamically tunable quadripole DEP electrode arrangement 3000 in which each triangular electrode 3005, 3006, 3007, 3008 is further subdivided into sections A, B, and C. The subdivision of the triangles is generally concentric relative to the center of the square, i.e., breaks in each triangular electrode 3005, 3006, 3007, 3008 are generally parallel relative to the triangle's hypotenuse. Further, they are generally evenly spaced along a line extending from the right angle of each triangle to a center point on the triangle's hypotenuse. Variations in geometry are permissible, so long as the electrode arrangement achieves the intended purpose.

In operation, each concentric group of sub-electrodes can be activated independently to capture different numbers or sizes of particles. In one embodiment, groups A, B and C may be activated to capture the smallest quantity of particles; groups A and B may be activated to capture a larger quantity of particles; and group A may be activated to capture a still larger quantity of particles. In another embodiment, group C may be activated to capture the smallest number; group B may be activated to capture a larger quantity; and group A may be activated to capture a still larger quantity of particles. In one embodiment, each group of electrodes (i.e., the A group, the B group, and the C group) is activated together. In another embodiment, one or more members of any of the groups may be operated independently. For example, in one embodiment, the group C electrodes may be operated independently, such that it is possible to activate groups A and B with any combination of the group C electrodes. It is possible to have each group of electrodes activated at different voltages and/or frequencies (for example, group A can be activated at voltage V1 and frequency f1, B at voltage V2 and frequency f2, and C at voltage V3 and frequency f3) so that different particles can be segregated within a droplet at the gaps between the different groups based on their polarizabilities. Among several applications possible through this embodiment is the separation of dead and viable cells within a droplet along a circular path of different radii.

Figure 36:
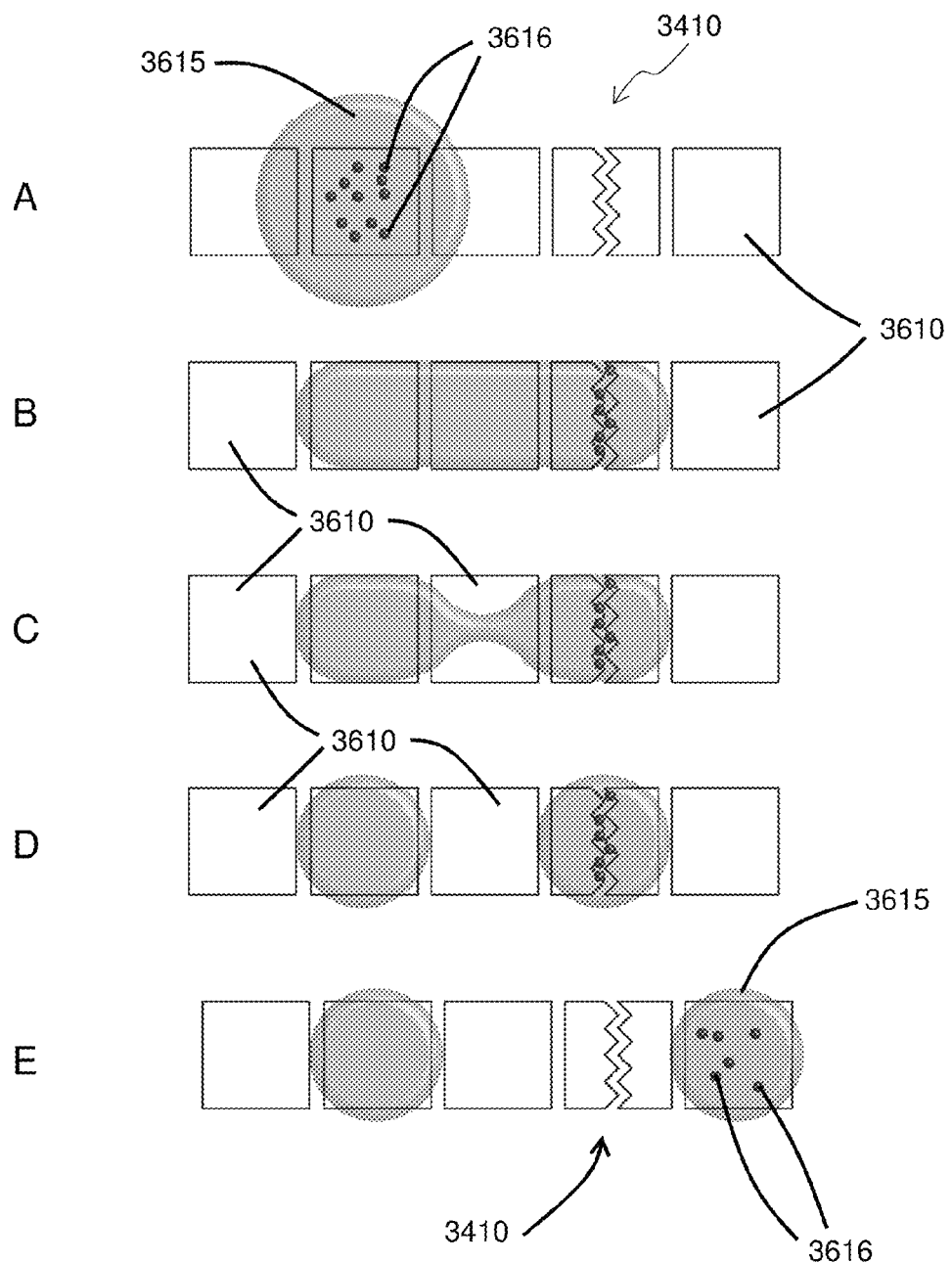
FIGS. 36A-36E illustrate an embodiment which is similar to the embodiment illustrated in FIG. 35.

FIGS. 31A-31C illustrate a configuration for applying a travelling wave DEP within a droplet. The travelling wave configuration translates particles that are levitated by DEP along the direction of a travelling wave. The phase of each adjacent DEP electrode may be rotated by about 90° relative to the adjacent electrode to produce the travelling wave effect. A region of a droplet actuator substrate includes DEP electrodes 3115 arranged alongside droplet operations electrode 3110. The illustrated embodiment includes four pairs of DEP electrodes. Each pair includes a first member on a first side of electrode 3110 and a second member on an opposite side of electrode 3110. As illustrated, the pairs are arranged sequentially in increasing order of polarity (0°, 90°, 180, 270°). However, other arrangements are possible, depending on where in the droplet it is desired for the particles of interest to be trapped. Four pairs of electrodes are illustrated, but it will be appreciated that more or less pairs are possible. The pairs are illustrated as being arranged alongside a single electrode; however, they may be arranged alongside a path of two or more electrodes, which is particularly useful for applying a DEP force in an elongated or slug-shaped droplet extended along a path of electrodes (e.g., as illustrated in FIG. 36). A splitting operation, such as the one shown in FIG. 36 may be used to divide the slug into a droplet including the trapped particles and a droplet substantially lacking the trapped particles. In this manner, particles having specific DEP properties may be regionalized within a first droplet and then split off into a smaller daughter droplet, thereby concentrating and/or isolating the beads.

Referring to FIGS. 31A-31C, a droplet 3120 including particles 3125 may be transported using droplet operations along electrode path 3130 onto electrode 3110. DEP electrodes 3115 may be activated causing particles to congregate along an edge of droplet 3130. A new droplet 3121 including particles 3125 may be dispensed using droplet operations from electrode 3110 onto electrode path 3135. In another embodiment, the order of polarity may be reversed to localize particles at a location which is distal to dispensing path 3135, and a droplet substantially lacking in particles may be dispensed. In another embodiment, rather than being transported into place, the droplet is loaded onto a reservoir electrode and beads in the droplet are subjected to DEP to congregate beads in a dispensing region of the droplet, such that a droplet with beads may be dispensed. In another embodiment, rather than being transported into place, the droplet is loaded onto a reservoir electrode and beads in the droplet are subjected to DEP to congregate beads away from a dispensing region of the droplet, such that a droplet lacking beads may be dispensed.

In an alternative embodiment, DEP is used to focus the particles between the oppositely facing electrodes and traveling wave DEP is used to move through the droplet. In this embodiment, the top DEP electrodes illustrated in FIG. 31 would be phase shifted as they are illustrated: 0, 90, 180, 270°, and the bottom electrodes would be 180, 270, 0, 90°, so that they are also phase shifted by 90°, but they are opposite in polarity to the opposing electrodes. In some embodiments, phases may be changed during operation, such that beads are caused to congregate in one region of a droplet, then travel to another region of the droplet.

Figure 31:
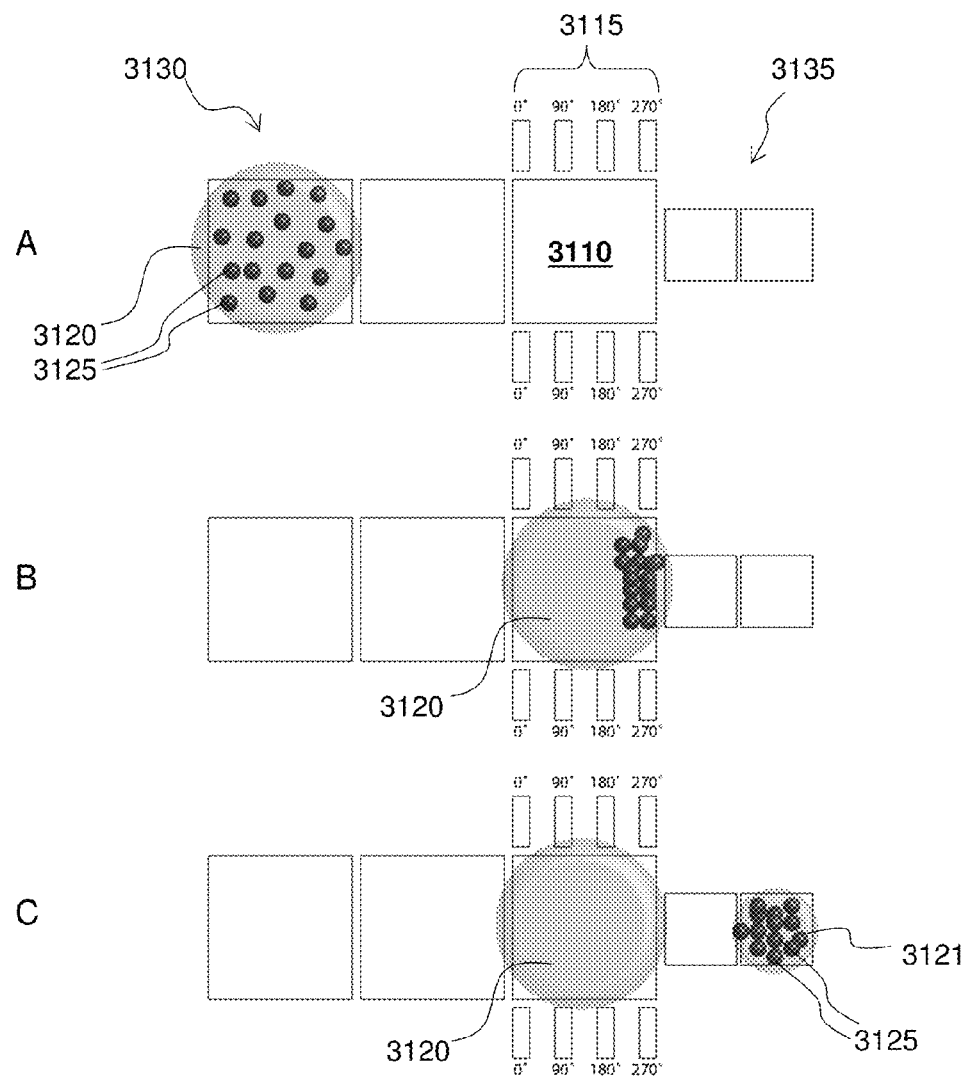
FIGS. 31A-31C illustrate a configuration for applying a travelling wave DEP within a droplet.
Figure 32:
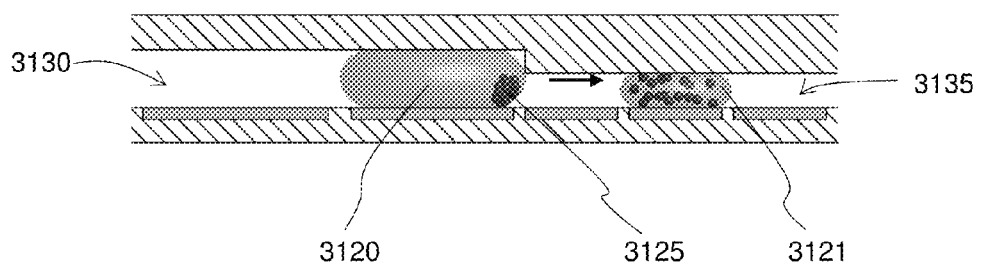
FIG. 32 shows a side view of the configuration illustrated in FIG. 31 showing how the particles may congregate at an edge of droplet.

FIG. 32 shows a side view of the configuration illustrated in FIG. 31 showing how the particles 3125 may congregate at an edge of droplet 3120. Droplet 3121 including particles 3125 can be split off using smaller unit droplet 3121. A mechanism similar to this can be used to concentrate the beads into the dispensed droplet in the DNA extraction application, explained in section 7.1.7, instead of magnetic beads.

Figure 33:
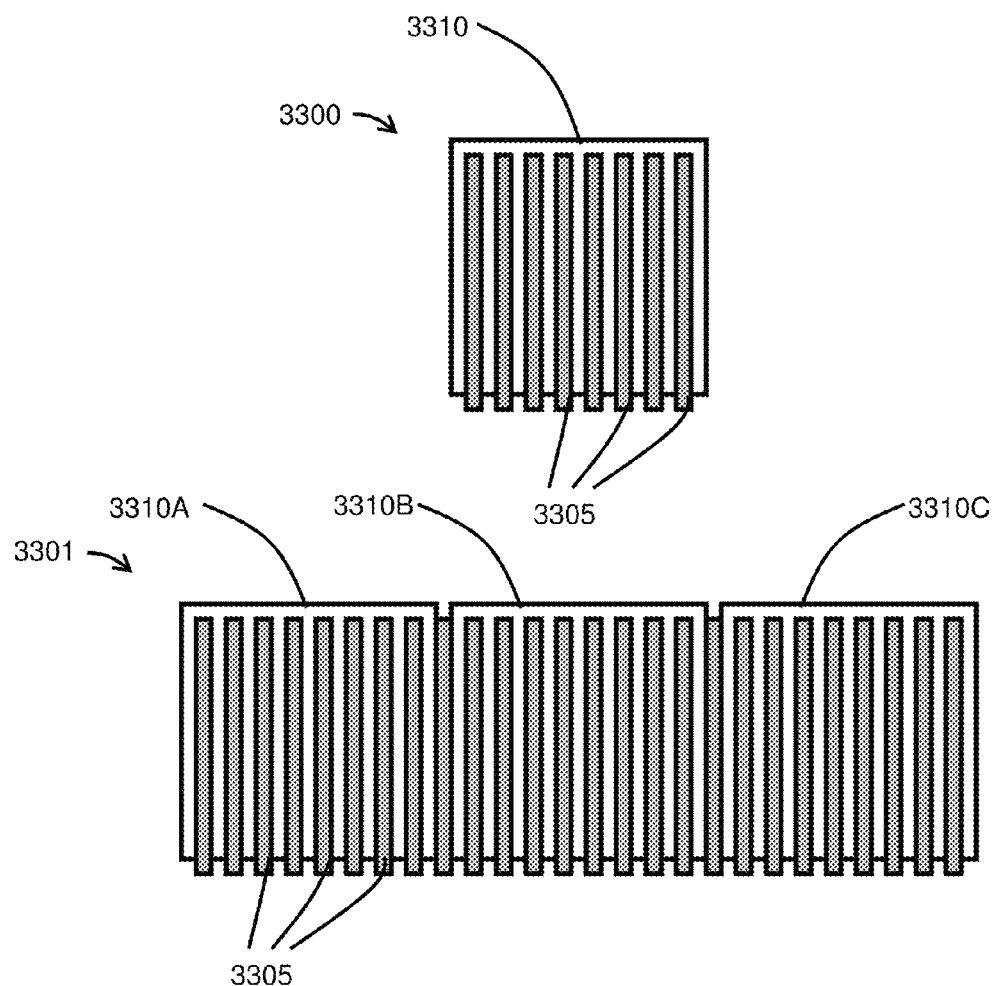
FIG. 33 illustrates travelling wave DEP configurations in which DEP electrodes are provided on a first substrate, and droplet operations electrodes are provided on a second substrate.

FIG. 33 illustrates travelling wave DEP configurations 3300, 3301 in which DEP electrodes 3305 are provided on a first substrate, and droplet operations electrodes 3310 are provided on a second substrate. In some embodiments, DEP electrodes 3305 are associated with the substrate which is across the droplet operations gap from the droplet operations electrode 3310. Moreover, the DEP electrodes 3305 may overlap the droplet operations electrode 3310, and the overlapping DEP electrodes 3305 may be positioned on the same or opposite sides of the droplet operations gap in a manner similar to electrodes 2405 and 2110 as shown in FIG. 24B. Configuration 3300 shows DEP electrodes 3305 arranged opposite a single droplet operations electrode 3310, such as a reservoir electrode. This configuration may, for example, be operated in a manner similar to electrodes 3110 and 3115 illustrated in FIG. 31. FIG. 33 shows DEP electrodes 3305 arranged opposite a path of droplet operations electrodes 3310. In operation, the electrodes 3310 may be activated, causing a bead-containing droplet to take on an elongated configuration atop the electrodes, e.g., as illustrated in FIG. 36. Each DEP electrode may be phase shifted relative to its neighboring DEP electrodes, thereby creating a traveling wave DEP effect, which transports the beads to an end region of the droplet. Electrode 3310B may then be deactivated, causing the droplet to split and yielding two daughter droplets. DEP electrodes may be arranged alongside two, three or more droplet operations electrodes. A slug-shaped droplet may be provided on the droplet operations electrodes. The DEP electrodes may be used to localize particles in one end of the slug. An intermediate electrode may be deactivated to split the slug into two droplets, one including substantially all of the particles and one substantially lacking the particles. Typically, one of the daughter droplets will include a higher concentration of the beads. In some cases, substantially all of the beads will make their way into one daughter droplet, while the other daughter droplets will be substantially free of the beads. In other cases, the beads may be distributed among two or more of the daughter droplets. Among other things, this technique is useful for concentrating beads for analysis or for conducting a merge-and-split bead washing protocol.

Figure 34:
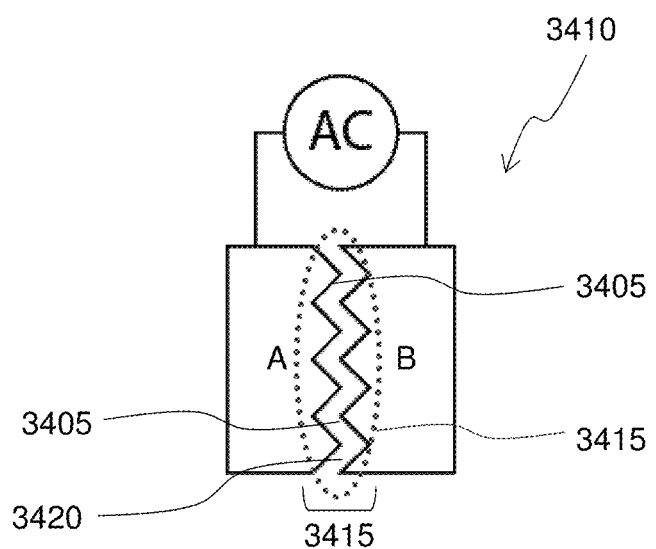
FIG. 34 illustrates an alternative electrode configuration.

FIG. 34 illustrates an alternative electrode configuration. The configuration includes two electrodes 3410A,B with fringed edges 3405 separated by a gap 3420. The two electrodes have different polarities. The electrodes A and B have fringed edges 3405 designed to generate a DEP field. The electrodes A and B may be operated together as a single droplet operations electrode or separately as a set of DEP electrodes. In operation, particles will line up in a DEP region 3415, generally along the gap 3420 between the two electrodes 3410A and B.

FIGS. 35A-35C show an electrode path 3505 including DEP electrodes 3410A & B. FIGS. 35A and 35B illustrate how a particle-containing droplet 3520 can be transported using droplet operations to electrode 3410, and the particles can be trapped within droplet 3520 by electrodes 3410. FIG. 35C shows how liquid can be exchanged around immobilized droplets, e.g., for washing or introducing sample and/or reagents to the particles or for removing supernatant from the particles for further analysis. Further, the particles in the new droplets can be transported away by removing the DEP field and using adjacent electrodes from electrode path 3505 to transport droplet 3520. In this manner, particles can be localized in a droplet and concentrated by removing liquid from the droplet without substantial loss of particles. The technique for conducting this operation may, for example, be a merge-and-split operation.

Figure 35:
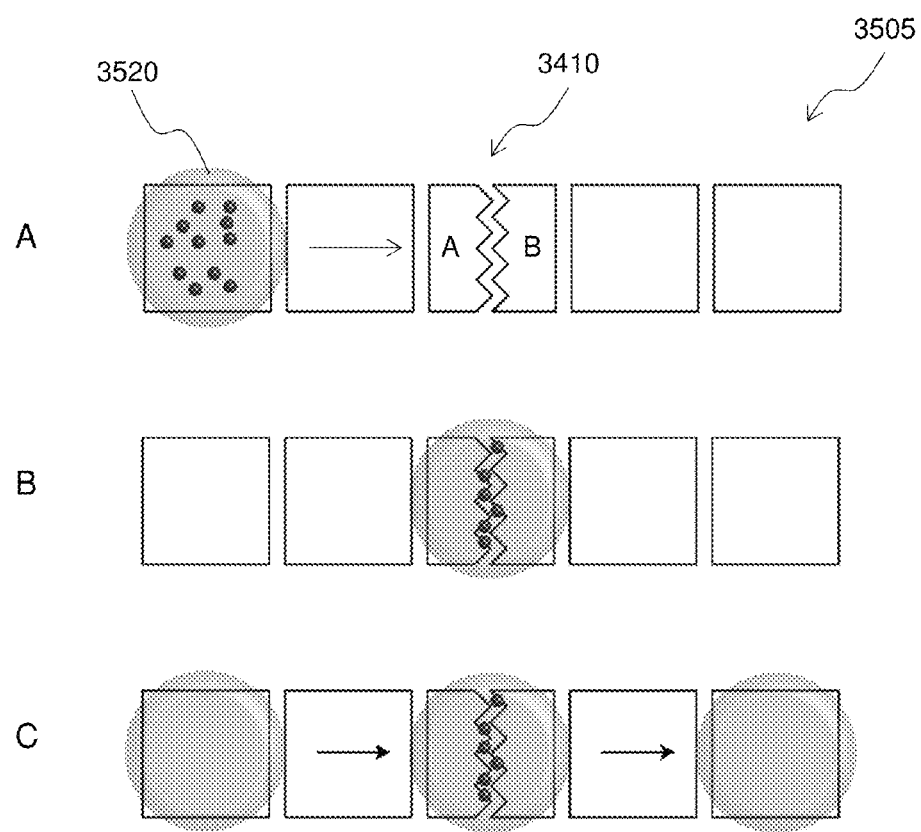
FIGS. 35A-35C show an electrode path including DEP electrodes.

FIGS. 36A-36E illustrate an embodiment which is similar to the embodiment illustrated in FIG. 35. DEP electrode 3410 is used to trap particles during a droplet-splitting operation mediated by electrodes 3610, which are configured in an electrode path. The electrode path also includes a DEP electrode 3410. FIG. 36A illustrates an electrode path including a particle-containing droplet 3615. FIG. 36B shows the droplet elongated across three activated electrodes 3610, with DEP electrode 3410 activated to attract and trap particles 3616 within droplet 3615. FIGS. 36C and D show deactivation of an intermediate electrode to split the droplet, leaving a first droplet including substantially all of the particles and a second droplet substantially lacking particles. Either or both of these droplets may be subjected to further droplet operations, e.g., as part of an assay protocol. FIG. 36E shows the first droplet 3615 being transported away from DEP electrode 3410 with the particles 3616. In a washing protocol, the particle-containing droplet may be combined with a wash droplet and split as described above multiple times until the wash is sufficiently complete. In an alternative embodiment, the path of electrodes may include droplet operations electrodes 3610, and DEP electrode 3410 may be positioned on the substrate across the droplet operations gap from the droplet operations electrode, e.g., as described with respect to electrodes 2405 and 2410 in FIG. 24. In yet another embodiment, DEP electrodes 3410 may be positioned in the path of droplet operations electrodes 3610 as illustrated, and one or more droplet operations electrodes may be positioned on the substrate across the droplet operations gap from DEP electrodes 3410 to hold the droplet in place during DEP operation.

Figure 37:
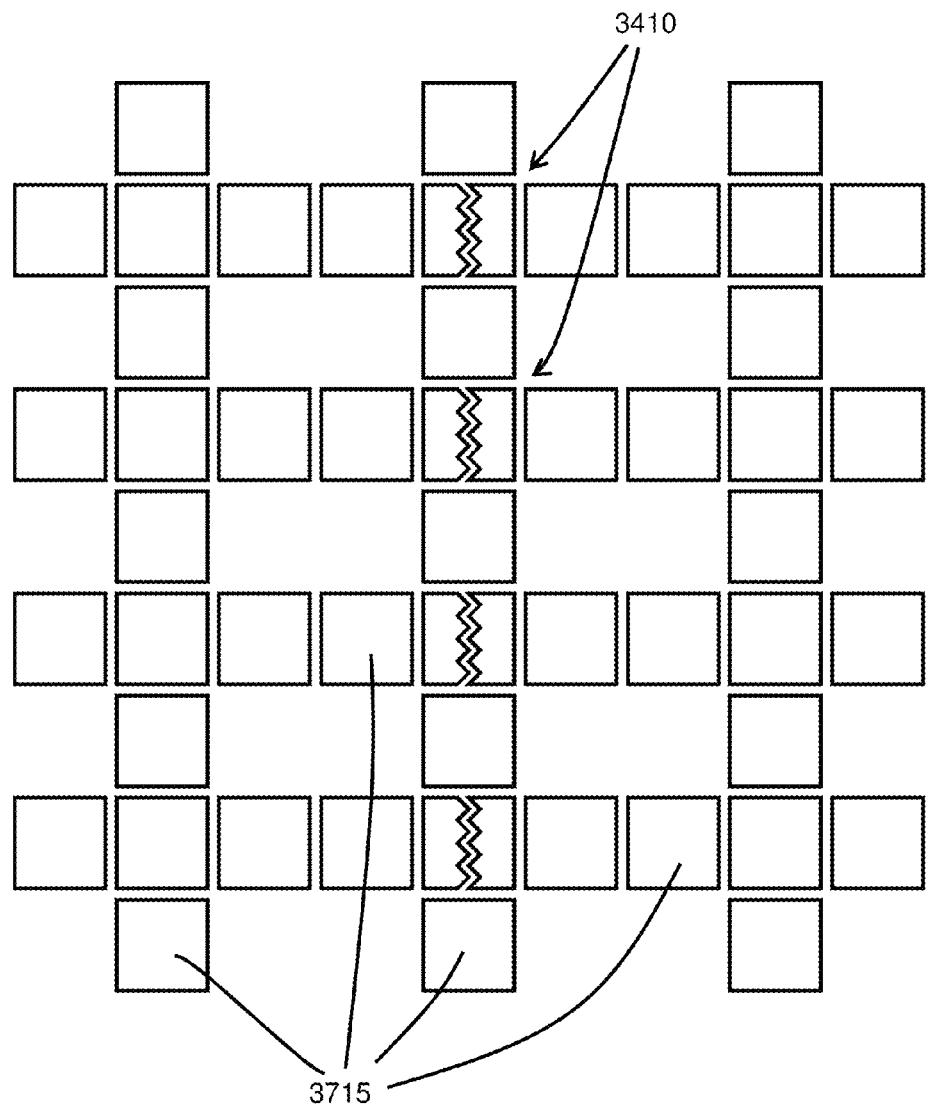
FIG. 37 illustrates an array of electrodes including DEP electrodes.

FIG. 37 illustrates an array of electrodes 3715 including DEP electrodes 3410, as described above. In one embodiment, each electrode 3410 has a different DEP configuration and can be used to differentially trap particles having different DEP characteristics. In the specific non-limiting embodiment illustrated here, a droplet including particles to be trapped may be transported to a DEP electrode from any direction on the array, and a droplet including the trapped one or more particles can be transported away from the quadrupole electrodes in any direction. Further, it should be noted that a droplet including particles to be trapped can be introduced directly onto the DEP electrode via an opening in a substrate, such as the top substrate (not shown). Similarly, a droplet including the trapped one or more particles may be extracted via an opening in a substrate, such as the top substrate (not shown). For example, it may be useful in some circumstances to flow liquid including one or more cells or particles to which cells are adhered into a reservoir associated with the top substrate for culturing or for collection and further processing. Further, the droplet operations electrodes and DEP electrodes may be associated with the top and/or bottom substrate.

Figure 38:
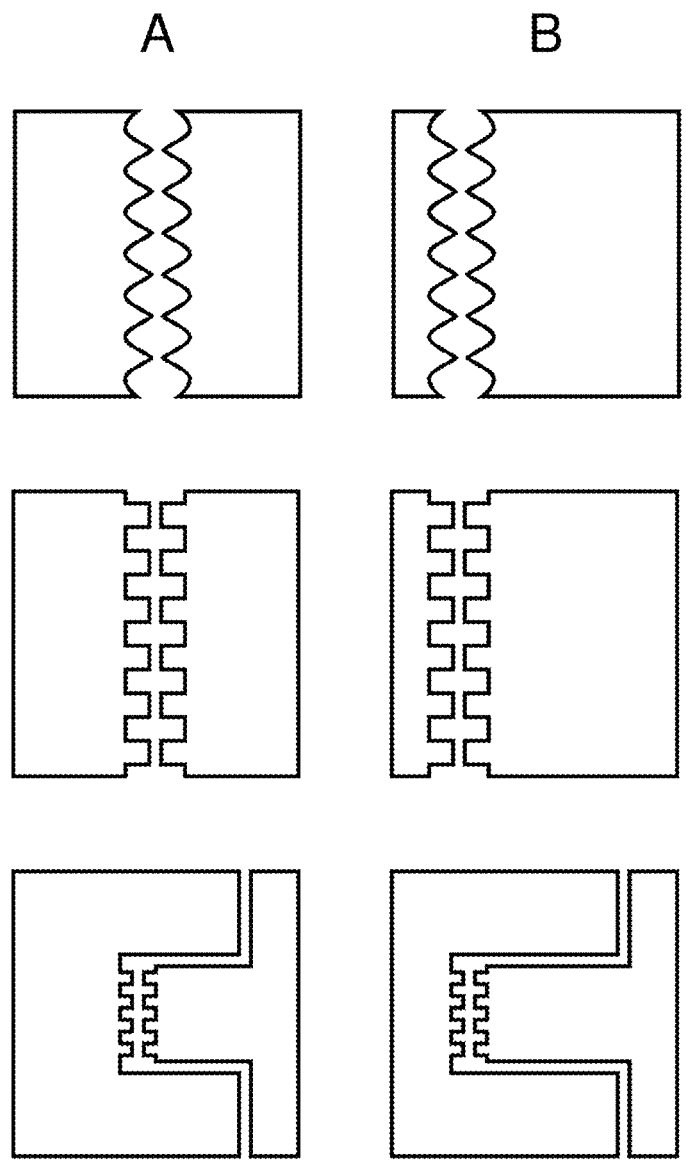
FIGS. 38A and 38B illustrate several alternatives to electrode described herein.

FIGS. 38A and 38B illustrate several alternatives to electrode 3410 described above. In column A, the fringes are generally centrally located within the electrode configuration. In column B, the fringes are asymmetrically located within the electrode configuration. Various fringe types are also illustrated.

Figure 39:
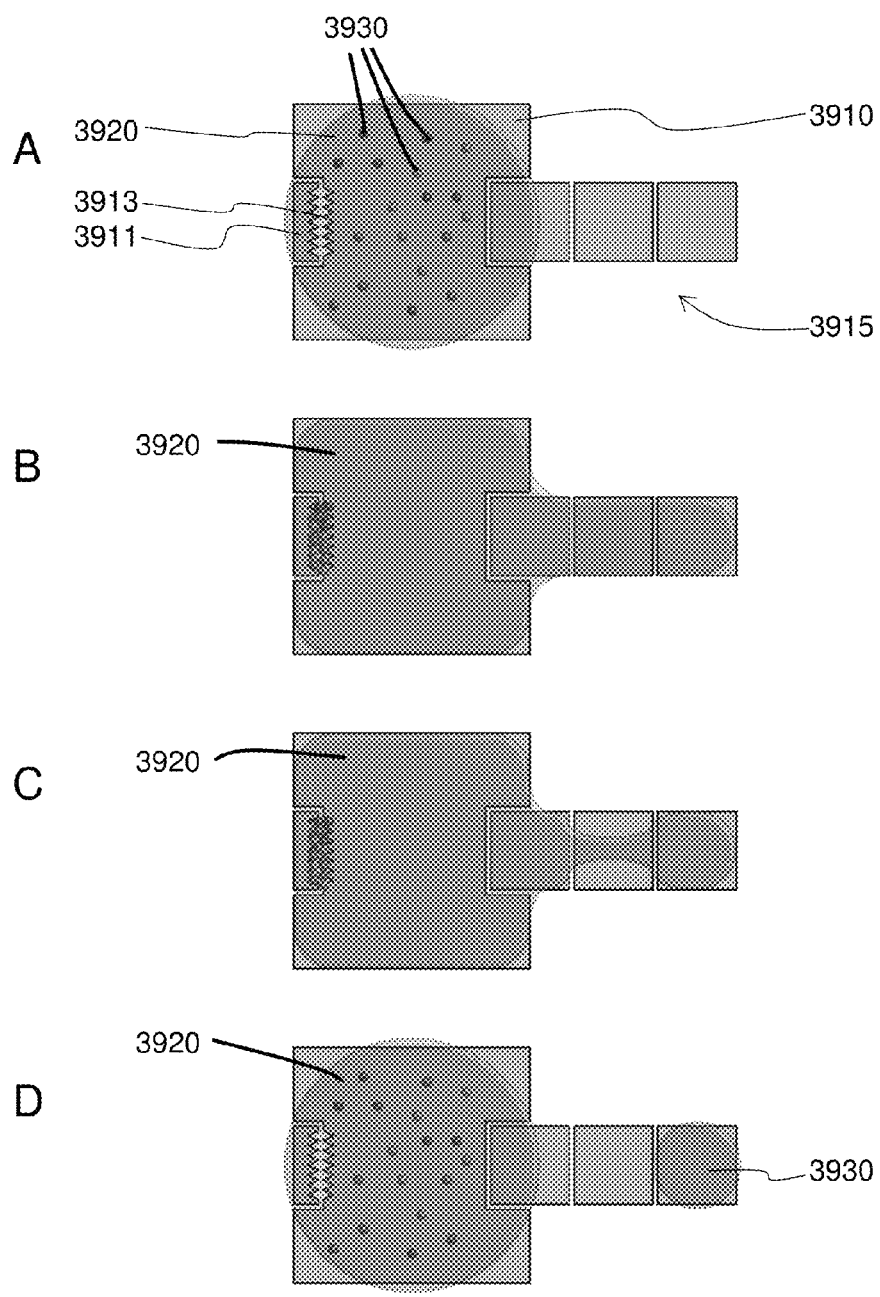
FIGS. 39A-39D illustrate a reservoir electrode having a DEP electrode inset.

FIGS. 39A-39D illustrate a reservoir electrode 3910 having a DEP electrode inset 3911. DEP electrode inset 3911 includes a fringed region which corresponds to a fringe region on reservoir electrode 3910. The configuration is useful for dispensing a supernatant droplet 3930 onto a path or array of electrodes 3915 from a particle-containing droplet 3920. In FIG. 39A, all electrodes in the arrangement are off. In FIG. 39B, reservoir electrode 3910 and electrodes 3915 are on, and DEP electrode inset 3911 is activated to effect a DEP field in the region of the fringed edges 3913, trapping the particles 3930 in the DEP field. In FIG. 39C, an intermediate one of the electrodes 3915 is deactivated to cause formation of droplet 3930, shown in FIG. 39D. In this manner, a supernatant droplet 3930 substantially lacking in the particles is dispensed from a reservoir, while droplet 3920 in the reservoir retains substantially all of the particles.

FIGS. 40A-40D illustrate a configuration useful for dispensing a droplet 4030 including substantially all particles 4035 from a particle-containing droplet 4020 on reservoir electrode 4010 onto a path or array of electrodes 4015. Alternatively, droplet 4030 includes a concentration of particles from particle-containing droplet 4020, wherein the concentration of particles in droplet 4030 is greater than the concentration in parent droplet 4020. Electrodes 4015 include a DEP electrode 4025 at a location which is distal relative to reservoir electrode 4010. Further, the fringe region 4026 of the DEP electrode is distal within electrode 4025 relative to reservoir electrode 4010.

Figure 40:
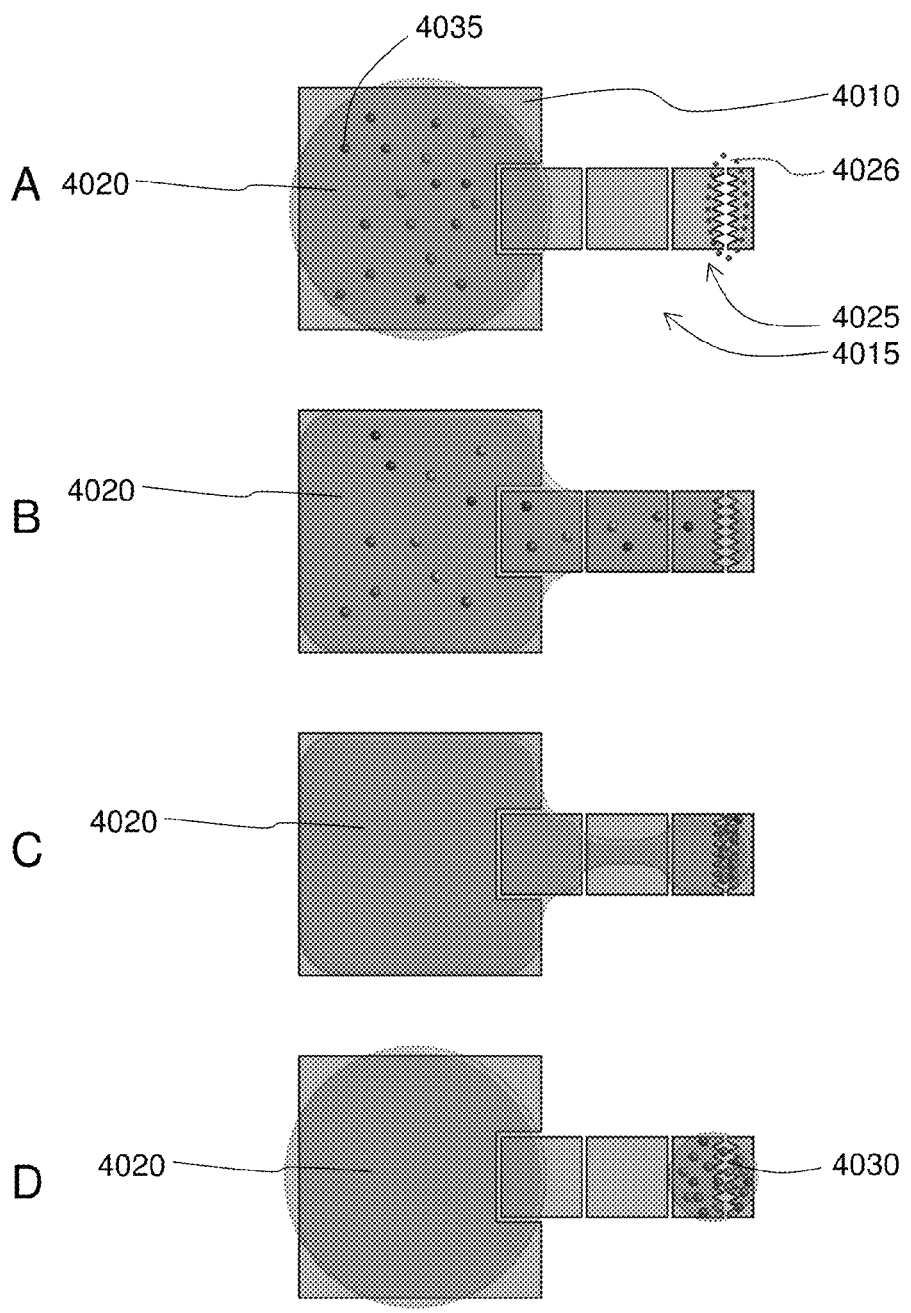
FIGS. 40A-40D illustrate a configuration useful for dispensing a droplet including substantially all particles from a particle-containing droplet on reservoir electrode onto a path or array of electrodes.

In FIG. 40A, all electrodes in the arrangement are off. In FIG. 40B, reservoir electrode 4010 and electrodes 4015 are on, and DEP electrode 4025 is activated to effect a DEP field in the fringe region 4026, attracting and trapping the particles in the DEP field. In FIG. 40C, an intermediate one of the electrodes 4015 is deactivated to cause formation of droplet 4030, shown in FIG. 40D. In this manner, a droplet including substantially all particles is dispensed from reservoir electrode 4010, while droplet 4020 retains substantially none of the particles. It will be appreciated that by appropriate timing and selection of DEP field properties (e.g., size of the fringe region), a droplet including less than substantially all of the particles may dispensed, leaving some particles in droplet 4020. In this manner, droplets including predetermined quantities of particles may be dispensed.

Figure 41:
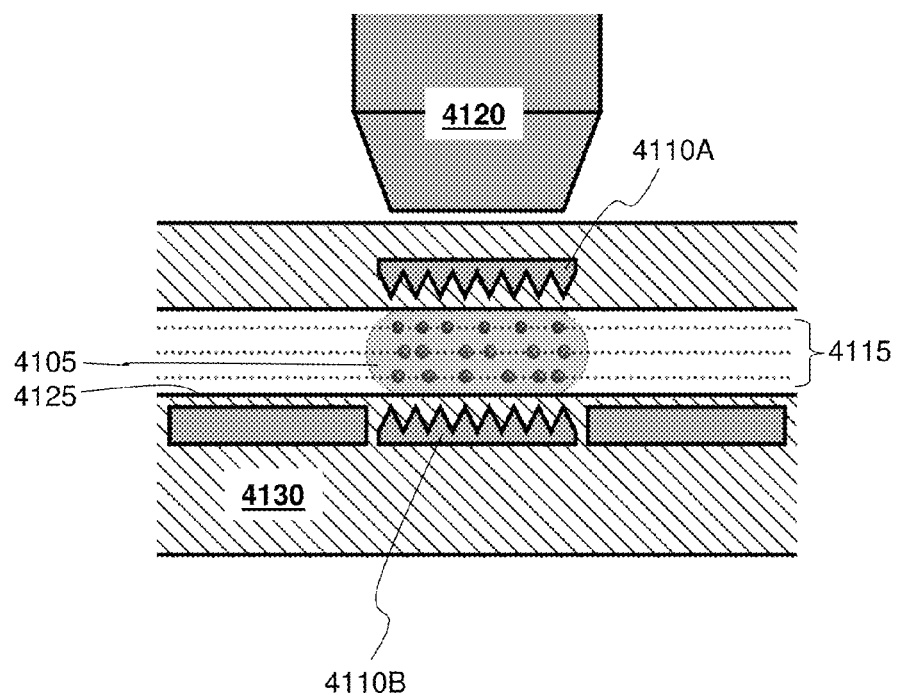
FIG. 41 illustrates the use of DEP to separate particles within a droplet for imaging.

FIG. 41 illustrates the use of DEP to separate particles within a droplet 4105 for imaging. In this embodiment DEP electrodes 4110A,B are arranged on top and bottom substrates, respectively, of the droplet actuator. The DEP force generated by DEP electrodes 4110A,B causes particles with different properties to separate vertically in planes 4115. A confocal microscope 4120 can be used to detect signal from particles in specific planes of the droplet. For example, several assays for different analytes can be performed on the droplet actuator, and particles with fluorescing compounds from the assays can be separated in planes 4115 within droplet 4105. Ideally the planes 4115 are generally horizontal with the surface 4125 of the bottom substrate 4130. Confocal microscope 4120 can be used to detect fluorescence of each particle set by eliminating fluorescence emanating from planes other than the plane or planes in which the target particle set is located. An analogous approach can also be used for quantifying particles of each type. Particles in each plane can be imaged and counted. Additionally, levitating particles within a droplet can be used in a setting in which it is desirable to eliminate background fluorescence. Particles can be levitated using the DEP arrangement shown in FIG. 41, and confocal microscope 4120 can focus on signal from the particles while eliminating background signal.

It should also be noted that DEP arrangements such as those described herein can be used to agitate beads within a droplet. For example, beads may settle in a droplet after time or may be attracted to weak magnetic forces from magnets located elsewhere on a droplet actuator. Beads can be resuspended within a reservoir by alternating between negative and positive DEP to redistribute beads within a droplet. A similar effect can be achieved using DEP electrodes arranged on the top and bottom plates, e.g., as shown in FIG. 41.

8.4 Systems

As will be appreciated by one of skill in the art, the invention may be embodied as a method, system, or computer program product. Accordingly, various aspects of the invention may take the form of hardware embodiments, software embodiments (including firmware, resident software, microcode, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, compiled, interpreted, or otherwise processed in a suitable manner, if necessary, and stored in a computer memory. In the context of this document, a computer-usable or computer-readable medium may be any medium that can include, store, communicate, propagate, or transport the program for use by or in connection with the instruction execution system, apparatus, or device.

Computer program code for carrying out operations of the invention may be written in an object oriented programming language such as Java, Smalltalk, C++ or the like. However, the computer program code for carrying out operations of the invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Certain aspects of invention are described with reference to various methods and method steps. It will be understood that each method step can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the methods.

The computer program instructions may also be stored in a computer-readable memory that can direct a computer or other programmable data processing apparatus to function in a particular manner, such that the instructions stored in the computer-readable memory produce an article of manufacture including instruction means which implement various aspects of the method steps.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing various functions/acts specified in the methods of the invention.

CONCLUDING REMARKS

The foregoing detailed description of embodiments refers to the accompanying drawings, which illustrate specific embodiments of the invention. Other embodiments having different structures and operations do not depart from the scope of the invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the invention may be changed without departing from the scope of the invention. Furthermore, the foregoing description is for the purpose of illustration only, and not for the purpose of limitation.

We claim:

1. A method of washing beads comprising:
   (a) providing a droplet actuator comprising:
      (i) two substrates arranged to provide a gap;
      (ii) electrodes associated with one or both of the two substrates and arranged for conducting droplet operations in the gap;
      (iii) a starting droplet situated in the gap comprising magnetically responsive beads within a region of a magnetic field and a starting concentration of the substance;
   (b) conducting one or more electrowetting-mediated droplet operations to merge a wash droplet with the droplet provided in step (a)(iii) to yield a combined droplet;
   (c) conducting one or more droplet operations while restraining the beads to divide the combined droplet, yielding a set of daughter droplets comprising:
      (i) a first daughter droplet retaining at least about 99% of the beads and having a decreased concentration of the substance relative to the starting concentration;
      (ii) a second daughter droplet which is separated from the at least one surface; and
   (d) transporting the first daughter droplet away from the magnetic field.

2. The method of claim 1 comprising repeating steps (b) and (c) until a 99% reduction in the starting material is achieved relative to the starting concentration of the substance.

3. The method of claim 1 comprising repeating steps (b) and (c) until a 99.9% reduction in the starting material is achieved relative to the starting concentration of the substance.

4. The method of claim 1 comprising repeating steps (b) and (c) until a 99.99% reduction in the starting material is achieved relative to the starting concentration of the substance.

5. The method of claim 1 comprising repeating steps (b) and (c) until a 99.999% reduction in the starting material is achieved relative to the starting concentration of the substance.

6. The method of claim 1 comprising repeating steps (b) and (c) until a 99.999% reduction in the starting material is achieved relative to the starting concentration of the substance and substantially all of the beads are retained relative to the quantity of beads provided in the starting droplet.

7. The method of claim 1 comprising repeating steps (b) and (c) until a 99.999% reduction in the starting material is achieved relative to the starting concentration of the substance and substantially all of the beads are retained relative to the quantity of beads provided in the starting droplet.

8. The method of claim 1 comprising repeating steps (b) and (c) until a 99.999% reduction in the starting material is achieved relative to the starting concentration of the substance and substantially all of the beads are retained relative to the quantity of beads provided in the starting droplet.

9. The method of claim 1 comprising repeating steps (b) and (c) until a 99.999% reduction in the starting material is achieved relative to the starting concentration of the substance and substantially all of the beads are retained relative to the quantity of beads provided in the starting droplet.

10. The method of claim 1 wherein the restraining comprises aggregating the beads in a region of the droplet.

11. The method of claim 1 further comprising combining the first daughter droplet with a second droplet to yield a combined droplet and transporting the combined droplet away from the magnetic field.

* * * * *

UNITED STATES PATENT AND TRADEMARK OFFICE
CERTIFICATE OF CORRECTION

PATENT NO. : 8,637,317 B2
APPLICATION NO. : 12/985409
DATED : January 28, 2014
INVENTOR(S) : Pamula et al.

Page 1 of 1

It is certified that error appears in the above-identified patent and that said Letters Patent is hereby corrected as shown below:

Title Page, Item (75) Inventors should read:
--(75) Inventors: Vamsee K. Pamula, Durham, NC (US);
Arjun Sudarsan, Durham, NC (US);
Ramakrishna Sista, Morrisville, NC (US)--.

Signed and Sealed this
Sixteenth Day of June, 2015

Michelle K. Lee
*Director of the United States Patent and Trademark Office*

UNITED STATES PATENT AND TRADEMARK OFFICE
CERTIFICATE OF CORRECTION

PATENT NO. : 8,637,317 B2  
APPLICATION NO. : 12/985409  
DATED : January 28, 2014  
INVENTOR(S) : Pamula et al.

Page 1 of 1

It is certified that error appears in the above-identified patent and that said Letters Patent is hereby corrected as shown below:

Title Page, Item (75) Inventor is corrected to read:
-- Vamsee K. Pamula, Durham (NC);
    Arjun Sudarsan, Durham (NC);
    Ramakrishna Sista, Morrisville (NC);
    Richard B. Fair, Durham (NC) --.

Signed and Sealed this  
Fourth Day of August, 2015

Michelle K. Lee  
*Director of the United States Patent and Trademark Office*